US008399426B2

(12) United States Patent
Kim et al.

(10) Patent No.: US 8,399,426 B2
(45) Date of Patent: Mar. 19, 2013

(54) METHOD FOR TREATING BREAST CANCER USING ADENINE NUCLEOTIDE TRANSLOCATOR 2 (ANT2) SIRNA OR ANT2 SHRNA

(75) Inventors: Chul Woo Kim, Seoul (KR); Ji Young Jang, Seoul (KR)

(73) Assignee: Bioinfra Inc., Seoul (KR)

( * ) Notice: Subject to any disclaimer, the term of this patent is extended or adjusted under 35 U.S.C. 154(b) by 0 days.

(21) Appl. No.: 13/030,860

(22) Filed: Feb. 18, 2011

(65) Prior Publication Data

US 2011/0207798 A1 Aug. 25, 2011

Related U.S. Application Data

(63) Continuation-in-part of application No. 12/293,416, filed on Sep. 17, 2008, now abandoned.

(30) Foreign Application Priority Data

Apr. 11, 2006 (KR) ........................ 10-2006-0032823

(51) Int. Cl.
*A61K 31/70* (2006.01)
*C07H 21/04* (2006.01)

(52) U.S. Cl. ........................................ 514/44; 536/24.5

(58) Field of Classification Search ........................ None
See application file for complete search history.

(56) References Cited

U.S. PATENT DOCUMENTS

| | | | | |
|---|---|---|---|---|
| 5,981,279 | A | 11/1999 | Weiss | |
| 6,277,832 | B1 | 8/2001 | Sugiyama et al. | |
| 2004/0002077 | A1 | 1/2004 | Taira et al. | |
| 2006/0210535 | A1 | 9/2006 | Borgne et al. | |
| 2006/0241069 | A1 | 10/2006 | Fishman et al. | |
| 2006/0276527 | A1 * | 12/2006 | Tidmarsh | 514/406 |

OTHER PUBLICATIONS

Ross, et al., "*Homo sapiens* solute carrier family 25 (mitochondrial carrier; adenine nucleotide translocator), member 5 (SLC25A5), mRNA", NCBI GenBankAccession No. NM_001152 (Mar. 24, 1999).

Faure Vogny, et al.. "Expression of oxidative phosphorylation genes in renal tumors and tumoral cell lines.", Mol. Carcinog, 16(3):165-172 (Jul. 1996).

Chevrollier, et al., "ANT2 isoform required for cancer cell glycolysis", J. Bioenerg Biomembr, 37 (5):307-316 (Oct. 2005).

Le Bras, et at., "Chemosensitization by knockdown of adenine nucleotide translocase-2", Cancer Res. 66 (18):9143-9152 (Sep. 15, 2006).

* cited by examiner

*Primary Examiner* — Tracy Vivlemore
(74) *Attorney, Agent, or Firm* — Lucas & Mercanti, LLP

(57) ABSTRACT

The present invention relates to adenine nucleotide translocator 2 (ANT2) siRNA (small interfering RNA) or ANT2 shRNA (short hairpin RNA) suppressing the expression of ANT2 gene expression and anticancer agent containing the same. Furthermore, the present invention relates to methods for treating breast cancers or stem cells of a breast cancer by treating the same with ANT2 siRNA or ANT2 shRNA. In addition, the invention provides a method for inhibiting metastasis of breast cancer cells with ANT2 siRNA or ANT2 shRNA.

11 Claims, 47 Drawing Sheets

FIG. 3
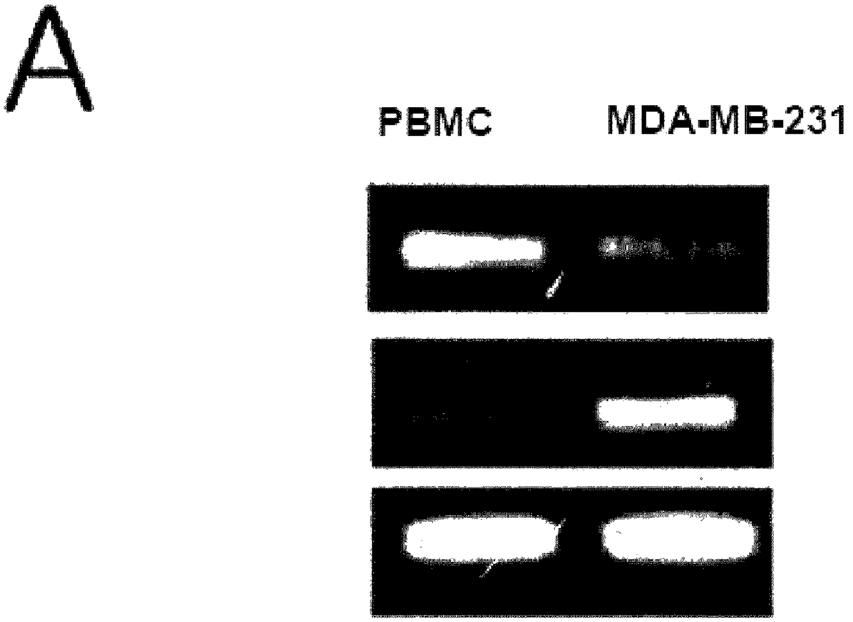
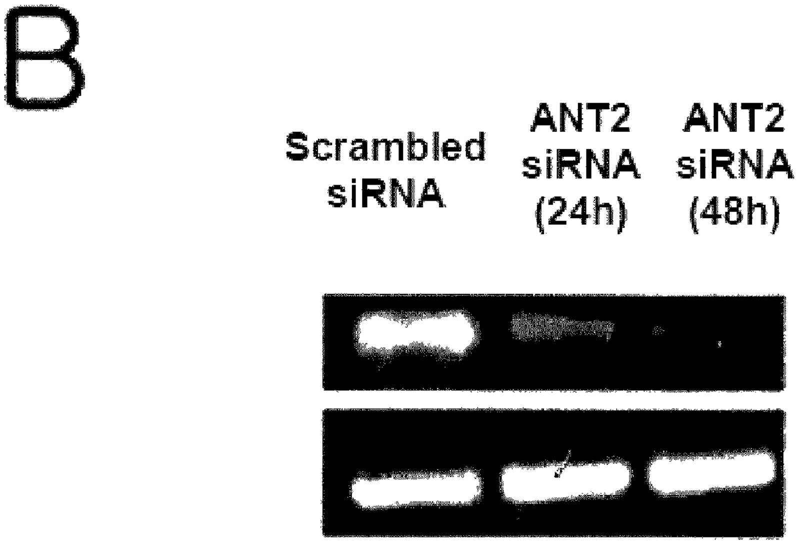

RT-PCR

| | | |
|---|---|---|
| Scrambled siRNA | + | - |
| ANT2 siRNA | - | + |

FIG. 12
A
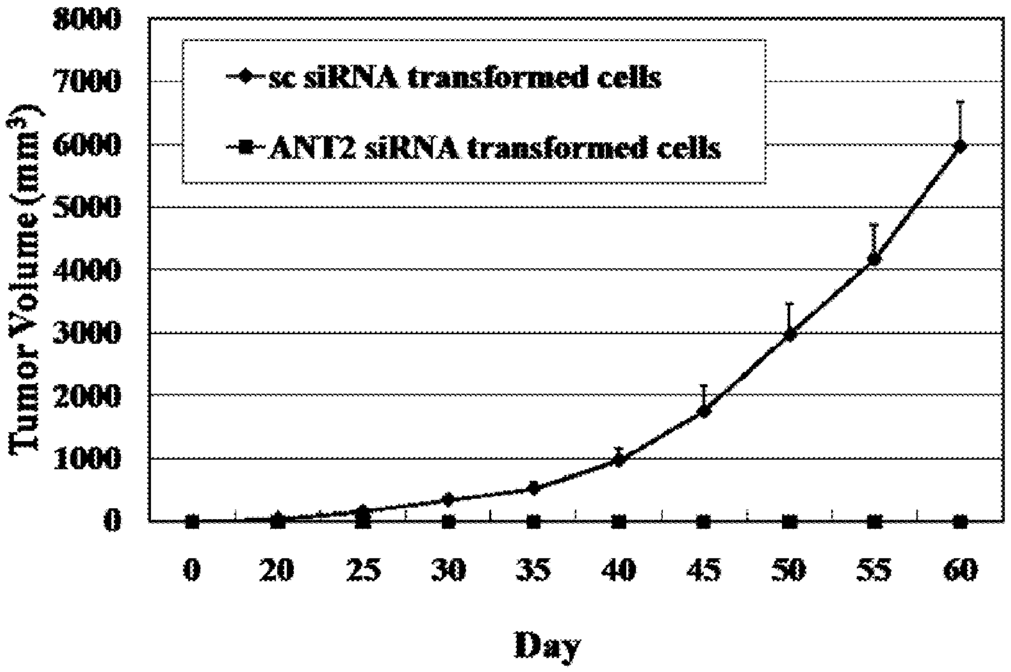
B
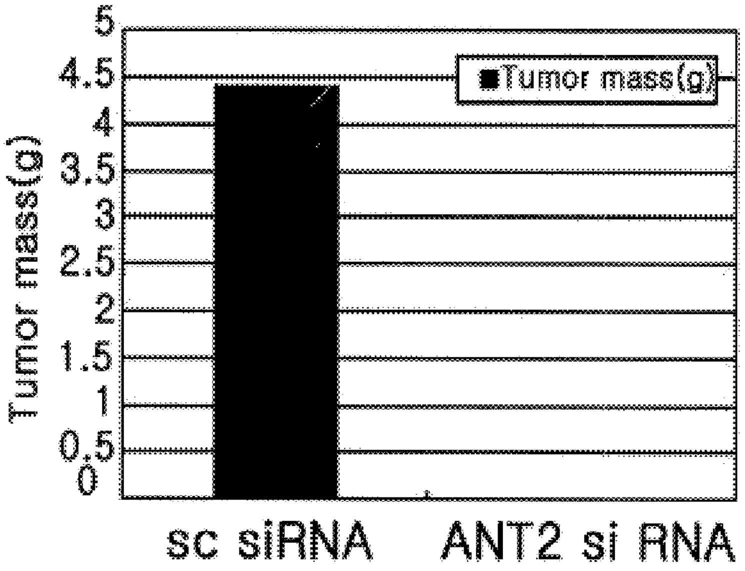

FIG. 15

Human ANT2 : NM 001152

1 ccgcagcgcc ggagtcaaac ggttcccggc ccagtcccgt cctgcagcag tctgcctcct
61 ctttcaacat gacagatgcc gctgtgtcct tcgccaagga cttcctggca ggtggagtgg
121 ccgcagccat ctccaagacg gcggtagcgc ccatcgagcg ggtcaagctg ctgctgcagg
181 tgcagcatgc cagcaagcag atcactgcag ataagcaata caagggcatt atagactgcg
241 tggtccgtat tcccaaggag caggggagtc tgtccttctg gcgcggtaac ctggccaatg
301 tcatcagata cttccccacc caggctctta acttcgcctt caaagataaa tacaagcaga
361 tcttcctggg tggtgtggac aagagaaccc agttttggcg ctactttgca gggaatctgg
421 catcgggtgg tgccgcaggg gccacatccc tgtgttttgt gtaccctctt gattttgccc
481 gtacccgtct agcagctgat gtgggtaaag ctggagctga aagggaattc cgaggcctcg
541 gtgactgcct ggttaagatc tacaaatctg atgggattaa gggcctgtac caaggcttta
601 acgtgtctgt gcagggtatt atcatctacc gagccgccta cttcggtatc tatgacactg
661 caaggggaat gcttccggat cccaagaaca ctcacatcgt catcagctgg atgatcgcac
721 agactgtcac tgctgttgcc gggttgactt cctatccatt tgacaccgtt cgccgccgca
781 tgatgatgca gtcagggcgc aaaggaactg acatcatgta cacaggcacg cttgactgct
841 ggcggaagat tgctcgtgat gaaggaggca aagctttttt caagggtgca tggtccaatg
901 ttctcagagg catgggtggt gcttttgtgc ttgtcttgta tgatgaaatc aagaagtaca
961 cataagttat ttcctaggat ttttccccct gtgaacaggc atgttgtatt ctataacaca
1021 atcttgagca ttcttgacag actcctggct gtcagtttct cagtggcaac tactttactg
1081 gttgaaaatg ggaagcaata atattcatct gaccagtttt cctctaaagc catttccatg
1141 atgatgatga tgggactcaa ttgtattttt tatttcagtc actcctgata aataacaaat
1201 ttggagaaat aaaaatatct aaaat

Target sequence of ANT2 siRNA

Target sequence of ANT2 siRNA-1: gca gau cac ugc aga uaa g

Target sequence of ANT2 siRNA-2: cug aca uca ugt aca cag g

Target sequence of ANT2 siRNA-3: gau ugc ucg uga uga agg a

FIG. 16
[FACS analysis]
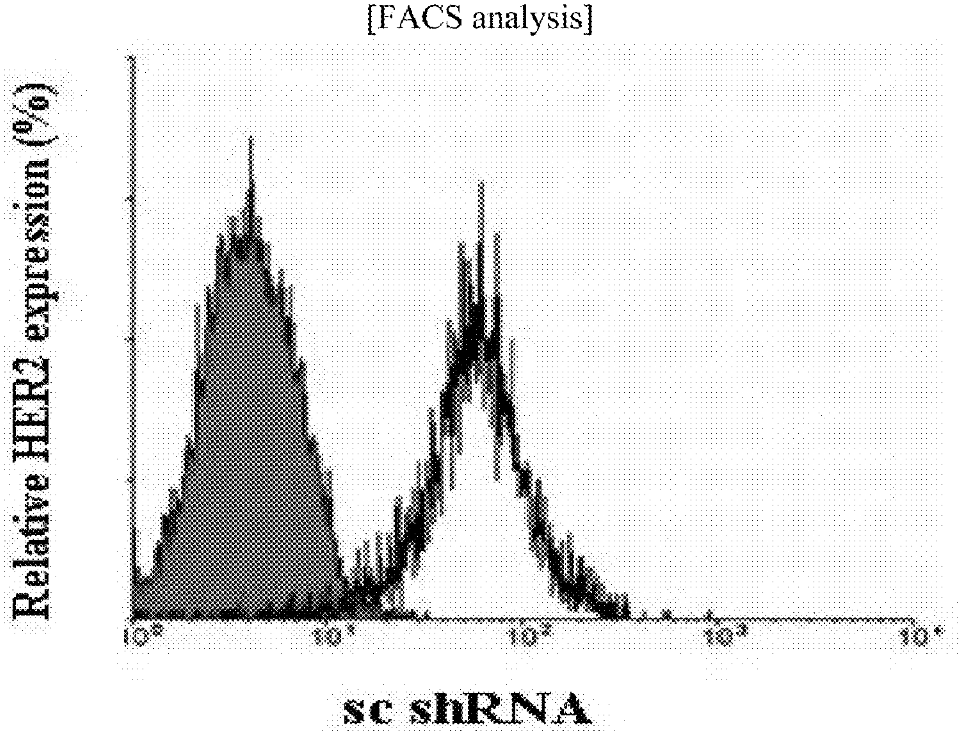
sc shRNA
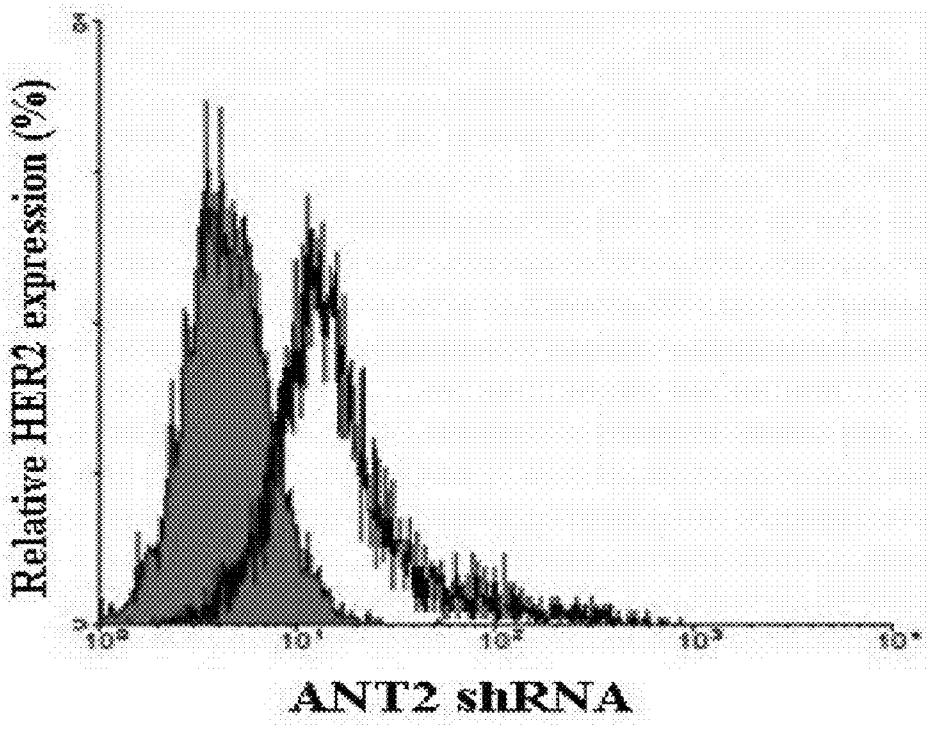
ANT2 shRNA

FIG. 19
A. [RT-PCR]
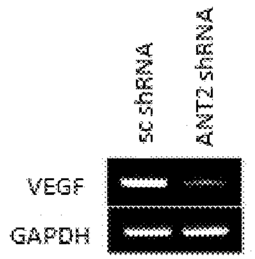
B. [FACS analysis]
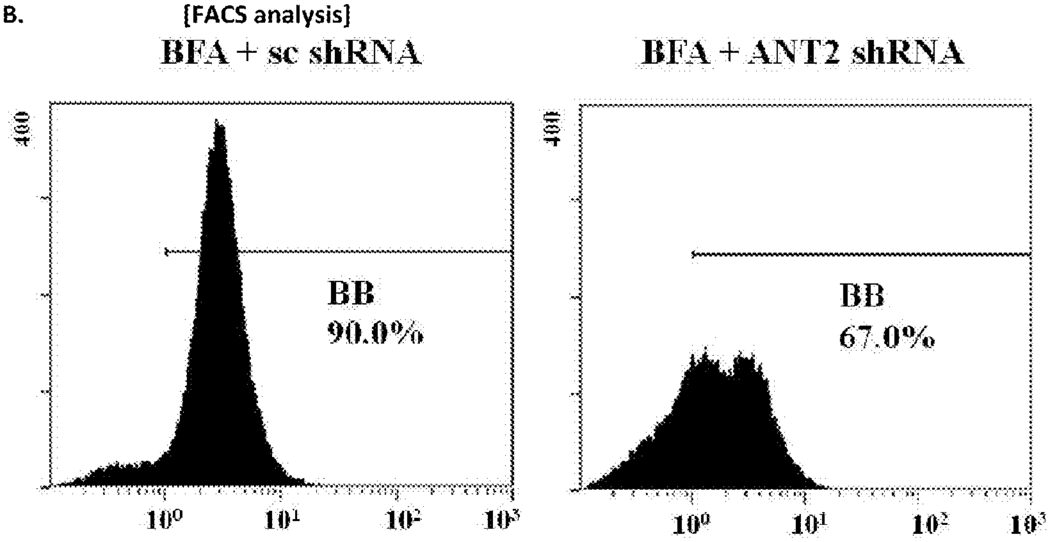
C. [RT-PCR]
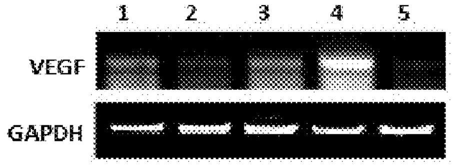
Lane 1 sc sh RNA
Lane 2 ANT2 shRNA
Lane 3 pcDNA3.0
Lane 4 pcDNA3.0-ANT2
Lane 5 PI3K inhibitor (LY294002)

A. [CCK8 assay]

FIG. 24 (con'd)
B. [CCK8 assay]
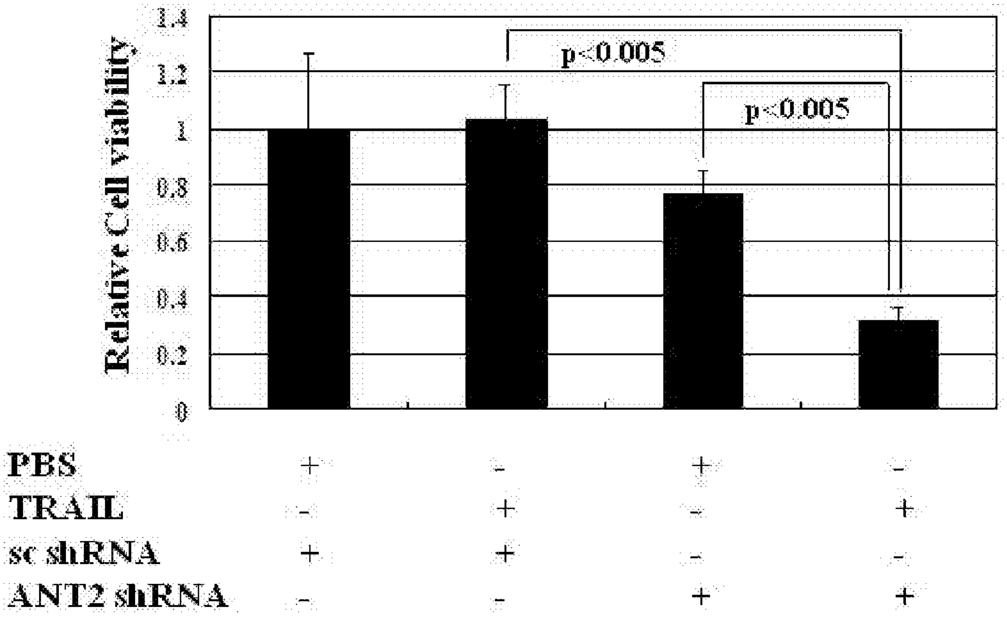
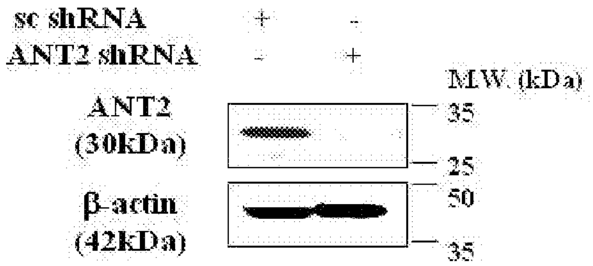

FIG. 24 (con'd)
C.
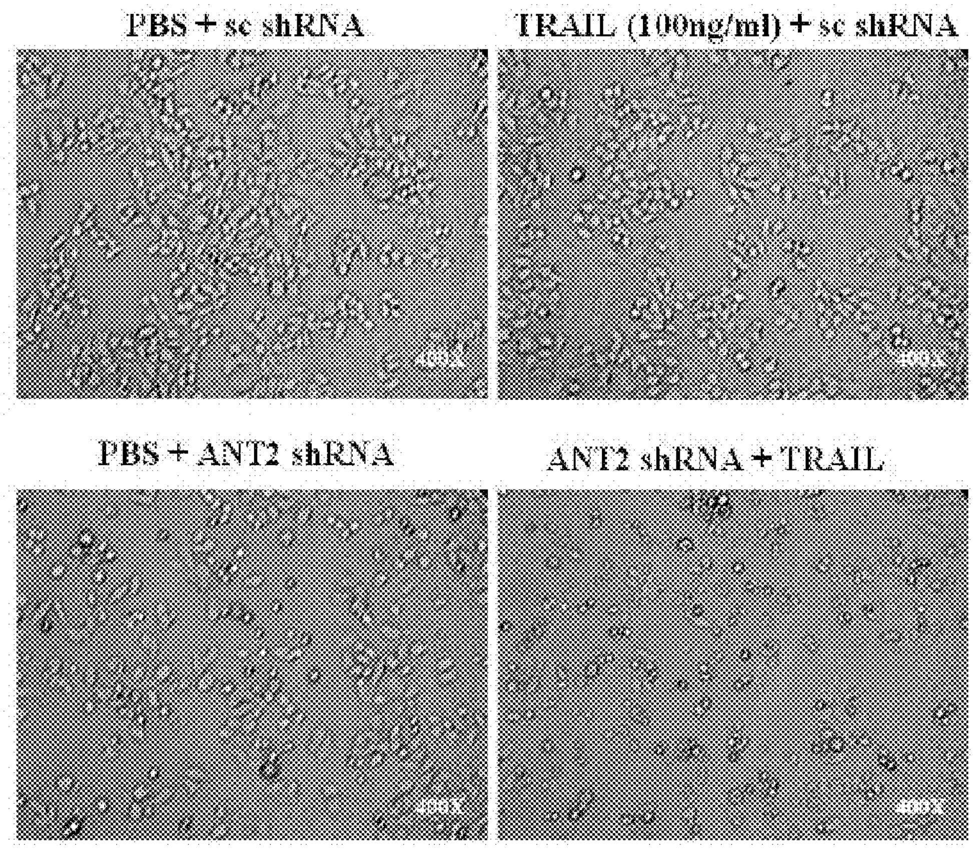

A. [CCK8 assay]

B. [CCK8 assay]

| | | | | | | | | |
|---|---|---|---|---|---|---|---|---|
| PBS | + | - | + | - | + | - | + | - |
| sc shRNA | + | + | - | - | + | + | - | - |
| pcDNA3.1 | + | + | + | + | - | - | - | - |
| TRAIL | - | + | - | + | - | + | - | + |
| ANT2 shRNA | - | - | + | + | - | - | + | + |
| pcDNA3.1-ANT2 | - | - | - | - | + | + | + | + |

C. [Western-blot]

FIG. 26
A. [Western blot]
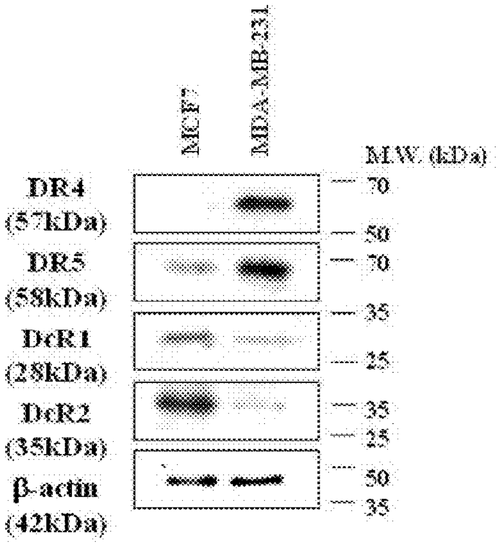
B. [Western blot]
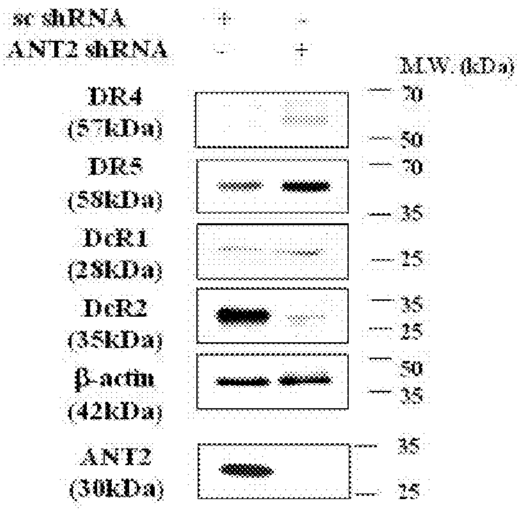
C. [Western blot]
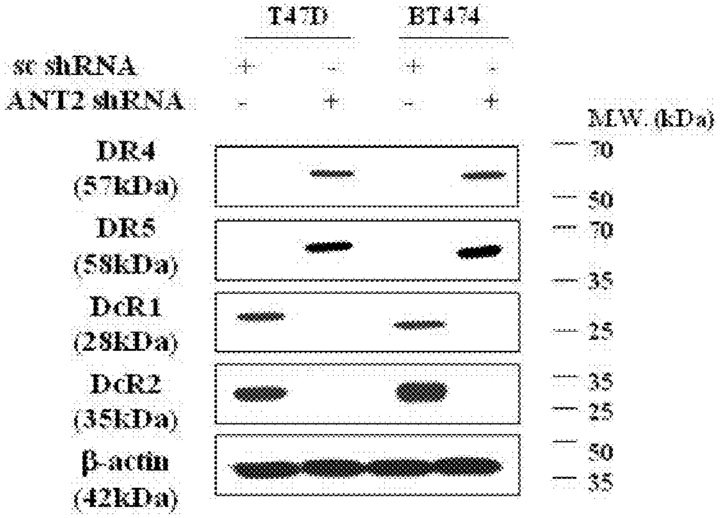

FIG. 27
A. [Western blot]
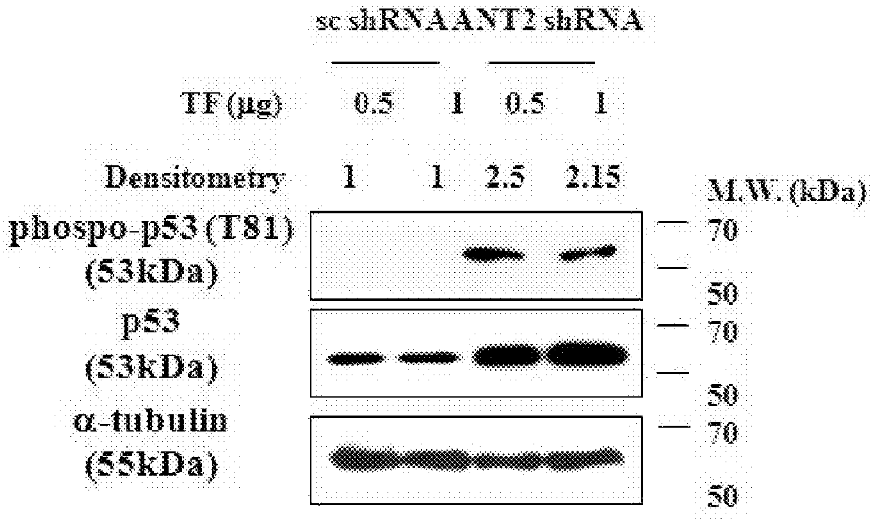
B. [Reporter gene assay]
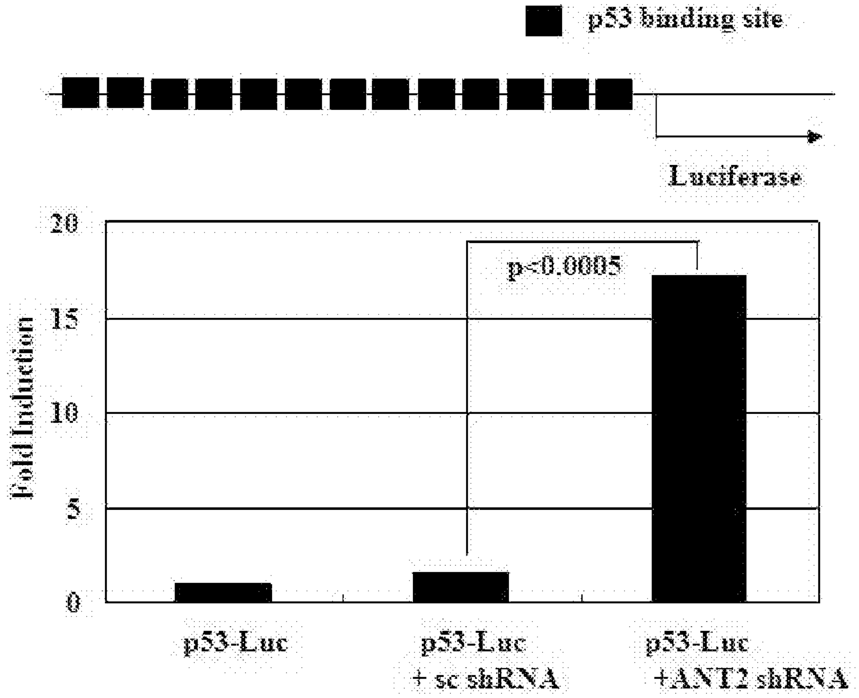

FIG. 29
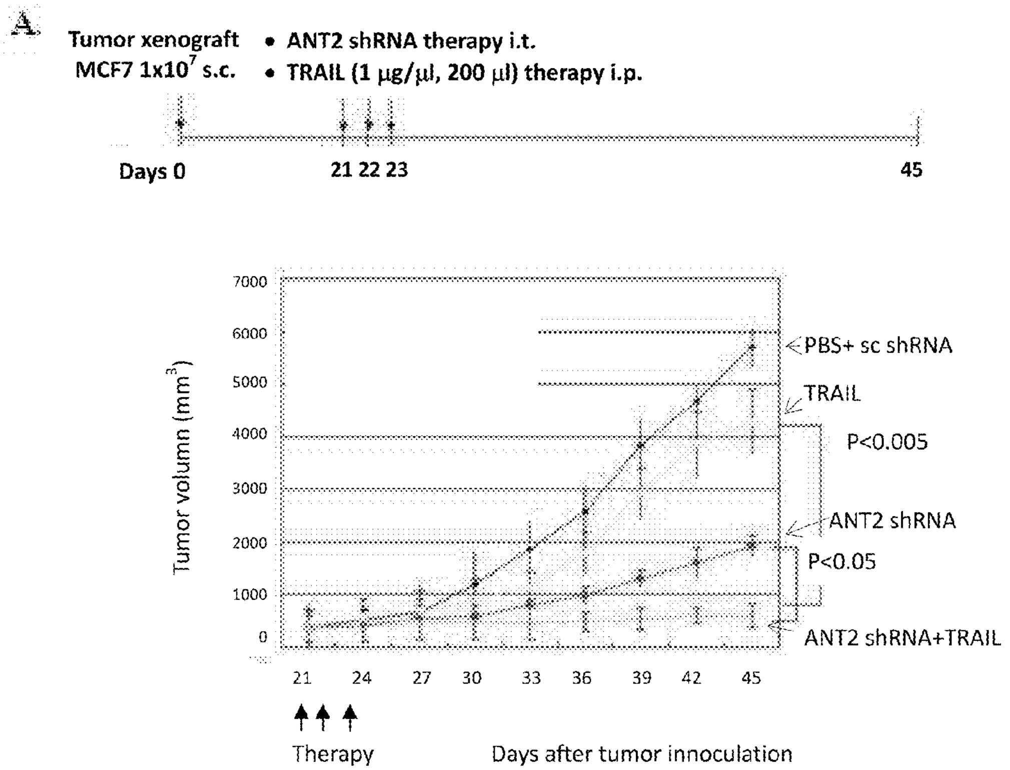
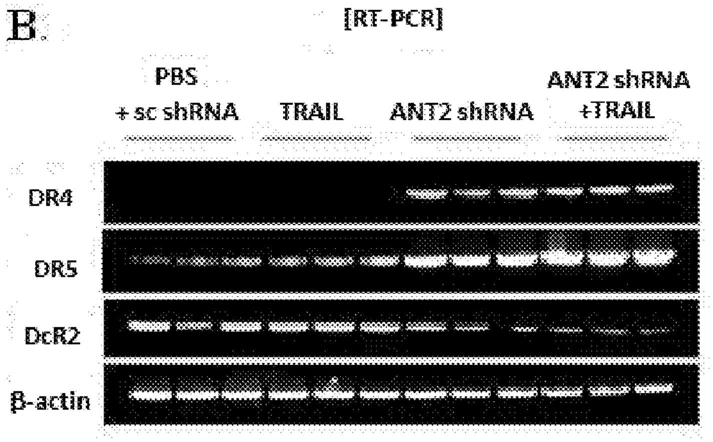

FIG. 32
[Breast Cancer cell lines]
A. CD44/CD24- sorted MDA-MB-231
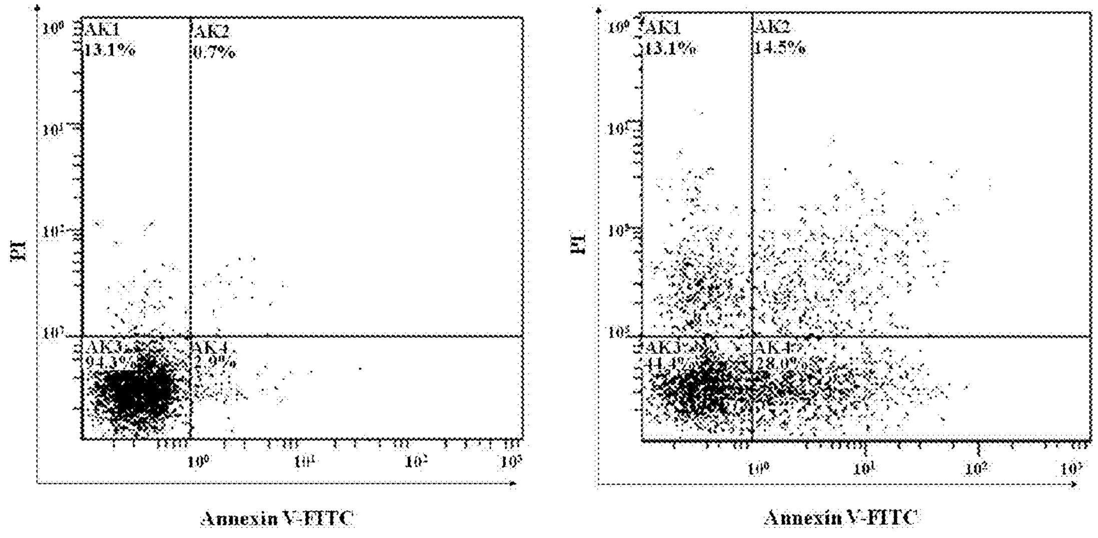
Adeno-sc shRNA Adeno-ANT2 shRNA
B. CD44+/CD24- sorted MCF7
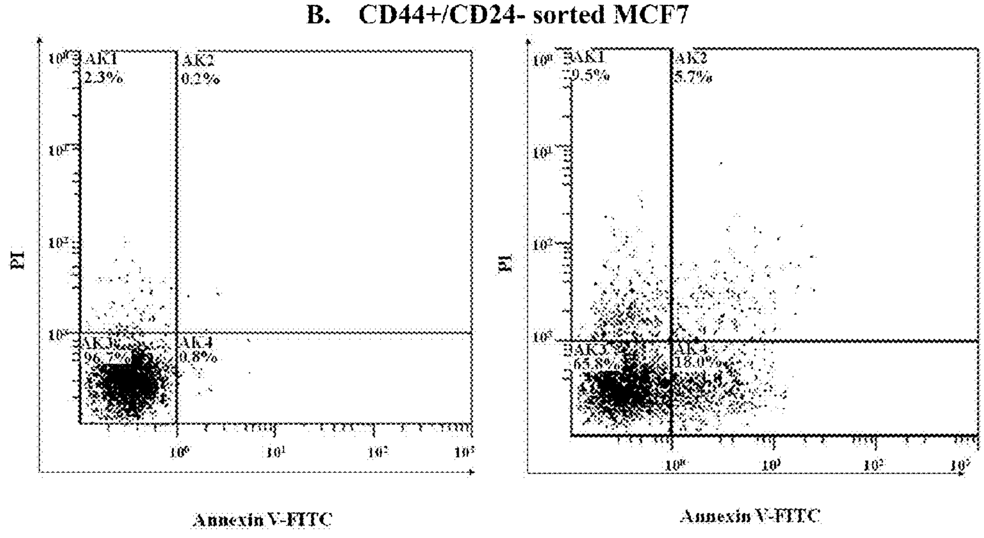
Adeno-sc shRNA Adeno-ANT2 shRNA

[MCF10A: Mesenchymally transdifferentiated breast epithelial cells]

A. MCF10A (sc shRNA): ANT2$^{low}$ No apoptosis

Adeno-sc shRNA  Adeno-ANT2 shRNA

B. MCF10A (E-cad shRNA)

Adeno-sc shRNA  Adeno-ANT2 shRNA

A.

B.

Adeno-sc shRNA

Adeno-ANT2 shRNA

Adeno-sc shRNA

Adeno-ANT2 shRNA

[ABCG2 activity: Hoechst 33342 accumulation]

METHOD FOR TREATING BREAST CANCER USING ADENINE NUCLEOTIDE TRANSLOCATOR 2 (ANT2) SIRNA OR ANT2 SHRNA

CROSS REFERENCE TO RELATED APPLICATIONS

This application claims the benefit of priority under 35 U.S.C. §119 from Korean Patent Application No. 10-2011-0014820 filed Feb. 18, 2011 and is a continuation-in-part of U.S. patent application Ser. No. 12/293,416 filed Sep. 17, 2008, which in turn claims the benefit of Korean Patent Application No. 10-2006-0032823 filed Apr. 11, 2006 through International Application No. PCT/KR2007/001758 filed Apr. 11, 2007, the contents of each of which are incorporated herein by reference.

FIELD OF THE INVENTION

The present invention relates to adenine nucleotide translocator 2 (ANT2) siRNA (small interfering RNA) or ANT2 shRNA (short hairpin RNA) suppressing the expression of ANT2 gene expression and anticancer agent containing the same. Furthermore, the present invention relates to methods for treating breast cancers or stem cells of a breast cancer by treating the same with ANT2 siRNA or ANT2 shRNA. In addition, the invention provides a method for inhibiting metastasis of breast cancer cells with ANT2 siRNA or ANT2 shRNA.

BACKGROUND OF THE INVENTION

Tumor is a result of abnormal, incontrollable and disordered cell proliferation including excessive abnormal cell proliferation. When a tumor exhibits destructive proliferation, infiltration and metastasis, it is classified as a malignant tumor. In particular from the view point of molecular biology, a tumor is considered as a genetic disease caused by mutation of a gene. To treat malignant tumors, three treatment methods which are surgical operation, radiotherapy and chemotherapy have been conducted either separately or together. Particularly, surgical operation is a method to eliminate most of pathogenic tissues, which is thus very effective to remove tumors growing in the breast, colon and skin but not so effective to treat tumors in spine and dispersive tumors.

Radiotherapy has been performed to treat acute inflammatory, benign or malignant tumors, endocrine disorders and allergies, and it has been effective to treat such malignant tumors resulted from abnormal rapid cell division. However, the ratio therapy carries serious side effects such as functional disorder or defect of normal cells, outbreak of cutaneous disorders on the treated area and particularly retardation and anostosis in children.

Chemotherapy is a method to disturb duplication or metabolism of cancer cells, which has been performed to treat breast cancer, lung cancer and testicular tumor. The biggest problem of this treatment method is the side effect carried by systemic chemotherapy. Side effects of such chemotherapy are lethal and thus increase anxiety and fear for the treatment. One of the representative side effects of chemotherapy is dose limiting toxicity (DLT). Mucositis is one of examples of DLT for various anticancer agents (antimetabolic agents such as 5-fluorouracil and methotrexate, and antitumor antibiotics such as doxorubicin). Most cases of side effects require hospitalization or at least need pain killers. So, side effects by chemotherapy and radiotherapy are such as are serious matters for the treatment of cancer patients.

In the meantime, gene therapy is based on the DNA recombination technique, which is the method to insert a therapeutic gene into cancer patient cells to correct gene defect or to endow a novel functions to disordered cells to treat or prevent various genetic diseases caused by mutations diseases, infective of genes, diseases, cancer, autoimmune cardiovascular diseases, etc. More particularly, gene therapy is a method to treat the said diseases by inducing intracellular expressions of normal proteins or therapeutic target proteins by conveying a therapeutic gene into a target organ. Gene therapy has an excellent selectivity, compared with other treatment methods using drugs and can be applied for a long term with improved treatment effect on difficult diseases. To enhance the therapeutic effect of gene therapy, gene transfer technique is essential for the realization of high efficient gene expression in target cells.

A gene carrier is a mediator for the insertion of a therapeutic gene into a target cell. A preferable gene carrier is the one that is not harmful for human, can be mass-produced and has ability to transmit a therapeutic gene effectively and induce constant expression of the therapeutic gene. Thus, gene transfer technique is a key factor for gene therapy and representative gene carriers most wanted for gene therapy so far are exemplified by viral carriers such as adenovirus, adeno-associated virus (AAV), and retrovirus; and non-viral carriers such as liposome and polyethyleneimine.

It is one of the strategies of gene therapy to control tumor cells by using a tumor suppressor gene, a tumor-specific killer virus, a suicide gene and an immunoregulation gene. Particularly, the method using a tumor suppressor gene is to treat cancer by conveying the original form of a tumor suppressor gene such as p53, which is deficient or mutated in many cancer patients. The method using a tumor-specific killer virus is to treat cancer by conveying a virus gene carrier that can be proliferated selectively in tumor cells into cancer patients by taking advantage of the activity of a tumor suppressor gene transformed in cancer tissues. The basic strategy of the above two methods is to kill tumor cells directly. In the meantime, the method using a suicide gene is to induce suicide of tumor cells by inserting sensitive genes such as HSK-TK. The method using an immunoregulation gene is to treat disease indirectly by stimulating T-cell mediated tumor cell recognition by delivering a gene increasing antitumor immune response such as interleukin 12 (IL12), interleukin 4 (IL4), interleukin 7 (IL7), γ-interferon and tumor necrosis factor (TNF) or by inducing apoptosis by interrupting tumor inducing proteins.

In relation to gene therapy among various attempts to treat cancer, the present inventors selected ANT (adenine nucleotide translocator) as a target gene to develop an effective safe anticancer agent.

ANT (adenine nucleotide translocator) is an enzyme found in inner membrane (IM) of mitochondria, which imports ADP from cytoplasm through VDAC (voltage dependent anion channel) of outer membrane (OM) of mitochondria and exports ATP generated in electron transfer chain system into cytoplasm (HLA Vieira, et ale, Cell Death and Differentiation, 7, 1146-1154, 2000).

It is also known that ANT playing a key role in energy metabolism of cells is classified into ANT1, ANT2 and ANT3. Particularly ANT2 exhibits low expression rate in normal cells but is highly expressed in cancer cells or similarly highly proliferated cells, which seems to be closely related to glycolysis under anaerobic condition, so that ANT2 is rising up as a new target for cancer treatment (Chevrollier, A, et al., Med. Sci., 21 (2), 156-161, 2005). However, the previous report only suggested the possibility of application to cancer treatment and in fact there has been no reports saying that ANT2 is a target gene which is effective for cancer treatment.

It has been disclosed recently that double stranded RNA (dsRNA) inserted in animal or plant cells could decompose mRNA corresponding to the dsRNA and thereby inhibit a specific protein synthesis, which is called 'RNA interference' (Sharp, P. A., et al., Genes Dev., 16, 485-490, 2001). At this time, dsRNA is converted into siRNA (small interfering RNA) by an unknown mechanism and decomposes corresponding mRNA. But, when dsRNA having at least 30 nucleotides is used, non-specific reactions might nullify protein synthesis interruption or at least make the interruption inefficient (Hunter, T. et al., J. Biol. Chem., 250, 409-417, 1975; and Robertson, H. D. and Mathews, M. B., Biochemie., 78, 909-914, 1996). To overcome the above problem, a new technique has been developed to synthesize double stranded siRNA composed of 21 oligomers and to insert the siRNA into mammalian cells to decompose corresponding mRNA to interrupt a specific target protein synthesis (Hutvagner, H. D. et al., Science, 29,834-838, 2001).

In vivo/in vitro experiments have been vigorously performed as follows in order to treat diseases including cancer by synthesizing double stranded siRNA composed of 21 oligomers. For example, [β-catenin that is involved in rapid growth of cancer cells was effectively eliminated from cultured colon cancer cells and mouse colon cancer models by using synthetic β-catenin siRNA (Verma, U. N., et al., Clinical Cancer Res., 9, 1291-1300, 2003; and Annick, H. B., et al., PNAS USA, 99, 14849-14854, 2002).

It was also reported that when multidrug resistance 1 (MDR1) siRNA synthetic oligomer produced to overcome drug resistance of cancer cells, which has been a barrier for chemotherapy, was inserted in MDR1 expressing cells, MDR1 protein synthesis was blocked (Wu, H. et al., Cancer Res., 63, 1515-1519, 2003). When cycline E siRNA synthetic oligomer was treated to cycline E over-expressing liver cancer cells, the proliferation of cultured liver cancer cells and/or liver cancer cells transplanted into a mouse was suppressed (Kaiyi, L. et al., Cancer Res., 63, 3593-3597, 2003).

The above results indicate that siRNA that is overexpressed in cancer cells and at the same time able to interrupt selectively a protein involved in rapid growth of cancer cells can be developed as an effective anticancer agent. Nevertheless, synthetic siRNA allegedly has disadvantages as follows; synthetic siRNA oligomer requires high costs for its synthesis, exhibits low intracellular transmission rate, induces non-specific reaction that might induce cytotoxicity and has short half-life in vivo which suggests that the effect is not constant and thereby the injection has to be repeated. So, in vivo application of synthetic siRNA is limited.

Both viral and non-viral gene carriers that can express siRNA in cells are expected to overcome the said disadvantages of synthetic siRNA oligomer greatly.

The present inventors observed that ANT2 siRNA that was believed to interrupt ANT2 protein synthesis could effectively inhibited the growth of cancer cells where ANT2 was over-expressed, and completed this invention by confirming that ANT2 siRNA can be used as an anticancer agent.

SUMMARY OF THE INVENTION

The present invention provides a method treating cancers and stem cells of cancers using an anticancer agent that is able to inhibit the proliferation of cancer cells especially over-expressing ANT2 which is closely involved in the development and progress of cancer. More specifically the present invention provides a method for treating breast cancers wherein administering an effective amount of a pharmaceutical composition containing adenine nucleotide translocator 2 (ANT2) small interfering RNA (siRNA) or adenine nucleotide translocator 2 (ANT2) short hairpin RNA (shRNA) as an active ingredient to a subject with cancer. Furthermore, the present invention provides a method for treating stem cells of breast cancers by treating the stem cells of breast cancers with a composition comprising adenine nucleotide translocator 2 (ANT2) small interfering RNA (siRNA) or adenine nucleotide translocator 2 (ANT2) short hairpin RNA (shRNA), in vivo or in vitro.

In further embodiment, the present invention provides a method of inhibiting metastasis of breast cancer cells by administering an effective amount of a pharmaceutical composition comprising adenine nucleotide translocator 2 (ANT2) small interfering RNA (siRNA) or adenine nucleotide translocator 2 (ANT2) short hairpin RNA (shRNA) as an active ingredient to a subject having the breast cancers.

BRIEF DESCRIPTION OF THE DRAWINGS

The application of the preferred embodiments of the present invention is best understood with reference to the accompanying drawings, wherein:

FIG. 3A is a diagram showing the result of RT-PCR exhibiting the expressions of ANT1 and ANT2 mRNAs in breast cancer cells (MDA-MB-231) and peripheral blood mononuclear cells (PBMC) and FIG. 3B is a diagram showing the result of RT-PCR, which is that ANT2 siRNA expression vector of the present invention reduces ANT2 mRNA expression in breast cancer cells: Scrambled siRNA was used as a negative control.

FIG. 12A is a graph showing the anticancer effect of ANT2 siRNA or the negative control, scrambled siRNA expression vector, which was investigated by measuring the size of a tumor in a nude mouse after transplantation of breast cancer cells (MDA-MB-231) containing ANT2 siRNA of the invention or the negative scrambled siRNA expression vector under the right femoral region of balb/c nude mouse, and FIG. 12B is a graph showing that ANT2 siRNA of the invention or the negative control scrambled siRNA expression vector was introduced into breast cancer cells (MDA-MB-231), which were then transplanted under the right femoral region of balb/c nude mouse, followed by measuring the weight of a tumor separated by dissection on the 60th day from the transplantation.

FIG. 15 is a diagram showing the target sequence of ANT2 siRNA of the invention screened among human ANT2 (Genebank Accession No. NM__001152 and SEQ ID NO: 1) nucleotide sequences:

Target sequence of ANT2 siRNA-1 (SEQ ID NO: 16);

Target sequence of ANT2 siRNA-2 (SEQ ID NO: 14); and

Target sequence of ANT2 siRNA-3 (SEQ ID NO: 15).

FIG. 16 is a FACS analysis which shows that when the breast cancer cell line SK-BR3 overexpressing HER2/neu is transfected with ANT2 shRNA, its HER2/neu expression level is reduced.

FIG. 17A is a diagram showing the result of Western-blot, wherein when the breast cancer cell line SK-BR3 overexpressing HER2/neu is transfected with ANT2 shRNA, the introduced ANT2 shRNA promotes the degradation of HSP90 resulting in the reduction of the expression level of HSP90.

FIG. 17B is a diagram showing the result of Western-blot, wherein when the breast cancer cell line SK-BR3 overexpressing HER2/neu is transfected with ANT2 shRNA, its HER2 expression level is reduced.

Figure 18:
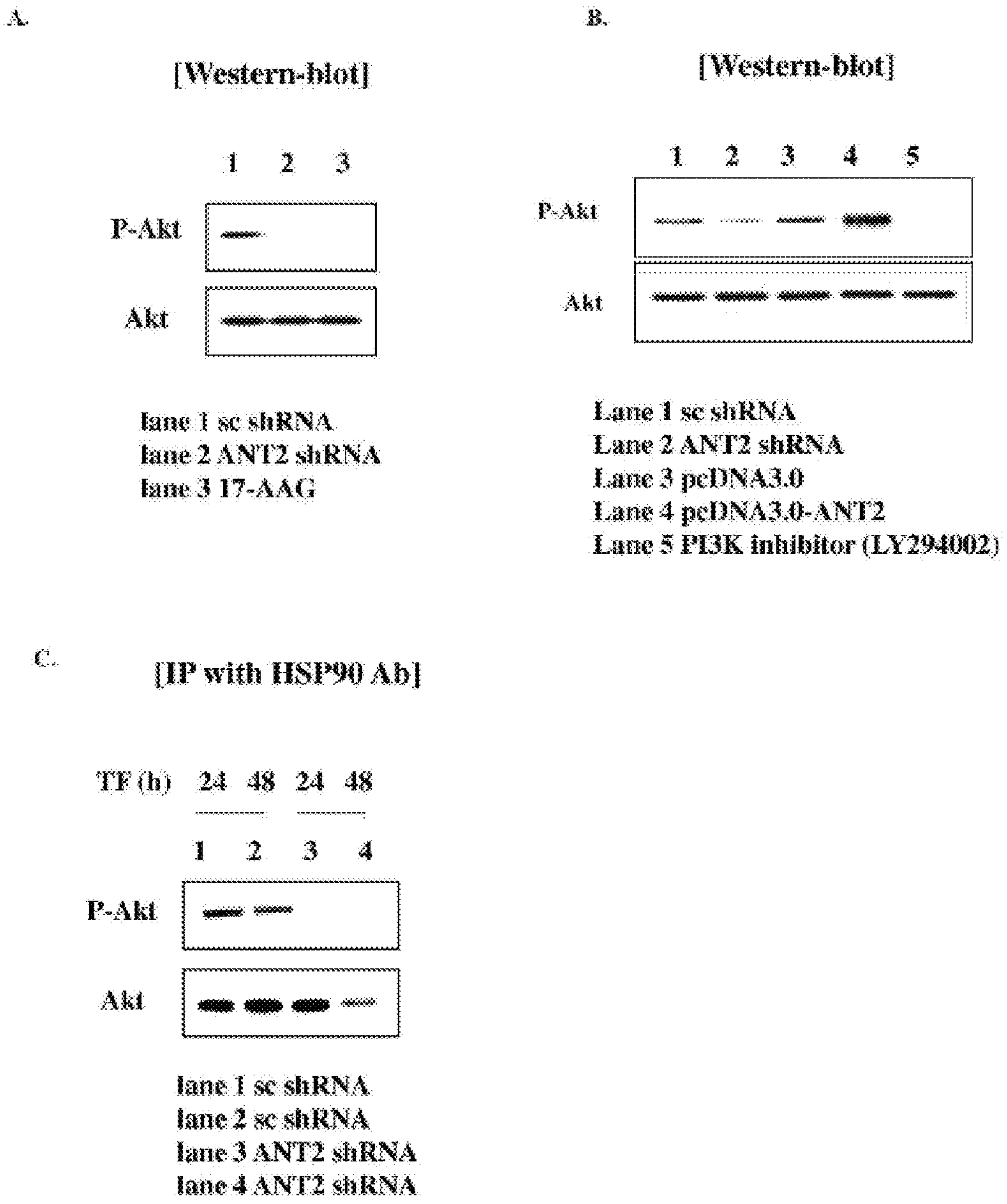

FIG. 18A is a diagram showing the result of Western-blot, wherein when the breast cancer cell line SK-BR3 overexpressing HER2/neu is transfected with ANT2 shRNA, its Akt activity is reduced.

FIG. 18B is a diagram showing the result of Western-blot, wherein when the breast cancer cell line SK-BR3 overexpressing HER2/neu is decreased in Akt activity when transfected with ANT2 shRNA, and recovers its Akt activity by ANT2 overexpression.

FIG. 18C is a diagram showing the result of Western blotting, wherein when the breast cancer cell line SK-BR3 overexpressing HER2/neu is transfected with ANT2 shRNA, HSP90 weakly interacts with Akt and the activity of Akt is reduced.

FIG. 19A is a diagram showing the result of RT-PCR, wherein when the breast cancer cell line SK-BR3 overexpressing HER2/neu is transfected with ANT2 shRNA, there is a decrease in the mRNA expression level of VEGF.

FIG. 19B is a diagram showing the result of FACS analysis, wherein when the breast cancer cell line SK-BR3 overexpressing HER2/neu is transfected with ANT2 shRNA, there is a decrease in the intracellular level of VEGF.

FIG. 19C is a diagram showing the result of RT-PCR, wherein when the breast cancer cell line SK-BR3 overexpressing HER2/neu is decreased in the mRNA expression level of VEGF when transfected with ANT2 shRNA, and recovers VEGF mRNA levels by the overexpression of ANT2.

Figure 20:
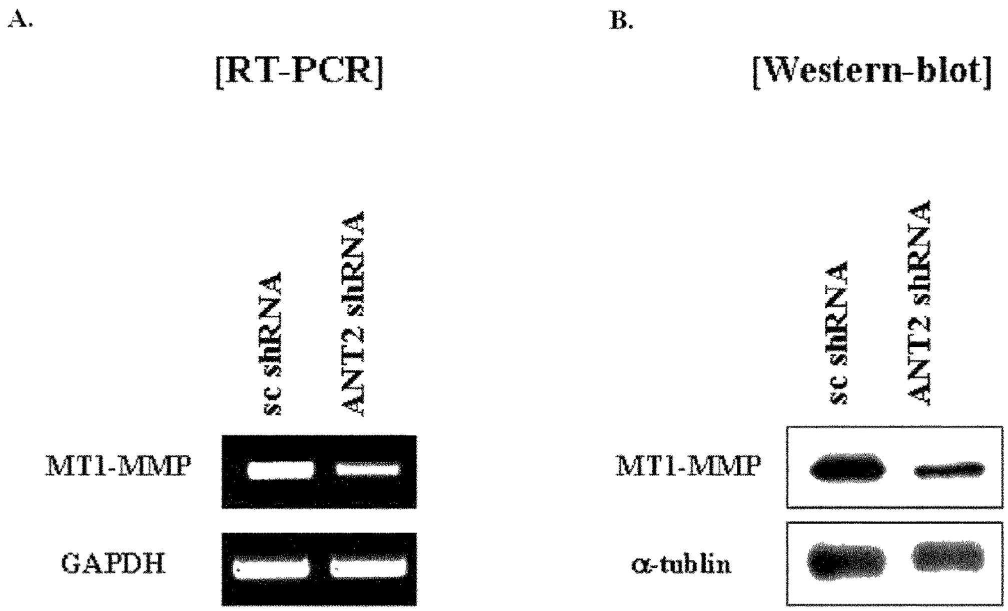

FIG. 20A is a diagram showing the result of RT-PCR, wherein when the breast cancer cell line SK-BR3 overexpressing HER2/neu is transfected with ANT2 shRNA, there is a decrease in the mRNA expression level of MT1-MMP.

FIG. 20B is a diagram showing the result of Western-blot, wherein when the breast cancer cell line SK-BR3 overexpressing HER2/neu is transfected with ANT2 shRNA, there is a decrease in the protein expression level of MT1-MMP.

Figure 21:
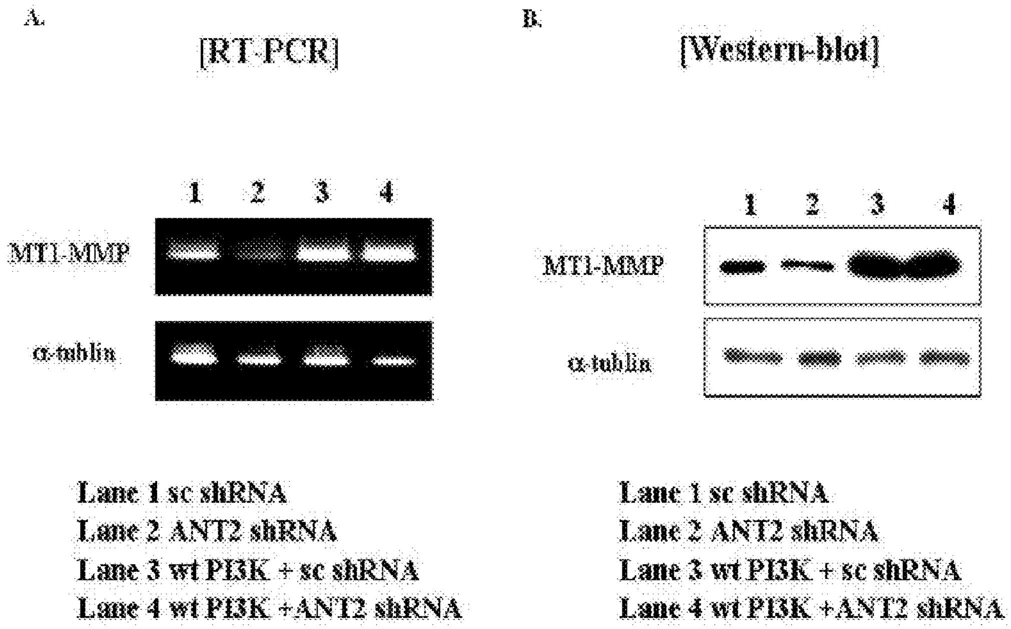

FIG. 21A is a diagram showing the result of RT-PCR, wherein the breast cancer cell line SK-BR3 overexpressing HER2/neu is decreased in the mRNA expression level of MT1-MMP when transfected with ANT2 shRNA, and recovers the mRNA expression level by the overexpression of PI3K.

FIG. 21B is a diagram showing the result of RT-PCR, wherein the breast cancer cell line SK-BR3 overexpressing HER2/neu is decreased in the protein expression level of MT1-MMP when transfected with ANT2 shRNA, and recovers the protein expression level by the overexpression of PI3K.

Figure 22:
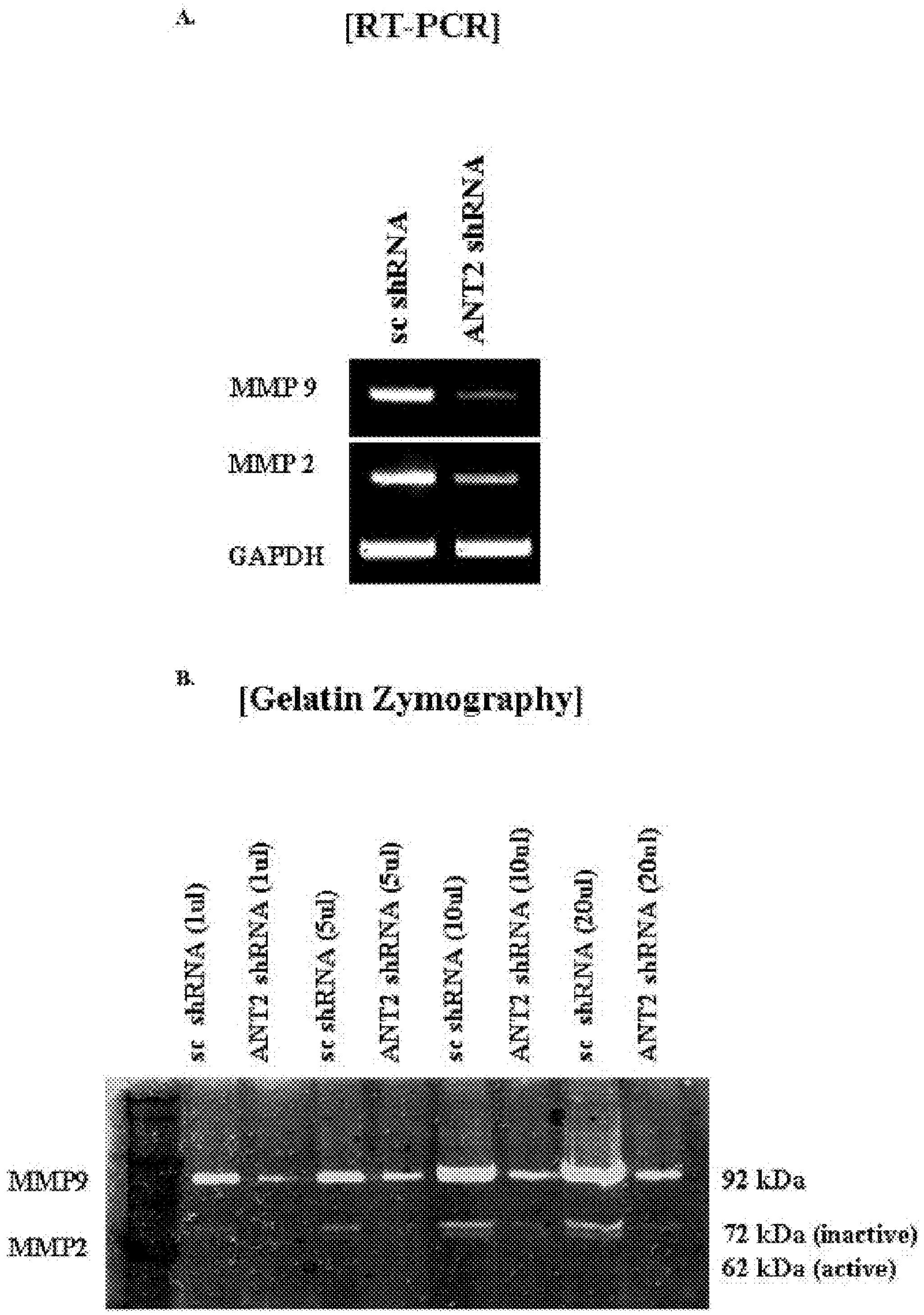

FIG. 22A is a diagram showing the result of RT-PCR, wherein when the breast cancer cell line SK-BR3 overexpressing HER2/neu is transfected with ANT2 shRNA, there is a decrease in the mRNA expression level of both MMP2 and MMP9.

FIG. 22B is a diagram showing the result of Gelatin Zymography, wherein when the breast cancer cell line SK-BR3 overexpressing HER2/neu is transfected with ANT2 shRNA, there is a decrease in the activity of both MMP2 and MMP9.

FIG. 23A shows a result of Matrigel invasion assay, wherein when the breast cancer cell line SK-BR3 overexpressing HER2/neu is transfected with ANT2 shRNA, its invasion ability is reduced.

FIG. 23B shows a result of Transwell migration assay, wherein when the breast cancer cell line SK-BR3 overexpressing HER2/neu is transfected with ANT2 shRNA, its migration ability is reduced.

Figure 24:
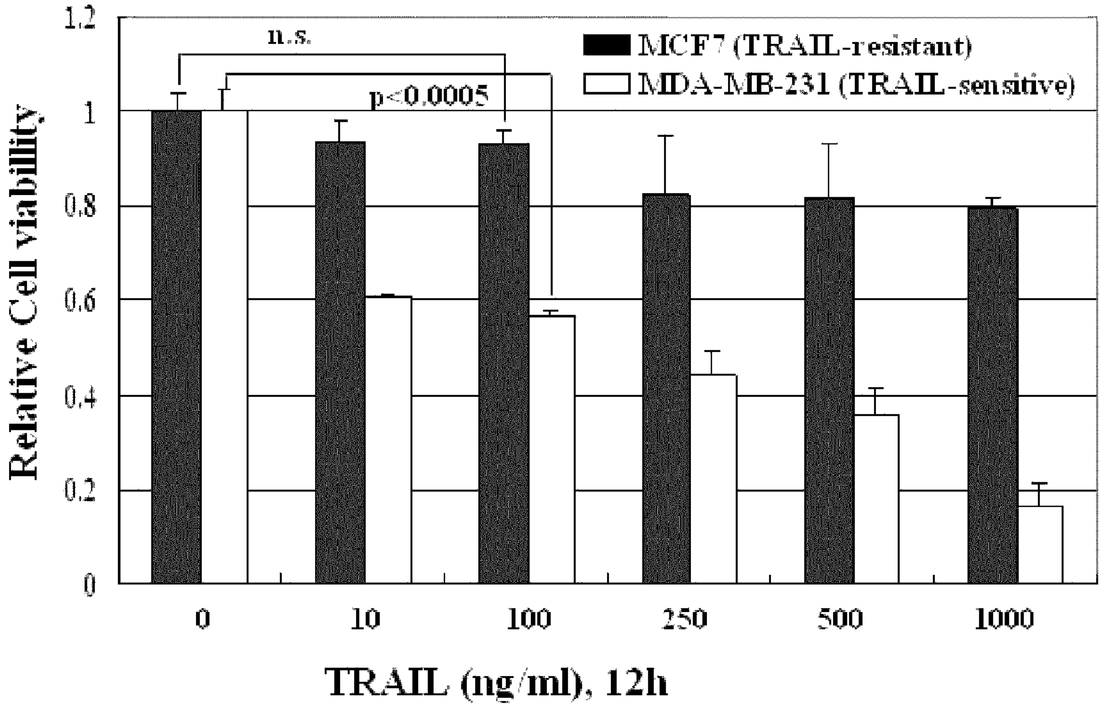

FIG. 24A shows a result of CCK8 assay, wherein the resistance of MCF7 and the sensitivity (apoptosis) of MDA-MB-231 to TRAIL.

FIG. 24B shows a result of CCK8 assay and a diagram showing the result of Western blotting, wherein while the breast cancer cell line MCF7 is resistant to TRAIL, the introduction of ANT2 shRNA induces the sensitivity of MCF7 to TRAIL (apoptosis).

FIG. 24C shows a result of CCK8 assay, wherein while the breast cancer cell line MCF7 is resistant to TRAIL, the introduction of ANT2 shRNA induces the cells to undergo apoptosis as observed in cell photographs.

Figure 25:
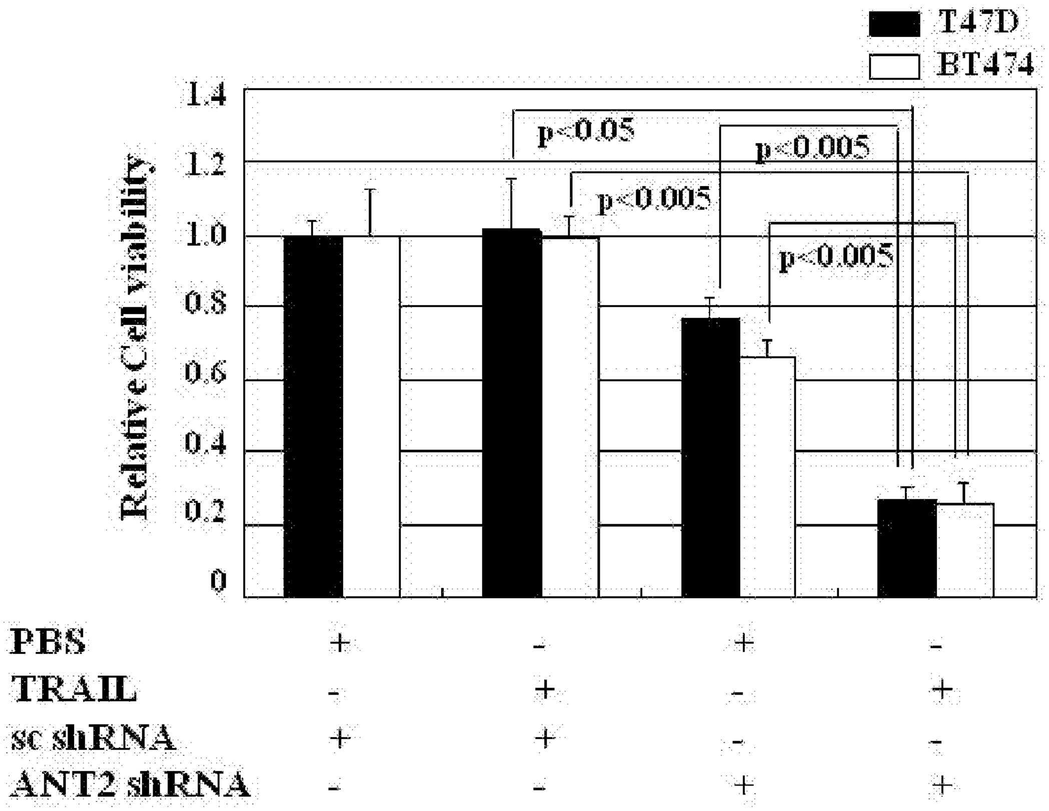
Figure 25:
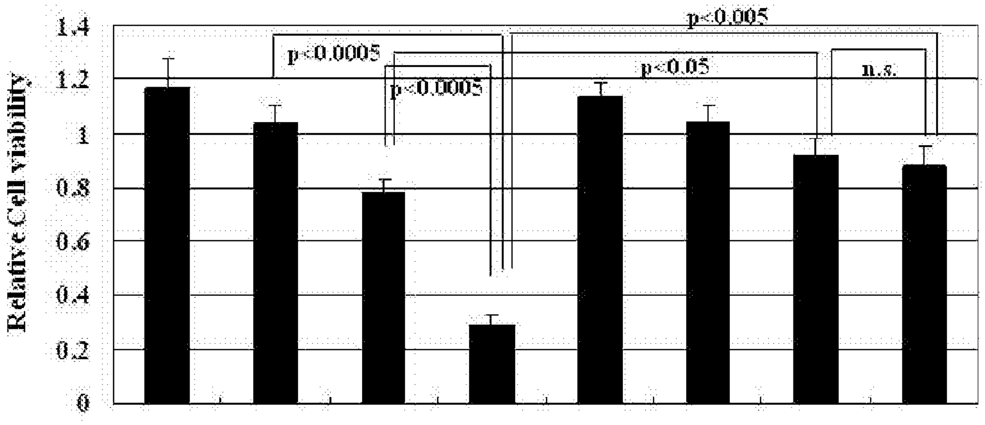
Figure 25:
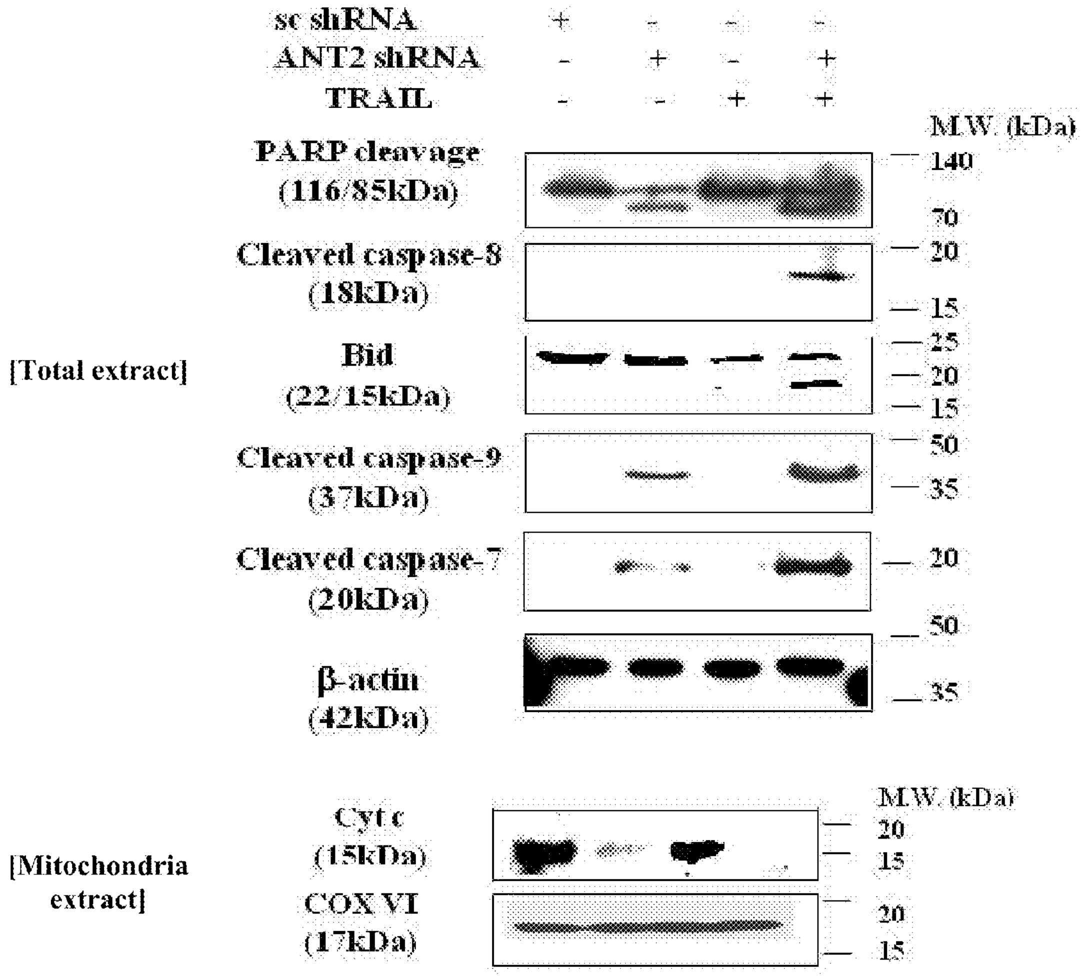

FIG. 25A shows a result of CCK8 assay, wherein that while the breast cancer cell lines T47D and BT474 are resistant to TRAIL, the introduction of ANT2 shRNA effectively induces the cells to undergo apoptosis.

FIG. 25B shows a result of CCK8 assay, wherein while the breast cancer cell line MCF7 is resistant to TRAIL, the introduction of ANT2 shRNA makes the cells highly sensitive to TRAIL (apoptosis) and the overexpression of ANT2 by transfection with an ANT2 expression vector eliminates the apoptotic effect of ANT2 shRNA.

FIG. 25C is a diagram showing the result of Western-blot, wherein the breast cancer cell lines T47D and BT474, resistant to TRAIL, are induced to undergo TRAIL-mediated apoptosis when transfected with ANT2 shRNA, with the concomitant accompaniment of events including the cleavage of caspase-8/9/7, bid truncation, and increased release of cytochrome c due to mitochondrial destruction.

FIG. 26A is a diagram showing the result of Western-blot, wherein the breast cancer cell line MCF7, resistant to TRAIL, is low in the expression level of the TRAIL receptors DR4 and DR5 and high in the expression level of the decoy receptors DcR1 and DcR2, which interfere with the TRAIL signaling pathway and that the breast cancer cell line MDA-MB-231, sensitive to TRAIL, is high in the expression level of the TRAIL receptors DR4 and DR5 and low in the expression level of the decoy receptors DcR1 and DcR2.

FIG. 26B is a diagram showing the result of Western-blot, wherein while the breast cancer cell line MCF7, resistant to TRAIL, is low in the expression level of the TRAIL receptors DR4 and DR5 and high in the expression level of the decoy receptors DcR1 and DcR2, the introduction of ANT2 shRNA increases the expression of DR5 and decreases the expression of DcR2.

FIG. 26C is a diagram showing the result of Western-blot, wherein while the breast cancer cell line MDA-MB-231, sensitive to TRAIL, is low in the expression level of the TRAIL receptors DR4 and DR5 and high in the expression level of the decoy receptors DcR1 and DcR2, the introduction of ANT2 shRNA increases the expression of DR5 and decreases the expression of DcR2.

Figure 27:
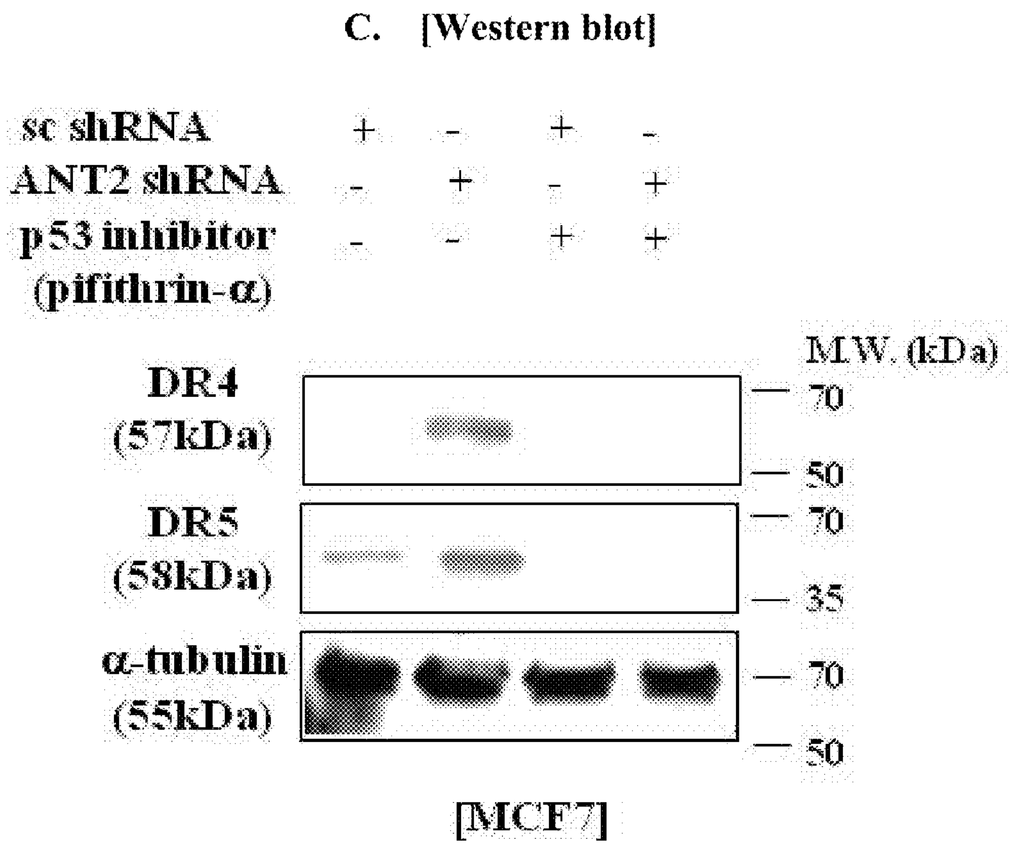

FIG. 27A is a diagram showing the result of Western-blot, wherein the breast cancer cell line MCF7, resistant to TRAIL, is increased in the expression and phosphorylation/activation of p53 protein when transfected with ANT2 shRNA.

FIG. 27B shows the result of Reporter gene assay, wherein the breast cancer cell line MCF7, resistant to TRAIL, is increased in the transcriptional activity of p53 protein when transfected with ANT2 shRNA.

FIG. 27C is a diagram showing the result of Western-blot, wherein the breast cancer cell line MCF7, resistant to TRAIL, is increased in the expression level of the TRAIL receptors DR4 and DR5 when transfected with ANT2 shRNA, indicating that the increased expression is attributed to the activation of p53.

Figure 28:
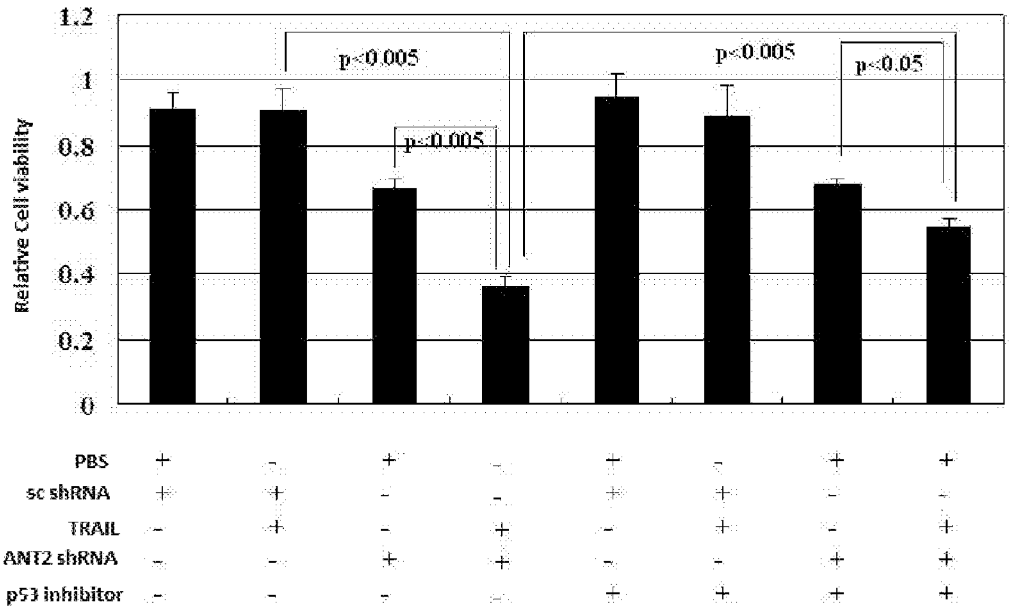

FIG. 28 shows a result of CCK8 assay, wherein the breast cancer cell line MCF7, resistant to TRAIL, is increased in sensitivity to TRAIL when transfected with ANT2 shRNA, indicating that the increased sensitivity is attributed to the activation of p53.

FIG. 29A shows in vivo antitumor efficacy of ANT2 shRNA, wherein after the breast cancer cell line MCF7 is transplanted to immunodeficient Balb/c nude mice, the growth of the resulting tumor was slightly suppressed by treatment with TRAIL alone, moderately by treatment with ANT2 shRNA alone, and greatly by treatment with a combination of TRAIL and ANT2 shRNA.

FIG. 29B is a diagram showing the result of RT-PCR, wherein after the breast cancer cell line MCF7 is transplanted to immunodeficient Balb/c nude mice, the growth of the resulting tumor was greatly suppressed by treatment with a combination of TRAIL and ANT2 shRNA and the tumor increased in the expression level of the TRAIL receptors DR4 and DR5.

FIG. 30A is a diagram showing the result of RT-PCR, wherein both the progenitor cells (CD44+/CD24−) sorted from the breast cancer cell lines MCF7 and MDA-MB-231 and unsorted cells are found to express high levels of ANT2 as measured by RT-PCR.

FIG. 30B is a diagram showing the result of Real time RT-PCR (RT-qPCR), wherein both the progenitor cells (CD44+/CD24−) sorted from the breast cancer cell lines MCF7 and MDA-MB-231 and unsorted cells are found to express high levels of ANT2 as measured by real-time RT-qPCR.

Figure 31:
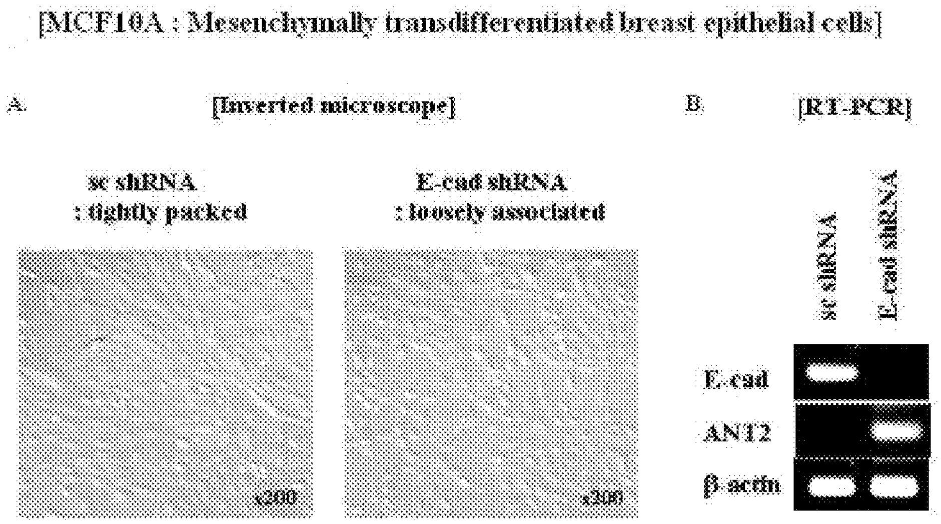

FIG. 31A is an image of inverted microscope showing the result of MCF10A, mesenchymally transdifferentiated breast epithelial cells treated with shRNA, wherein a morphological change when the normal breast epithelial cell line MCF10A is mesenchymally transdifferentiated by transfection with E-cadherin shRNA.

FIG. 31B is a diagram of the result of RT-PCR, wherein when the normal breast epithelial cell line MCF10A is mesenchymally transdifferentiated by transfection with E-cadherin shRNA, the cells are decreased in the expression level of E-cadherin and increased in the expression level of ANT2.

FIG. 32A is a diagram of the result of FACS using double staining with Annexin V and propidium iodide (PI), wherein when the progenitor cells (CD44+/CD24−) isolated from the breast cancer cell line MDA-MB-231 are transfected with ANT2 shRNA, they are effectively induced to undergo apoptosis.

FIG. 32B is a diagram of the result of FACS using double staining with Annexin V and propidium iodide (PI), wherein the progenitor cells (CD44+/CD24−) isolated from the breast cancer cell line MCF7 are transfected with ANT2 shRNA, the progenitor cells are effectively induced to undergo apoptosis.

FIG. 33A is a diagram of the result of FACS using double staining with Annexin V and propidium iodide (PI) in MCF10A, mesenchymally transdifferentiated breast epithelial cells treated with sc shRNA, wherein when the normal breast epithelial cell line MCF10A is transfected with ANT2 shRNA, breast epithelial cell line is not induced to undergo apoptosis.

FIG. 33B is a diagram of the result of FACS using double staining with Annexin V and propidium iodide (PI) in MCF10A, mesenchymally transdifferentiated breast epithelial cells treated with E-cad shRNA, when the normal breast epithelial cell line MCF10A is mesenchymally transdifferentiated by transfection with E-cadherin shRNA, the introduction of ANT2 shRNA can effectively induce apoptosis.

Figure 34:
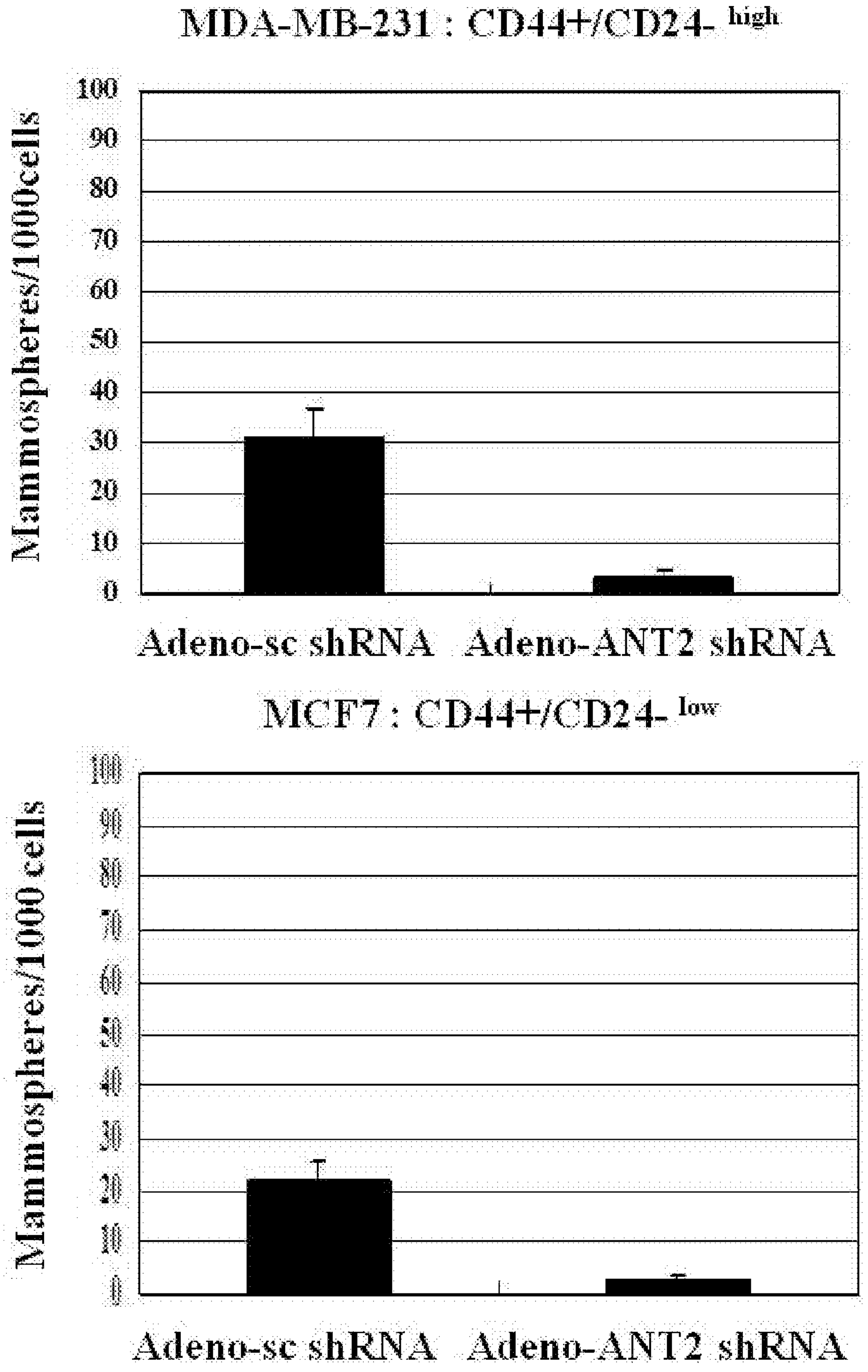
Figure 34:
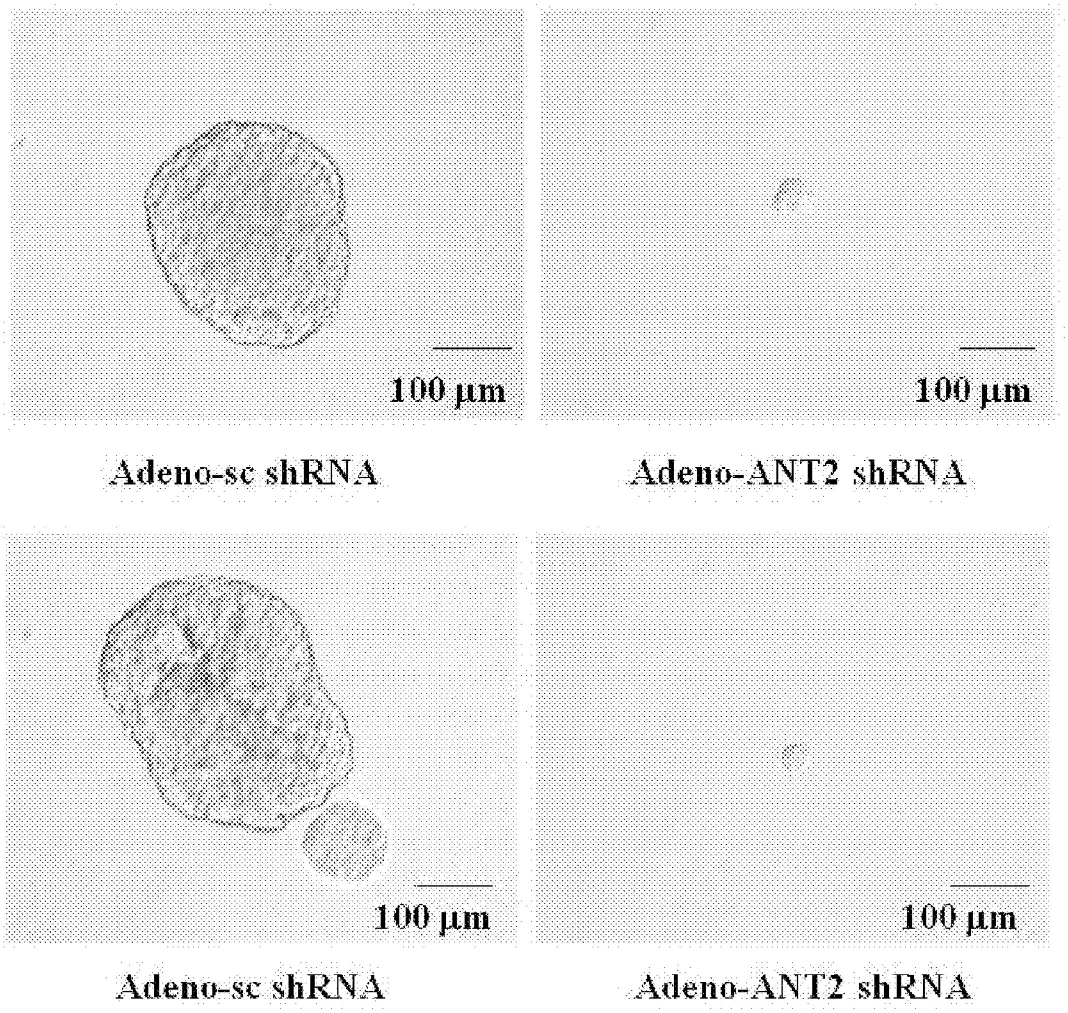

FIG. 34A shows a result of mammosphere assay, wherein MDA-MB-231 with a high proportion of the breast cancer progenitor cells (CD44+/CD24−) and MCF7 with a low proportion of the breast cancer progenitor cells (CD44+/CD24−) show high and low abilities to form cell masses, respectively, and that the ability to form cell masses is reduced in both the cells by the transfection with ANT2 shRNA.

FIG. 34B are of microphotographs of cells showing that MDA-MB-231 with a high proportion of the breast cancer progenitor cells (CD44+/CD24−) and MCF7 with a low proportion of the breast cancer progenitor cells (CD44+/CD24−) show high and low abilities to form cell masses, respectively, and that the ability to form cell masses is reduced in both the cells by the transfection with ANT2 shRNA.

Figure 35:
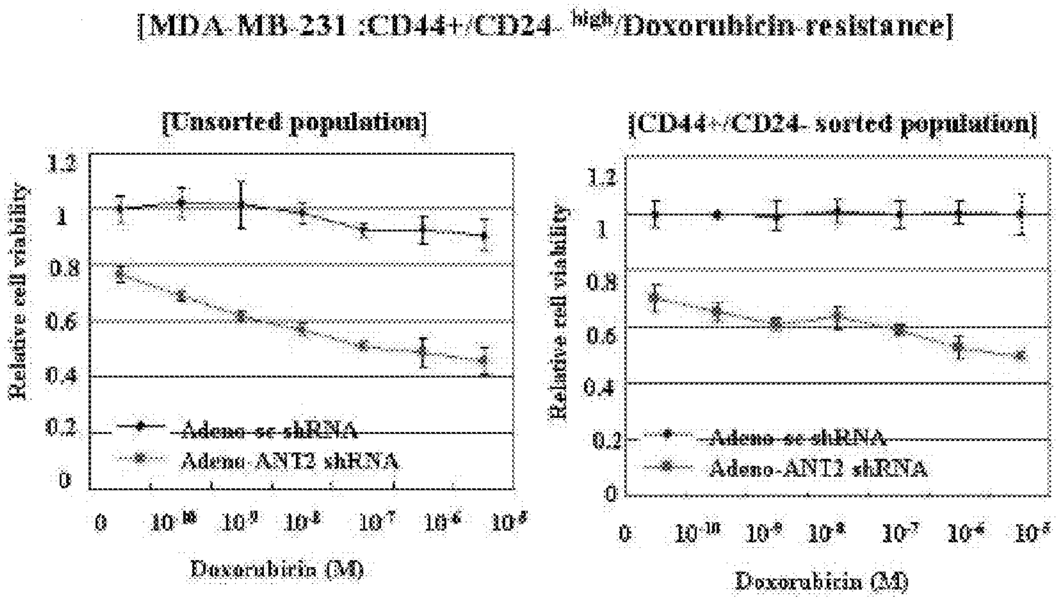

FIG. 35 shows the result of high doxorubicin resistance breast cancer cell lines, MA-MB-231 treated with ANT2 shRNA, wherein while MDA-MB-231 with a high proportion of the breast cancer progenitor cells (CD44+/CD24−) is highly resistant to doxorubicin, the introduction of ANT2 shRNA makes the cells, whether sorted for CD44+/CD24− cells or unsorted, sensitive to doxorubicin.

Figure 36:
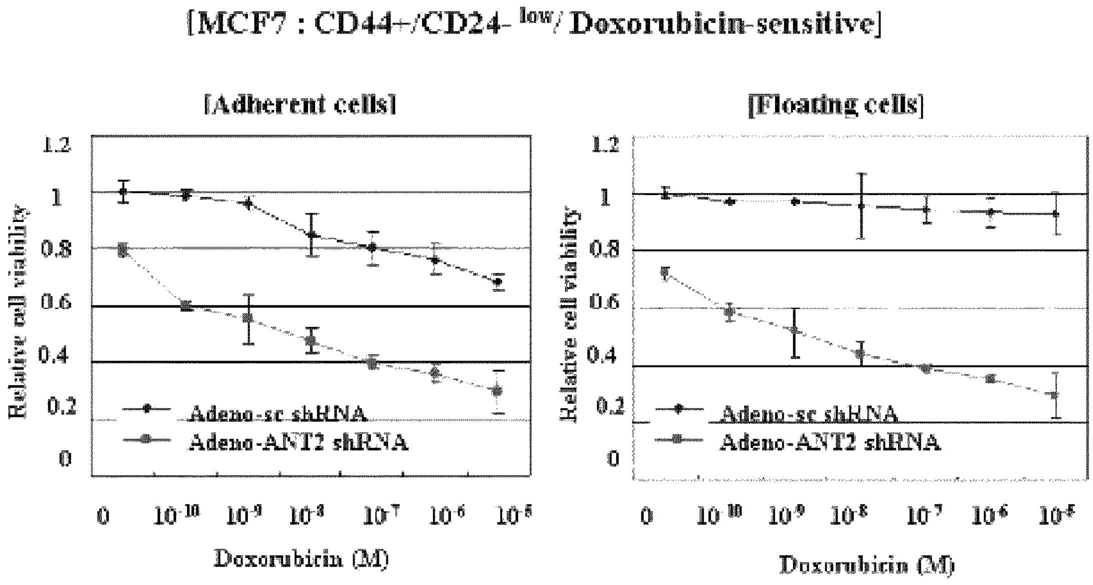

FIG. 36 shows the result of low doxorubicin resistance breast cancer cell lines, MCF7 treated with ANT2 shRNA, wherein MCF7 with a low proportion of the breast cancer progenitor cells (CD44+/CD24−) is sensitive to doxorubicin (adherent cells) while only the progenitor cells (CD44+/CD24−) shows resistance to doxorubicin (floating cells) and that the introduction of ANT2 shRNA makes the cells, whether sorted for CD44+/CD24− cells or unsorted, sensitive to doxorubicin.

Figure 37:
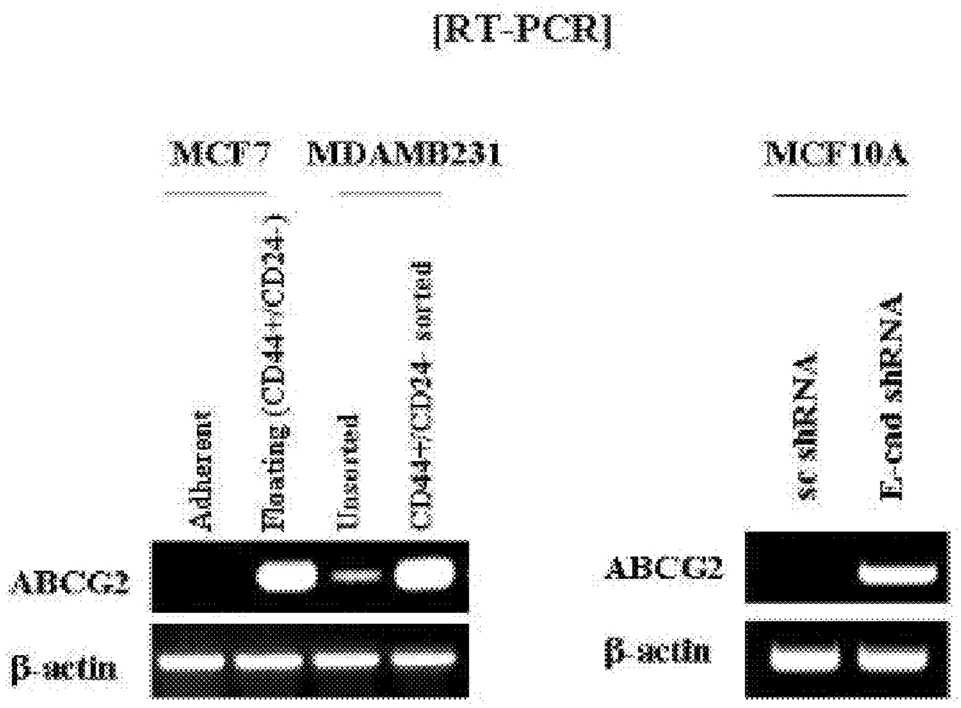

FIG. 37 is a diagram shown the result of RT-PCR, wherein the progenitor cells (CD44+/CD24−) isolated from both the breast cancer cell lines MCF7 and MDA-MB-231 are high in the mRNA expression level of ABCG2 involved in drug resistance, in contrast to unsorted cells (left panel) and that when the normal breast epithelial cell line MCF10A is mesenchymally transdifferentiated by transfection with E-cadherin shRNA, the resulting cells are increased in the mRNA level of ABCG2 (right panel).

Figure 38:
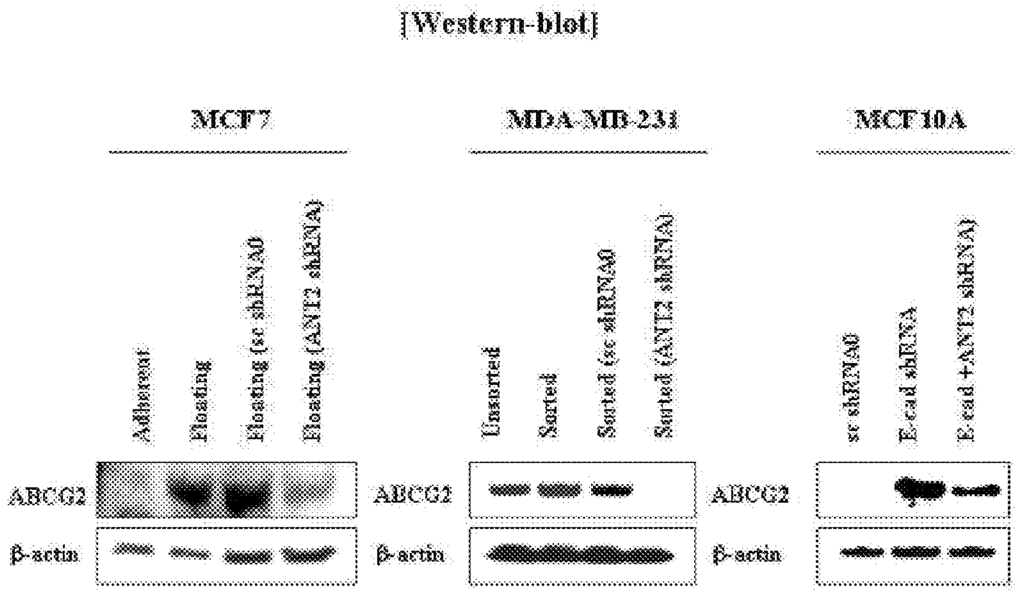

FIG. 38 is a diagram shown the result of Western-blot, wherein that the progenitor cells (CD44+/CD24−) isolated from both the breast cancer cell lines MCF7 and MDA-MB-231 are high in the protein expression level of ABCG2 involved in drug resistance, in contrast to unsorted cells, and decreased in the protein expression level of ABCG2 when transfected with ANT2 shRNA and that when the normal breast epithelial cell line MCF10A is mesenchymally transdifferentiated by transfection with E-cadherin shRNA, the resulting cells are increased in the protein level of ABCG2.

Figure 39:
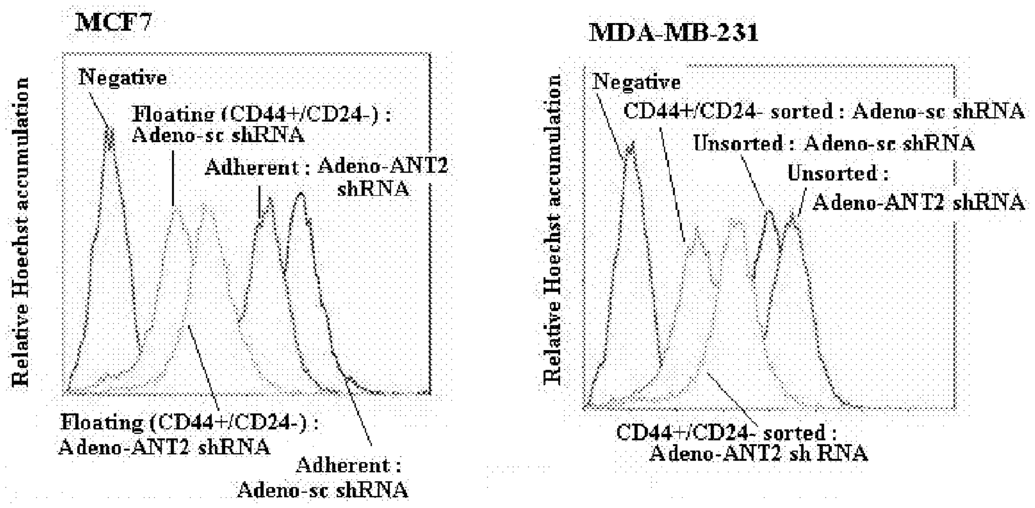

FIG. 39 is a diagram showing the result of FACS analysis, wherein the progenitor cells (CD44+/CD24−) isolated from both the breast cancer cell lines MCF7 and MDA-MB-231 are higher in the activity of ABCG2 involved in drug resistance than are unsorted cells and that when the normal breast epithelial cell line MCF10A is mesenchymally transdifferentiated by transfection with E-cadherin shRNA, the resulting cells are increased in the activity of ABCG2.

Figure 40:
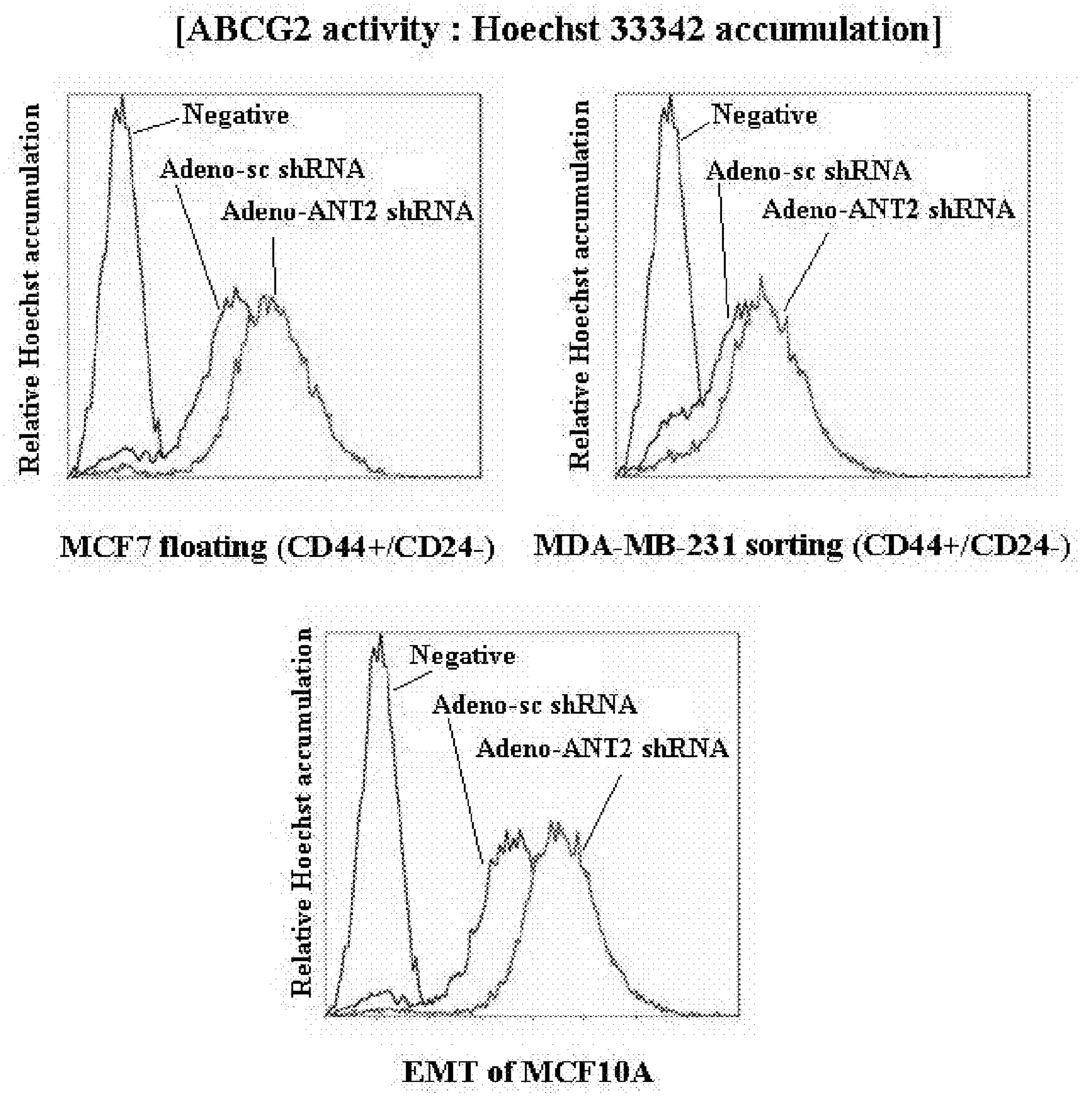

FIG. 40 is a diagram showing the result of FACS analysis, wherein while the progenitor cells (CD44+/CD24−) isolated from both the breast cancer cell lines MCF7 and MDA-MB-231 are higher in the activity of ABCG2 involved in drug resistance than are unsorted cells, the introduction of ANT2 shRNA decreases the activity of ABCG2 and that the cells mesenchymally transdifferentiated from the normal breast epithelial cell line MCF10A by transfection with E-cadherin shRNA show an increased activity of ABCG2, but are decreased in the activity of ABCG2 by introduction of ANT2 shRNA thereinto.

Figure 41:
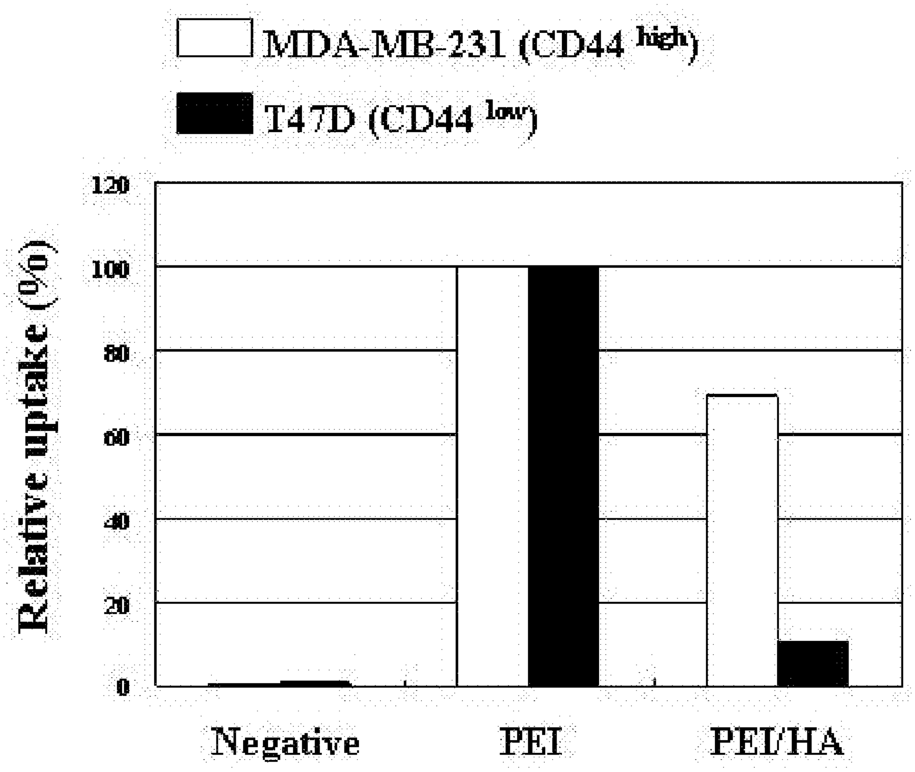

FIG. 41 shows the result of cellular uptake of shRNA-containing nanocomplexes, wherein the nanocomplexes targeting CD44, which is highly expression on the surface of progenitor cells of breast cancer, selectively delivers ANT2 shRNA to the cell line expressing CD44.

DETAILED DESCRIPTION OF THE INVENTION

In another embodiment, the present invention provides a small interfering RNA (siRNA) specifically binding to mRNA of adenine nucleotide translocator 2 (ANT2).

The present invention also provides an expression vector containing the polynucleotide corresponding to the siRNA nucleotide sequence.

The present invention further provides a treatment method for cancer containing the step of administering the said siRNA or the said expression vector to an individual with cancer.

The present invention also provides an anticancer composition containing the said siRNA or the said expression vector.

Hereinafter, the present invention is described in detail.

The present invention provides a small interfering RNA (siRNA) specifically binding to mRNA of adenine nucleotide translocator 2 (ANT2).

In this invention, the said siRNA is composed of a 17-25 mer sense sequence, a 7-11 mer loop sequence and an antisense sequence corresponding to the above sense sequence which is selected from nucleotide sequences of adenine nucleotide translocator 2 (ANT2) mRNA. The sense sequence corresponds to the nucleotide sequence of ANT2 mRNA represented by SEQ ID NO: 1 (see FIG. 15) and the sense sequence itself is represented by SEQ ID NO: 2. The loop sequence is preferably represented by SEQ ID NO: 3 but not always limited thereto.

The present invention also provides an expression vector containing the polynucleotide corresponding to the siRNA nucleotide sequence.

In this invention, the plasmid expression vector containing the polynucleotide corresponding to the nucleotide sequence of ANT2 siRNA is constructed with five T bases ($T_5$) that are transcription termination sequences and the polynucleotide corresponding to the nucleotide sequence of ANT2 siRNA designed to form HI (RNA polymerase III) and hairpin loop structure. The polynucleotide corresponding to the nucleotide sequence of ANT2 siRNA was cloned into Bam HI/Hind III region of HI promoter is generated by cloning into Bam HI/Hind III region of pSilencer 3.1-H1 puro plasmid vector (Ambion, Austin, Tex.) designed to be expressed by HI promoter (see FIGS. 1 and 2). However, in this invention, the vector to express ANT2 siRNA is not limited to pSilence 3.1-H1 puro vector and the promoter to express ANT2 siRNA is not limited to HI promoter, either. For example, Pol III promoter that can start transcription by eukaryotic RNA polymerase III and a promoter such as U6 promoter or CMV promoter that can induce gene expression in mammalian cells are also preferably used but not always limited thereto.

Figure 4:
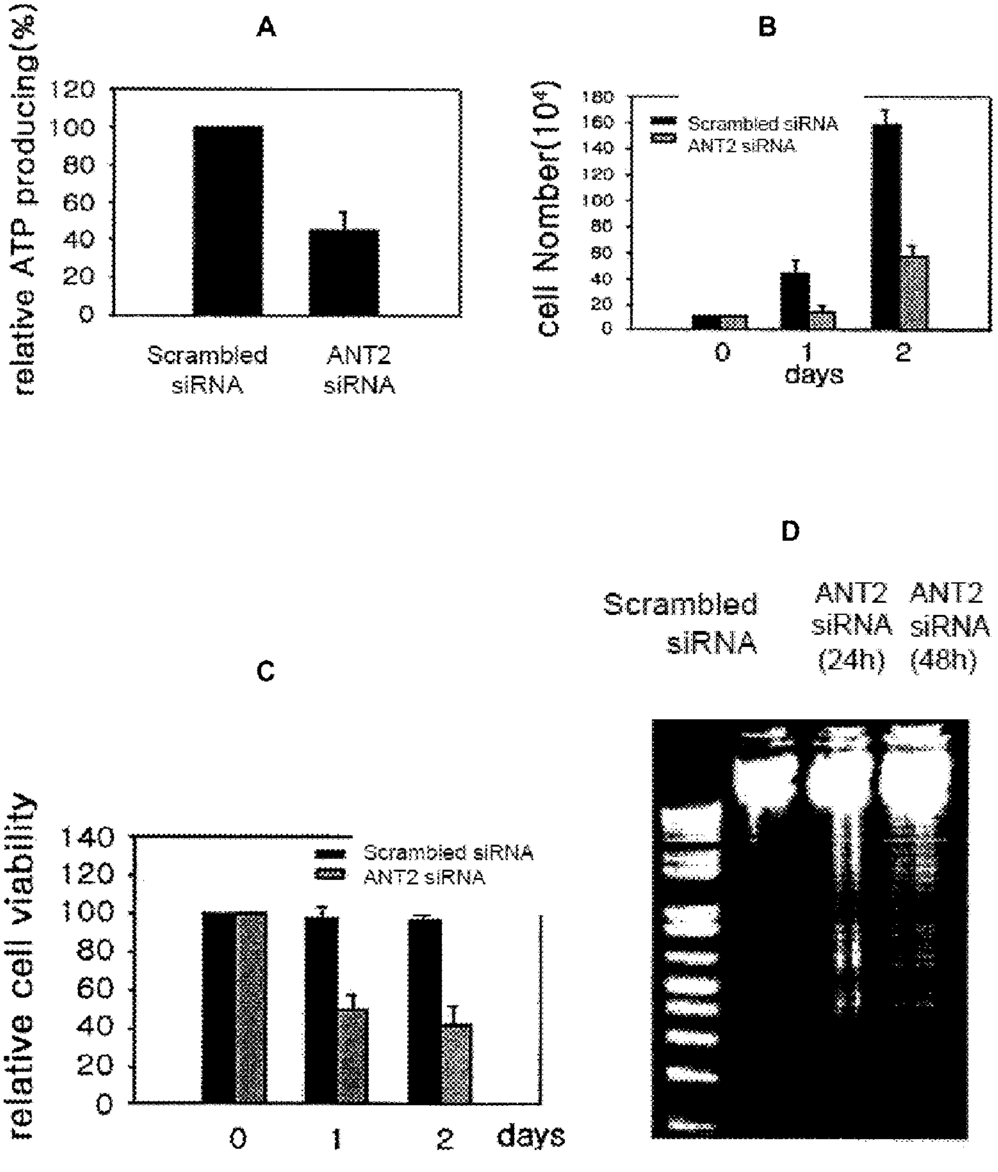
FIG. 4A is a graph showing that the ANT2 siRNA expression vector of the present invention reduces ATP production in breast cancer cells.
FIG. 4B is a graph showing that the ANT2 siRNA expression vector of the present invention inhibits breast cancer cell proliferation, compared with the control, scrambled siRNA.
FIG. 4C is a graph showing the cell survival rate (%) apoptosis of cancer cells induced by the expression vector and FIG. 4 D is a diagram illustrating ANT2 siRNA showing the apoptosis of cancer cells by genome DNA fragmentation.

The present invention provides experimental data wherein ANT2 siRNA expression vector administered to cancer cells induces apoptosis (see FIGS. 4C and 4D) and suppresses the proliferation of ANT2 over-expressing breast cancer cell line (MDA-MB-231) (see FIG. 4B).

The present invention also provides the mechanism of anticancer activity of ANT2 siRNA. As a result, the inventors confirmed that cancer cell death is directly induced by ANT2 siRNA (see FIG. 7 and FIG. 8) and at the same time the anticancer effect of ANT2 siRNA is more effective by indirect inducement of cancer cell death by promoting the expressions of TNF-α and TNFR1 receptor (see FIGS. 7-11).

To investigate the in vivo anticancer effect of ANT2 siRNA, ANT2 siRNA expression vector was inserted into breast cancer cells, which were then injected under the right femoral region of a nude mouse, followed by measurement of time-dependent tumor sizes. As a result, the size of a tumor was reduced in the mouse by the injection of breast cancer cell line where ANT2 siRNA was expressed, compared with that of control (see FIG. 12).

Figure 13:
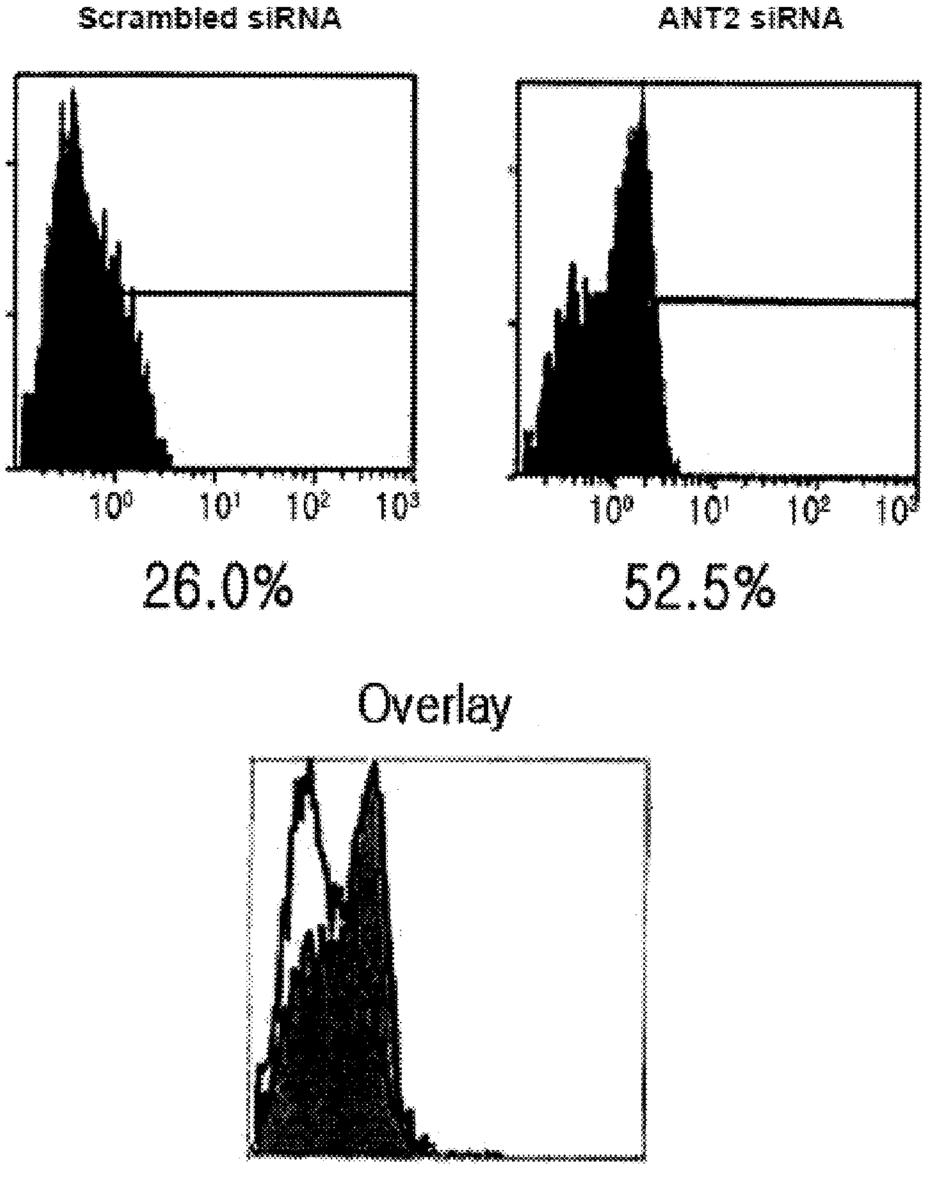
FIG. 13 is a graph showing the effect of ANT2 siRNA of the present invention on multidrug resistance of breast cancer cells (MDA-MB-231) measured by FACS.
Figure 14:
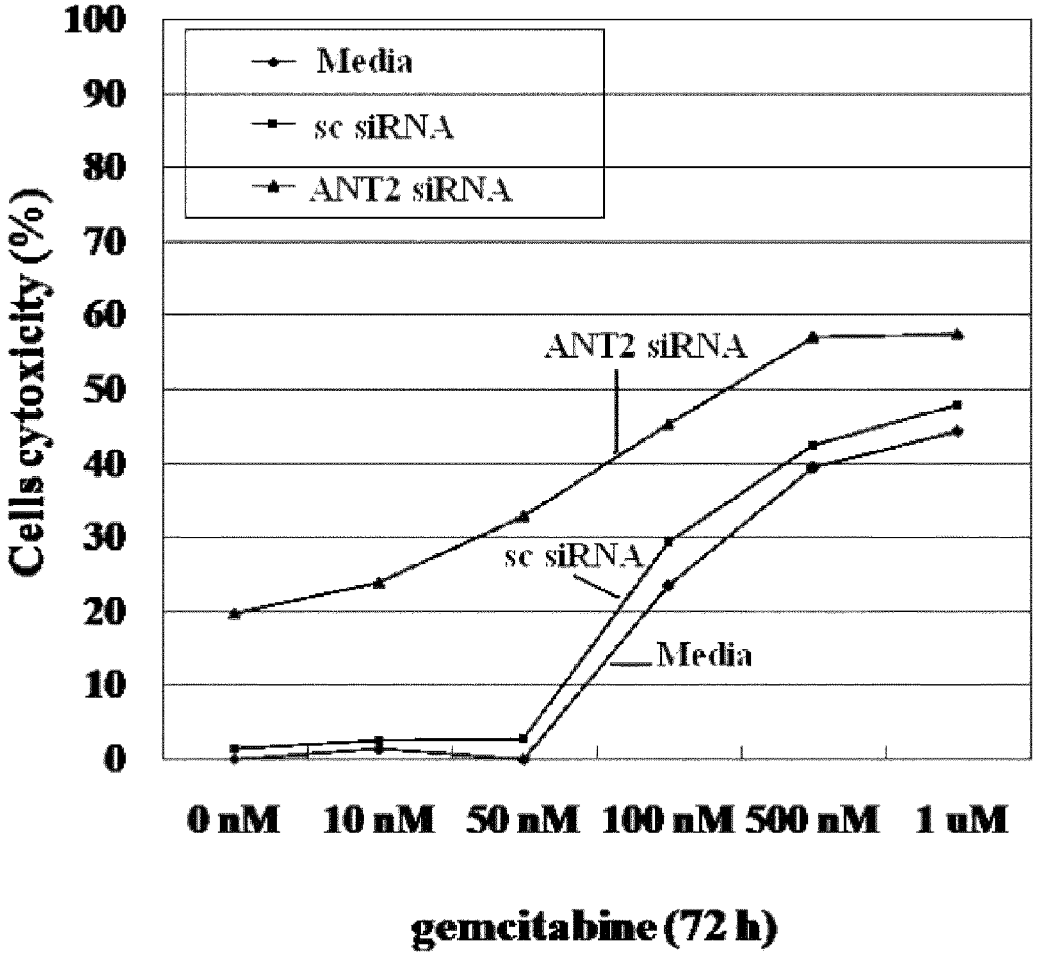
FIG. 14 is a graph showing the association of ANT2 siRNA of the invention with the reactivity of an anticancer agent (gemcitabine) to breast cancer cells (MDA-MB-231).

It was further confirmed that MDR (multidrug resistance) of breast cancer cell line (MDA-MB-231) was reduced by the insertion of ANT2 siRNA, and the reactivity of an anticancer agent such as gemcitabine was increased and $IC_{50}$ was also reduced (see FIG. 13 and FIG. 14). The above results indicate that ANT2 siRNA insertion in cancer cells contribute to the overcoming of multidrug resistance and enhancement of anticancer effect with even lower dose of an anticancer agent.

From the above results, it was confirmed that when ANT2 siRNA expression vector of the invention is inserted into ANT2 over-expressing cancer cells, the expression of ANT2 is suppressed, ATP synthesis which is necessary energy for cancer cell proliferation is interrupted, the expressions of TNF-α and its receptor TNFR1 inducing apoptosis are increased, and thereby apoptosis of cancer cells is induced, suggesting that tumor growth is greatly inhibited by inducing apoptosis.

ANT2 is over-expressed in most cancer cells including stomach cancer, lung cancer, hepatoma and ovarian cancer, therefore ANT2 siRNA expression vector of the present invention can be applied to a variety of cancers.

The present invention further provides a treatment method for cancer containing the step of administering siRNA or the expression vector to an individual with cancer and an anticancer composition containing siRNA or the expression vector.

ANT2 siRNA and siRNA expression vector of the present invention can be administered locally or systemically in different forms of compositions prepared by using various carriers, for example hypodermic injection, intramuscular injection or intravenouse injection, etc. It is preferred to administer ANT2 siRNA or siRNA expression vector directly to the lesion or inject intravenously as a form of nano particles or a complex with liposome where ligand that can recognize a cancer cell specific marker is attached inside or outside. In the case that the complex is intravenously injected, the complex or nano particles are circulated through blood vessels and then reach tumor tissues. And then they specifically bind to a marker expressed specifically on cancer cell surface, so that ANT2 siRNA or the said siRNA expression vector can be delivered into the inside of cancer cell to induce ANT2 silence, resulting in anticancer effect. Previously, Iwasaki et al added GFP gene or HSV thymidine kinase gene to the hepatitis virus L antigen containing nano particles, and then injected the complex into hepatoma xenograft animal model. It was resultingly observed that tumor growth was inhibited in the animal model in which GFP gene was expressed specifically in hepatoma cells and HSV thymidine kinase gene was inserted (Iwasaki et al., Cancer Gene Ther., 14(1):74-81, 2007). Peng et al also reported that the in vivo systemic administration of a protein-gene complex comprising Apotin and asialoglycoprotein recognized specifically by asialoglycoprotein receptor, a hepatoma specific marker, reduced cancer cell growth (Peng et al., Cancer Gene Ther., 14 (1): 66-73, 2007). Grzelinski et al reported that the systemic administration of pleiotrophin specific siRNA inhibited cancer animal model and polyethylene aimine cell growth significantly (Grzelinski et al., Hum. (PEI) complex in glioblastoma Gene Ther., 17(7):751-66, 2006). McNamara et al reported that the administration of cancer cell specific aptamer and siRNA chimera RNA involved in cancer cell survival inhibited tumor cell growth significantly in the prostatic cancer xenograft animal model (McNamara et al., Nat. Biotechnol., 24 (8): 1005-1015, 2006). The said documents are all listed herein as references. As explained above, ANT2 siRNA or the said siRNA expression vector of the present invention can be effectively used for the treatment of cancer by administering them to an individual with cancer according to the method or pathway described in the said reference. Various cancer specific markers have been known and the one reported by Cho is one example (William Chi-shing Cho, Molecular Cancer, 6:1-9, 2007). A marker specific ligand is preferably a receptor or an antibody against a marker. A nano complex for gene therapy is preferably prepared by mixing ANT2 siRNA or the expression vector of the present invention with liposome, polyethyleneglycol (PEG) and polyethyleneimine.

In one embodiment, the present invention provides a method treating cancers and stem cells of cancers using an anticancer agent that is able to inhibit the proliferation of cancer cells especially over-expressing ANT2 which is closely involved in the development and progress of cancer.

In a preferred embodiment, the present invention provides a method for treating breast cancers wherein administering an effective amount of a pharmaceutical composition containing adenine nucleotide translocator 2 (ANT2) small interfering RNA (siRNA) or adenine nucleotide translocator 2 (ANT2) short hairpin RNA (shRNA) as an active ingredient to a subject with cancer. Furthermore, the present invention provides a method for treating stem cells of breast cancers by treating the stem cells of breast cancers with a composition comprising adenine nucleotide translocator 2 (ANT2) small interfering RNA (siRNA) or adenine nucleotide translocator 2 (ANT2) short hairpin RNA (shRNA), in vivo or in vitro.

In another embodiment, the present invention provides a method of inhibiting metastasis of breast cancer cells by administering an effective amount of a pharmaceutical composition comprising adenine nucleotide translocator 2 (ANT2) small interfering RNA (siRNA) or adenine nucleotide translocator 2 (ANT2) short hairpin RNA (shRNA) as an active ingredient to a subject having the breast cancers.

Breast cancer cells are known to activate certain signal transduction pathways through the cell receptor EGFR (epidermal growth factor receptor) for their proliferation, survival, and migration and invasion into other tissues. Particularly, HER2/neu, a member of the EGFR family, is known to be overexpressed on the surface of the cancer cells, up to 30% of breast cancer patients. The overexpression of HER2/neu gives rise to a poor prognosis for breast cancer patients and shows multi-drug resistance in chemotherapy. Representative among the HER2/neu-mediated signal transduction pathway is the PI3K/Akt signaling pathway, the activation of which causes breast cancer cells to proliferate, survive, and migrate and invade into other tissues. Therefore, the treatment of breast cancer has focused on down-regulating the expression of HER2/neu or interfering with the activity of the HER2/neu-mediated signaling pathway.

The present invention provides a method wherein, when the expression of the ANT2 gene, which is known to be overexpressed in breast cancer cells and plays a crucial role in the ATP production of breast cancer cells, is inhibited by ANT2 siRNA or ANT2 shRNA. In addition, the cancer cells are not only induced to undergo cell death due to an insufficient supply of the energy necessary for the survival thereof, but also prevented from migration or invasion into other tissues, resulting in the suppression of cancer metastasis.

Without bound to any theory, it is known that HSP90 (heat shock protein 90) maintains the expression of HER2/neu on the surface of breast cancer cells and to perform its functions only when it binds to ATP. Accordingly, the present invention expected that when the intracellular ATP level of breast cancer cells is depleted by ANT2 siRNA or ANT2 shRNA, HSP90 cannot bind sufficiently to ATP and thus cannot perform its functions, leading to the degradation of HER2/neu. From this expectation, the present inventors framed a hypothesis that the degradation of HER2/neu causes a decrease in the activity of HER2/neu-mediated PI3K/Akt signaling pathway, resulting in weakening the ability of breast cancer cells to migrate and invade into other tissues. In this invention, the human breast cancer cell line SK-BR3, known to overexpress HER2/neu, was induced to decrease in ANT2 expression level by the introduction of ANT2 shRNA thereinto. It was observed that the lack of intracellular ATP decreases HSP90 activity, resulting in suppressed HER2/neu expression. In addition, it was experimentally proved that the HER2/neu-mediated PI3K/Akt signaling pathway is inhibited, resulting in suppressing the ability of breast cancer cells to migrate and invade into other tissues.

The TRAIL/apo2 ligand, a member of tumor necrosis factor, can selectively kill cancer cells, but not normal cells. However, the use of TRAIL in chemotherapy makes cancer cells resistant to TRAIL. This resistance is currently a popular research topic. Accordingly, the present inventors tried to solve the resistance problem using ANT2 shRNA.

The present invention presents that the introduction of ANT2 siRNA or ANT2 shRNA into breast cancer cells promotes TRAIL-induced apoptosis of tumor cells and amplifies the suppressive effect of TRAIL on tumor growth both in cell culture conditions (in vitro) and in animals (in vivo). In this context, the regulation of TRAIL receptor expression was found to account for the mechanism of ANT2 siRNA or ANT2 shRNA in promoting the TRAIL-induced apoptosis of breast cancer cells. Among the TRAIL receptors, there are DR4 (TRAILR1; TRAIL receptor 1) and DR5 (TRAILR2: TRAIL receptor 2). When TRAIL binds to the DR4 and DR5, the apoptosis signal is transduced into the cancer cell, so that the cell dies. However, the TRAIL receptors DcR1 (decoy receptors 1: TRAILR3) and DcR2 (decoy receptors 2: TRAILR4) function to protect tumor cells from DR4 and DR5-mediated apoptosis signals. That is, if TRAIL binds to DcR1 and DcR2, the apoptosis signal is not transduced into the tumor cells. There are various reasons for the resistance of tumor cells to TRAIL. Important among them is the fact that DcR1 and DcR2 are up-regulated on the surface of tumor cells while DR4 and DR5 is down-regulated. The present inventors have verified that ANT2 siRNA or ANT2 shRNA cause an alteration in the intracellular signal transduction pathways of cancer cells to up-regulate DR4 and DR5 with the concomitant down-regulation of DcR1 and DcR2, thus increasing the sensitivity of tumor cells to TRAIL and overcoming the drug resistance of tumor cells.

Furthermore, the present invention provide a method wherein, through a cell culture experiment (in vitro) and an animal test (in vivo) that the knock-down of ANT2 by ANT2 siRNA or ANT2 shRNA interference promotes the therapeutic effect of TRAIL on breast cancer and gives a solution to the problem of resistance to TRAIL, which is based on the regulation of TRAIL receptor expression.

One of the most difficult problems with chemotherapy and radiotherapy is the post-treatment emergence of new tumors (cancer recurrence). Currently used chemo- or radiotherapy can kill most of tumor cells, but not all in many cases. Some cells left following treatment might be the source of recurrence and are thought to be cancer stem cells (e.g., breast cancer stem cells). It is therefore very important to effectively eliminate breast cancer stem cells. In the present invention, ANT2 siRNA or ANT2 shRNA was proven to be able to kill breast cancer stem cells.

To examine the medicinal potential and effect of ANT2 siRNA or ANT2 shRNA as a therapeutic for breast cancer stem cells, breast cancer cell line-derived side populations (CD44+/CD24−), which are the progenitor cells of breast cancer cells were used for the experiment. Also, breast epithelial cells (MCF10A) mesenchymally-transdifferentiated through E-cadherin knockdown were used. This was on the basis of the fact that when transdifferentiated from epitheilial cells (epithelial-to-mesenchymal transition, EMT), the mesenchymal cells show characteristics of breast cancer stem cells. In addition, an adenovirus system was utilized to effectively carry ANT2 shRNA into breast cancer stem cells. In this context, adenovirus expressing ANT2 shRNA was constructed and infected into breast cancer stem cells. As a result, ANT2 shRNA efficiently induced apoptotic cell death in both of the two cell groups of breast cancer stem cells characteristic. Also, ANT2 shRNA solved the problem of resistance and thus sensitized both cells to the drug.

It is apparent to those skilled in the art that the administration dose vary depending on the patient's weight, age, gender, health state and diet, frequency e of administration, route of administration, and rate of the excretion of the composition, delivery methods, and the severity of disease. Without bound to any theory, a dose of such as 0.1-10 mg/kg, 0.5-5 mg/kg, or 0.7-3 mg/kg of siRNA or shRNA can be used to treat the subject in need thereof.

EXAMPLES

Practical and presently preferred embodiments of the present invention are illustrative as shown in the following Examples. However, it will be appreciated that those skilled in the art, on consideration of this disclosure, may make modifications and improvements within the spirit and scope of the present invention.

Example 1

Construction of ANT2 siRNA Expression Vector

<Method A>

ANT2 siRNA was provided by National Center for Biotechnology Information (NCBI, http://www.ncbi.nlm.nih.gov/) and further prepared based on the nucleotide sequence corresponding to the second exon of Genebank Accession No. NM_001152 (SEQ ID NO: 1), which is the nucleotide sequence of the most appropriate obtained oligomer from the of all the siRNA candidate prediction sequences program (http://www.ambion.com/technical.resources/siRNA target finder). The present inventors also constructed ANT2 siRNA-2 (SEQ ID NO: 14, 5'-CUGACAUCAUGUACA-CAGG-3') and ANT2 siRNA-3 (SEQ ID NO: 15, 5'-GA-UUGCUCGUGAUGAAGGA-3'), in addition to ANT2 siRNA for comparison. The construction of ANT2 siRNA, ANT2 siRNA-2 and ANT2 siRNA-3 was conducted by Bioneer (Korea).

Figure 1:
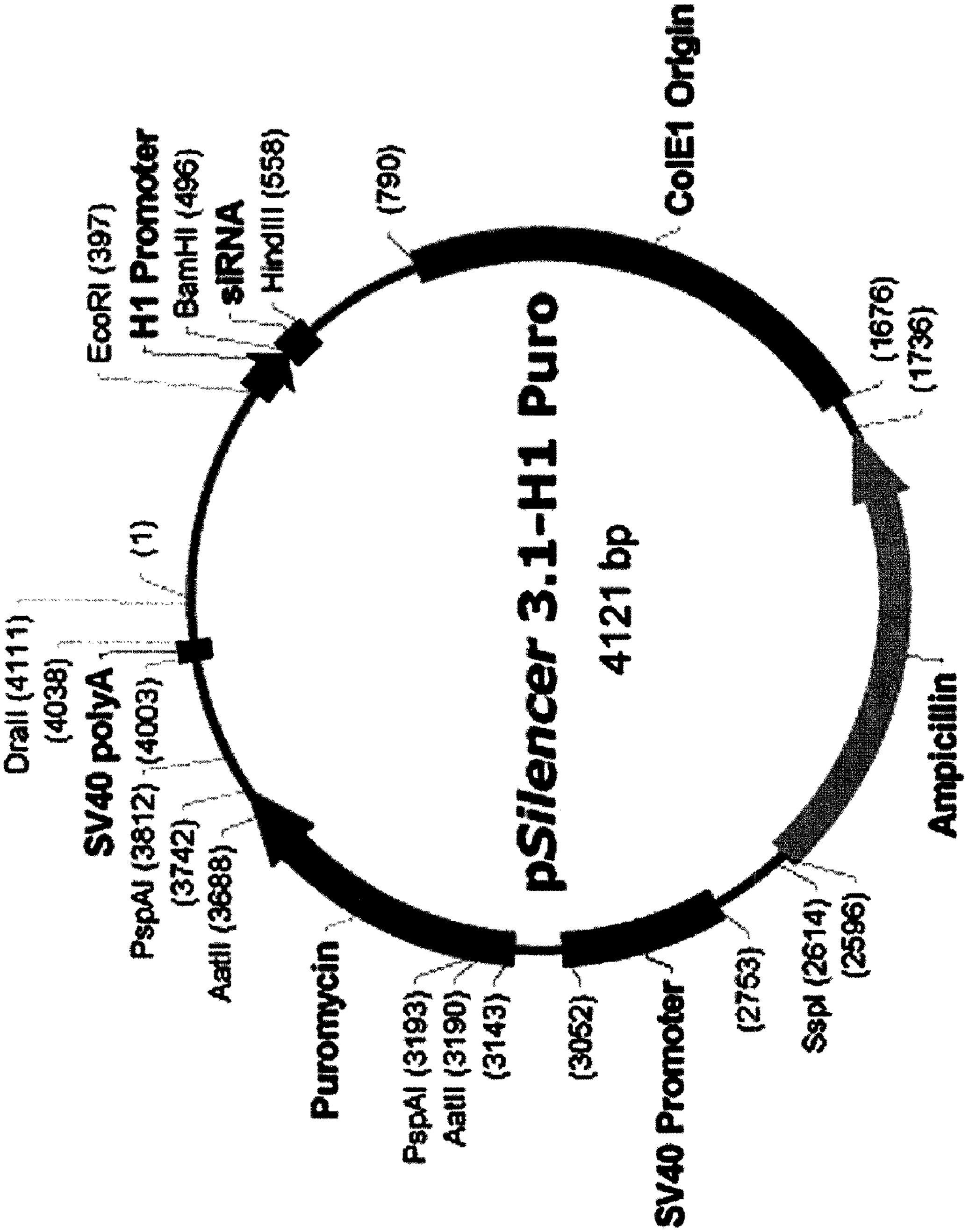
FIG. 1 is a diagram showing the cleavage map of an expression vector for the expression of adenine nucleotide trans locator 2 (ANT2) mRNA specific siRNA (small interfering RNA).
Figure 2:
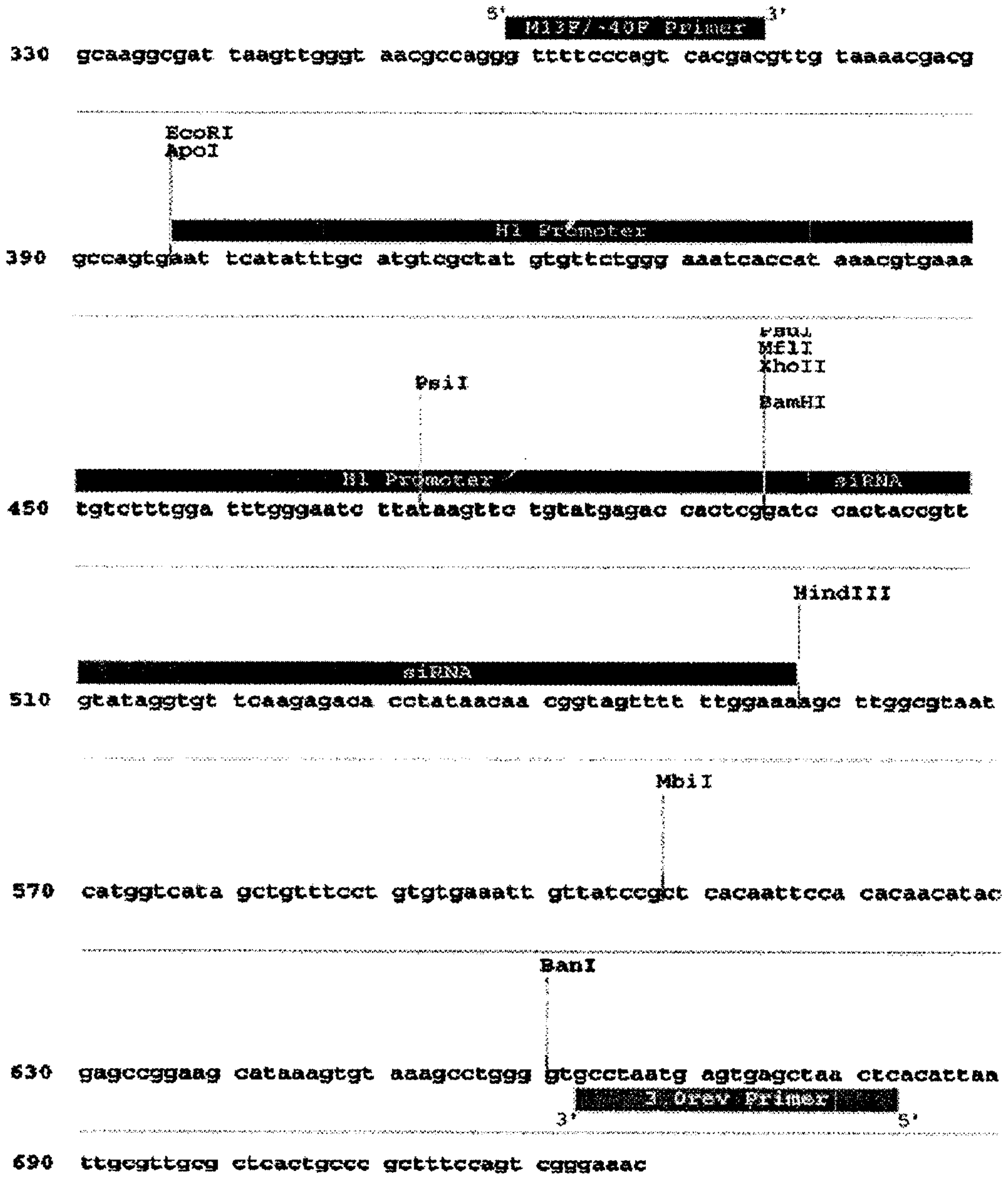
FIG. 2 is a diagram showing the cleavage map of an expression vector (SEQ ID NO: 18) for the expression of adenine nucleotide trans locator 2 (ANT2) mRNA specific siRNA (small interfering RNA).

Particularly, the vector was designed to include a target sequence (5'-GCAGAUCACUGCAGAUAAG-3', SEQ ID NO: 2) corresponding to 197-217 of ANT2 mRNA (SEQ ID NO: 1) that is the target sequence of siRNA inhibiting ANT2 expression, a loop sequence (5'-TTCAAGAGA-3', SEQ ID NO: 3) and an ANT2 shRNA anti-sense sequence (5'-AACUUAUCUGCAGUGAUCUGC-3', SEQ ID NO:17) binding complementarily to the said target sequence. TT was also included in order to increase the expression efficiency of siRNA, which was cloned into Bam HI and Hind III regions of MCS (multicloning site) of pSilencer 3.1-H1 puro plasmid vector (Ambion Co.) to be expressed by H1 promoter (FIGS. 1 and 2). In the meantime, scrambled siRNA used as a negative control which was not capable of interrupting ANT2 expression but was able to play a same role was purchased from Ambion Co. ANT2 siRNA-2 and ANT2 siRNA-3 were also constructed by the same manner as described above except they were designed to target different sequences.

<Method B>

ANT2 mRNA sequence (GenBank Accession No. NM_001152) was obtained from National Center for Biotechnology Information (NCBI, http://www.ncbi.nlm nih.gov/). The candidate sets of ANT2 siRNA were obtained by introducing the above ANT2 mRNA sequence to siRNA prediction program (http://www.ambion.com/technical, resources/siRNA target finder). Among several candidates, siRNA binding to sequence 5'-GCAGAUCACUGCAGAUAAG-3' (SEQ ID NO:2), corresponding to second exon of the ANT2 mRNA, was prepared to detect the silencing effect on ANT2 mRNA in vitro test. The synthesis of ANT2 siRNA was conducted at Bioneer (Korea).

Based on these result, ANT2 shRNA was prepared. Specifically, two stranded oligomers with following sequences were synthesized.

```
5' GCAGATCACTGCAGATAAGTT 3' 5' TTCAAGAGA 3' (loop)
5' AACTTATCTGCAGTTCAGATCTGC 3'

3' CGTCTAGTGACGTCTATTCAA 5' 3' AAGTTCTCT 5' (loop)
3' TTGAATAGACGTCAAGTCTAGACG 5'
```

After annealing with above two oligomers, the sequences were cloned into the BamHI and HindIII region within the MCS (multi-cloning site) of pSilencer 3.1-H1 puro plasmid vector (Ambion). A sequence of TT was attached to end of the sense sequence to improve the efficiency of siRNA expression.

In the experiments to confirm ANT2 shRNA effects, a scrambled shRNA (purchased from Ambion) was used as a negative control, which gives the same condition as a shRNA of interest, but neither block the expression of the ANT2 nor affect the expression of the target mRNA.

The nucleic acid sequences of shRNA expressed from the above vector are provided below:

```
                                    (SEQ ID NO: 16)
5'-GCAGAUCACUGCAGAUAAGUU-3' (sense sequence
of ANT2 shRNA)

                                     (SEQ ID NO: 3)
5'-UUCAAGAGA-3' (loop sequence of ANT2 shRNA)

                                    (SEQ ID NO: 17)
5'-AACUUAUCUGCAGUGAUCUGC-3' (anti-sense sequence
of ANT2 shRNA)
```

Example 2

Measurement of the Activity of ANT2 siRNA Expression Vector

<2-1> Inhibitory Effect of ANT2 siRNA on ANT2 Expression

In this invention, ANT2 expressions in different human cancer cell lines were investigated. As a result, the present inventors selected a breast cancer cell line (MDA-MB-231) exhibiting high ANT2 expression for the experiment (FIG. 3A). The MDA-MB-231 cell line of the invention was purchased from Korean Cell Line Bank (KCLB) and cultured in OM EM (Sigma) supplemented with 10% FBS (fetal bovine serum), 100 units/ml of penicillin and 100 μg/ml of streptomycin (Sigma) in a 37° C., 5% CO2 incubator (Sanyo, Japan).

To investigate whether ANT2 siRNA of the invention could actually inhibit ANT2 expression, RT-PCR was performed with the said breast cancer cell line in the presence of ANT2 siRNA to measure the level of ANT2 expression. Particularly, the cells were distributed into a 6-well plate ($2\times10^5$ cells) or 100 rum dish ($2\times10^6$ cells), followed by culture for 24 hours. Then, Lipofectamine 2000 (Invitrogen), pSilencer 3. I-HI puro ANT2 siRNA vector or pSilencer 3.1-H1 puro scrambled siRNA vector was added at the concentration of 2 μg/$2\times10^5$ cells. Reaction was induced in serum-free medium at room temperature for 15 minutes to let them bind well. The breast cancer cell line was transfected with the reacted medium, followed by further culture for 4 hours. The medium was discarded, and the cells were washed with PBS, followed by further culture for 24-48 hours in serum containing medium.

After 24-48 hours from the transfection, the cells were treated with Trizol (Invitrogen) to separate the total RNA. And cDNA was synthesized from 5 pg of the total RNA by using RT-PCR kit (Promega, Madison, Wis.). The obtained cDNA was denatured at 94° C. for 5 minutes, followed by 35 cycles of denaturation at 94° C. for 1 minute, annealing at 55° C. for 1 minute, polymerization at 72° C. for 2 minutes, and final extension at 72° C. for 5 minutes. PCR product obtained above was electrophoresed on 1% agarose gel to confirm. The primer sequences used for PCR herein are as follows:

```
1) ANT1 (forward)
                                     (SEQ ID NO: 4)
5'-CTG AGA GCG TCG AGC TGT CA-3';
and

(reverse)
                                     (SEQ ID NO: 5)
5 1 -CTC AAT GAA GCA TCT CTT 5 C-3';

2) ANT2 (forward)
                                     (SEQ ID NO: 6)
5 I -CCG CAG CGC CGT AGT CAA A-3 I;
and

(reverse)
                                     (SEQ ID NO: 7)
5 1 -AGT CTG TCA AGA ATG CTC AA-3';

3) Bel-xL (forward)
                                     (SEQ ID NO: 8)
5 I -GAA TTC AAA TGT CTC AGA GCA 10 ACC
GGG AG-3 I;
and

(reverse)
                                     (SEQ ID NO: 9)
```

-continued

```
5' -GCG GCC GCA TTC CGA CTG AAG AGT GAG
CCC-3';

4) Bax (forward)
                                          (SEQ ID NO: 10)
5' -GAC GGG TCC GGG GAG C-3';
and

(reverse)
                                          (SEQ ID NO: 11)
5'-CAG CCC ATC TTC CAG ATG GT-3';

5) I)-actin: (forward)
                                          (SEQ ID NO: 12)
5 I -GGA AAT CGT GCG TGA CAT TAA GG-3';
and

(reverse)
                                          (SEQ ID NO: 13)
5'-GGC TTT TAG GAT GGC AAG GGA C-3'.
```

As explained hereinbefore, expression of ANT2 siRNA was investigated RT-PCR. As a result, from 24 hours after the transfection, intracellular ANT2 mRNA expression was inhibited in MDA-MB-231 cells by ANT2 siRNA and 48 hours after the ANT2 expression was suppressed significantly by ANT2 siRNA (FIG. 3B).

<2-2> Inhibition of ATP Production and Cell Proliferation and Induction of Apoptosis by ANT2 siRNA The present inventors introduced ANT2 siRNA and the negative control scrambled siRNA respectively into the breast cancer cells (MDA-MB-231) which were cultured to investigate ATP production, cell growth inhibition and apoptosis therein.

ATP Production

To measure the level of intracellular ATP, the cells were reacted with CellTiter-Glo™ regent (CellTiter-Glo™ solution and CellTiter-Glo™ substrate, Promega) and then luminescence was measured by using a luminometer (Tecan Instruments) at room temperature.

<Cell Growth Inhibition>

To investigate the effect of ANT2 siRNA on cell growth, MDA-MB-231 cell line was transfected with ANT2 siRNA or scrambled siRNA by using Lipofectamine2000 (Invitrogen) by the same manner as described in the above Example 2. Then the cell number was counted by hemacytometer on the day of transfection, on the next day and two days later (FIG. 4B).

<Apoptosis>

The transfected cells were reacted with Annexin V and PI (Propidium ionide, BD pharmingen) in a dark room at room temperature for 15 minutes and the cell number was measured by FACS (Epics XL, Coulter, France). Genomic DNA was separated from DNA fragmentation by using genomic DNA kit (Intron, Korea), followed by electrophoresis on 2% agarose gel to measure apoptosis.

As a result, ATP production was reduced in MDA-MB-231 cells transfected with ANT2 siRNA (FIG. 4A), compared with that of the control cells treated with scrambled siRNA (FIG. 4A), and cell proliferation was also reduced significantly after the transfection on the next day and two days later as well (FIG. 4B). Regarding apoptosis of MDA-MB-231 cells by ANT2 siRNA, approximately 50% apoptosis effect was observed on the next day of transfection and after two days from the transfection as well (FIG. 4C). DNA fragmentation was significantly observed in the breast cancer cells transfected with ANT2 siRNA, compared with the control cells both on the 24th and 48th hour from the transfection (FIG. 4D).

Therefore, the present inventors confirmed that ANT2 siRNA has an anticancer effect by inducing apoptosis and inhibiting cell proliferation and ATP production specifically associated with ANT2 expression.

<2-3> Regulation of the Expression of Apoptosis Associated Factors by ANT2 siRNA and Destruction of Mitochondria Membrane by ANT2 siRNA The present inventors observed the expressions of apoptosis associated factors and the changes of mitochondria membrane which are closely associated with apoptosis after insertion of ANT2 siRNA in the breast cancer cell line.

Regulation of the Expressions of Apoptosis Associated Factors

The present inventors transfected MDA-MB-231 cells with ANT2 siRNA or scrambled siRNA and cultured thereof. Then the levels of mRNAs of apoptosis associated factors (Bcl-xL; apoptosis inhibiting factor, and Bax; apoptosis inducing factor) were measured by the same manner as described in Example 2.

To investigate protein levels, the cells were transfected with ANT2 siRNA and scrambled siRNA respectively, and 48 hours later the cells were recovered, lysed in lysis buffer (5 mmol/L EDTA, 300 mmol/L NaCL, 0.1% 1 gepa, 0.5 mmol/L NaF, 0.5 mmol/L Na3V04, 0.5 mmol/L PMSF, 10 g/mL aprotinin, pepstatin) by using leupeptin (Sigma), and centrifuged (15,000×g, 30 min). The supernatant was obtained to measure protein level by using Brandford solution (Bio-Rad). 50 μg of the protein proceeded to 10% SDS-polyacrylamide gel for electrohporesis, transferred onto polyvinylidene difluoride membrane (Millipore), treated with an antibody (anti-Bcl-xL, anti-Bax, and anti-a tublin (Santa Cruz Biotech) and colored by chemiluminescence detection system (Amersham Pharmacia Biotech).

Figure 5:
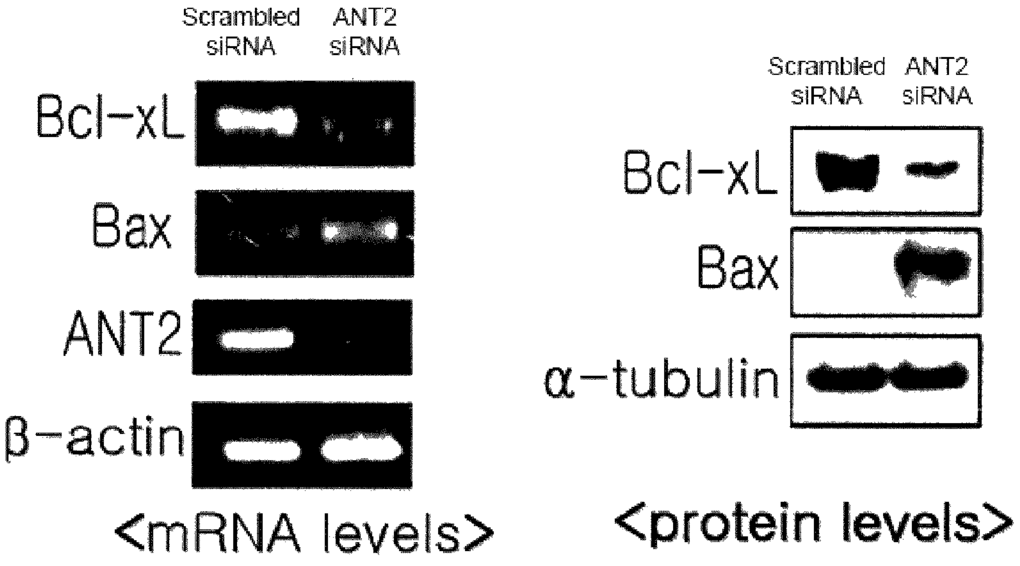
FIG. 5 is a diagram showing the result of RT-PCR (left) and the result of Western-blot (right) each explaining the changes of the levels of Bcl-xL (apoptosis inhibiting factor) and Bax (apoptosis stimulating factor) mRNAs by the ANT2 siRNA expression vector and the effect of the said vector on protein expressions.

As a result, the levels of Bcl-xL mRNA (apoptosis inhibiting factor) and protein were decreased in cells transfected with ANT2 siRNA and at the same time the levels of Bax mRNA (apoptosis inducing factor) and protein were significantly increased (FIG. 5).

<Deconstruction of Mitochondria Membrane>

Figure 6:
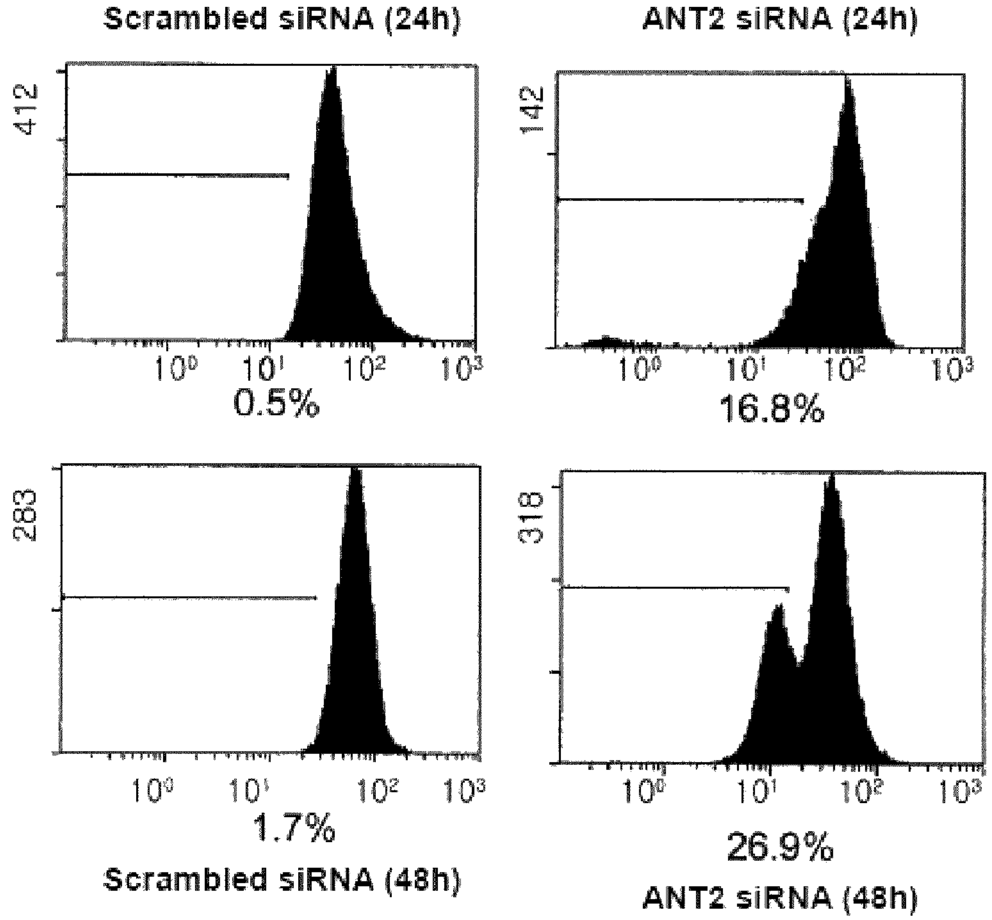
FIG. 6 is a graph showing the destruction of the membrane of mitochondria of breast cancer cells induced by ANT2 siRNA, confirmed by staining with $DiOC_6$.

The present inventors investigated deconstruction of mitochondria membrane by ANT2 siRNA by using DiOC6 that can penetrate into the mitochondria membrane. Particularly, to measure deconstruction of membranes of mitochondria of breast cancer cells transfected with ANT2 siRNA, the cells were treated with 20 nM of DiOC6 (Molecular Probes, Eugene, USA), followed by reaction at 37° C. for 15 minutes. As a result, deconstruction of mitochondria membrane was significant in the cells transfected with ANT2 siRNA, compared with the control cells transfected with scrambled siRNA, both 24 hours (0.5% vs. 16.8%) and 48 hours (1.7% vs. 26.9%) later (FIG. 6).

The above results indicate that ANT2 siRNA of the present invention induces apoptosis of cancer cells by deconstructing mitochondria membrane associated closely with apoptosis and by regulating the expressions of apoptosis associated factors.

<2-4> Direct and Indirect Effect of Inducing Apoptosis by ANT2 siRNA

To investigate whether apoptosis could induced directly by ANT2 siRNA, the present inventors performed staining with propidium iodide (PI) and Annexin V.

Particularly, the cells were transfected respectively with ANT2 siRNA and scrambled siRNA, followed by culture for 24-48 hours. The cells were washed with PBS, to which PI and Annexin V were added. After reaction at room temperature for 15 minutes, 00488 was measured by FACS.

As a result, apoptosis was directly induced by ANT siRNA after 24 (scrambled siRNA: 2.4% vs. ANT2 siRNA: 30.1%) and 48 (scrambled siRNA: 4.7% vs. ANT2 siRNA: 52.9%) hours from the transfection, compared with the control cells transfected with scrambled siRNA. The results observed after 48 hours from the transfection were all consistent among ANT2 siRNA, ANT2 siRNA-2 and ANT2 siRNA-3, and in particular apoptosis was most significantly induced in ANT2 siRNA treated group (FIG. 7 and FIG. 8).

The present inventors further investigated whether ANT2 siRNA could induce apoptosis indirectly, in addition to its direct effect on apoptosis.

Particularly, breast cancer cells were transfected with ANT2 siRNA and scrambled siRNA respectively and cultured for 48 hours. Centrifugation was performed to remove cells remaining in medium. Then, the medium was treated to the cells untransfected with the said siRNA, followed by culture for 24 and 48 hours. Apoptosis was observed.

Figure 7:
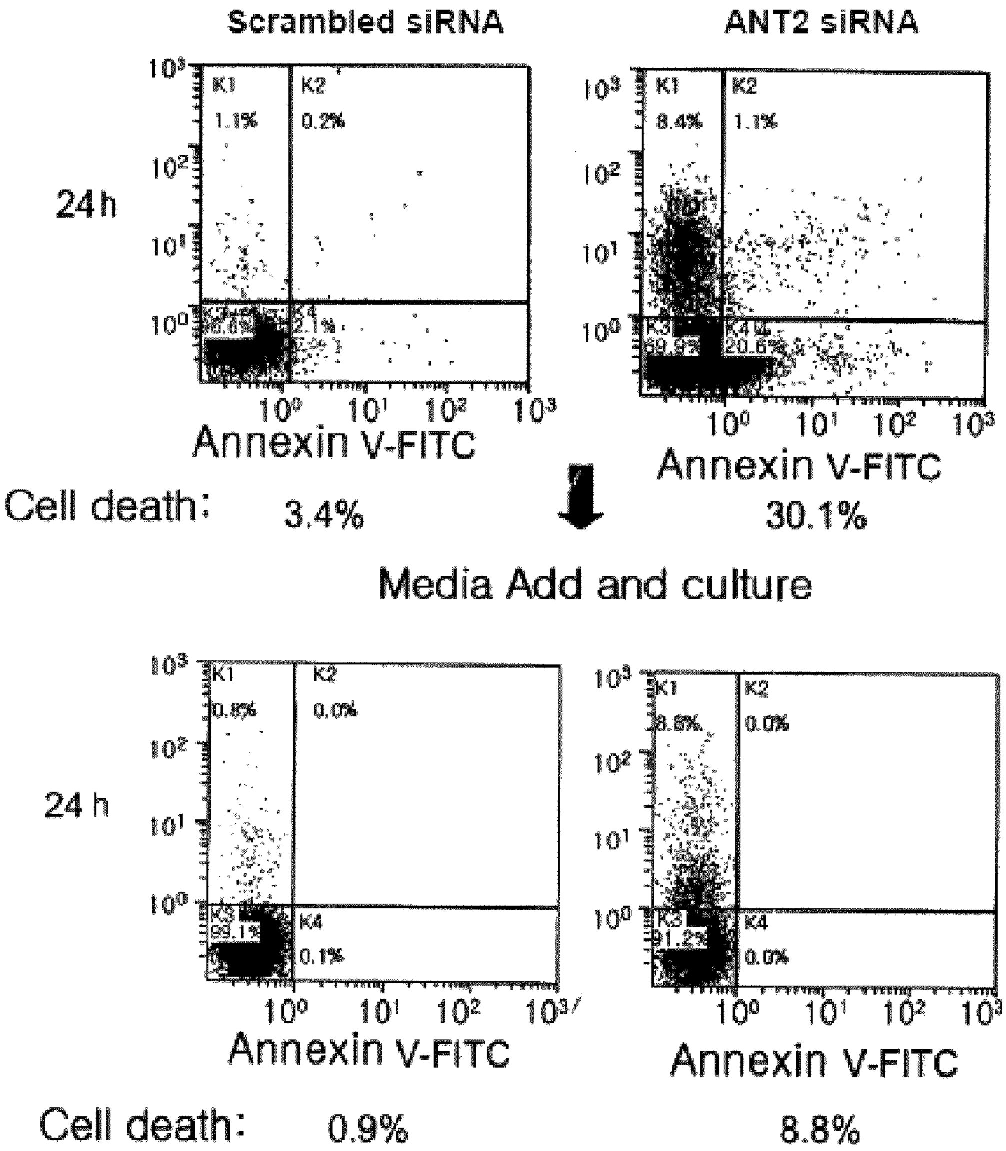
FIG. 7 is a graph showing the result of FACS by using double staining with Annexin V and propidium iodide (PI) to investigate the anticancer effect of ANT2 siRNA expression vector on breast cancer cells by observing direct apoptosis (upper part) and indirect apoptosis (lower part) after 24 hours from the treatment.
Figure 8:
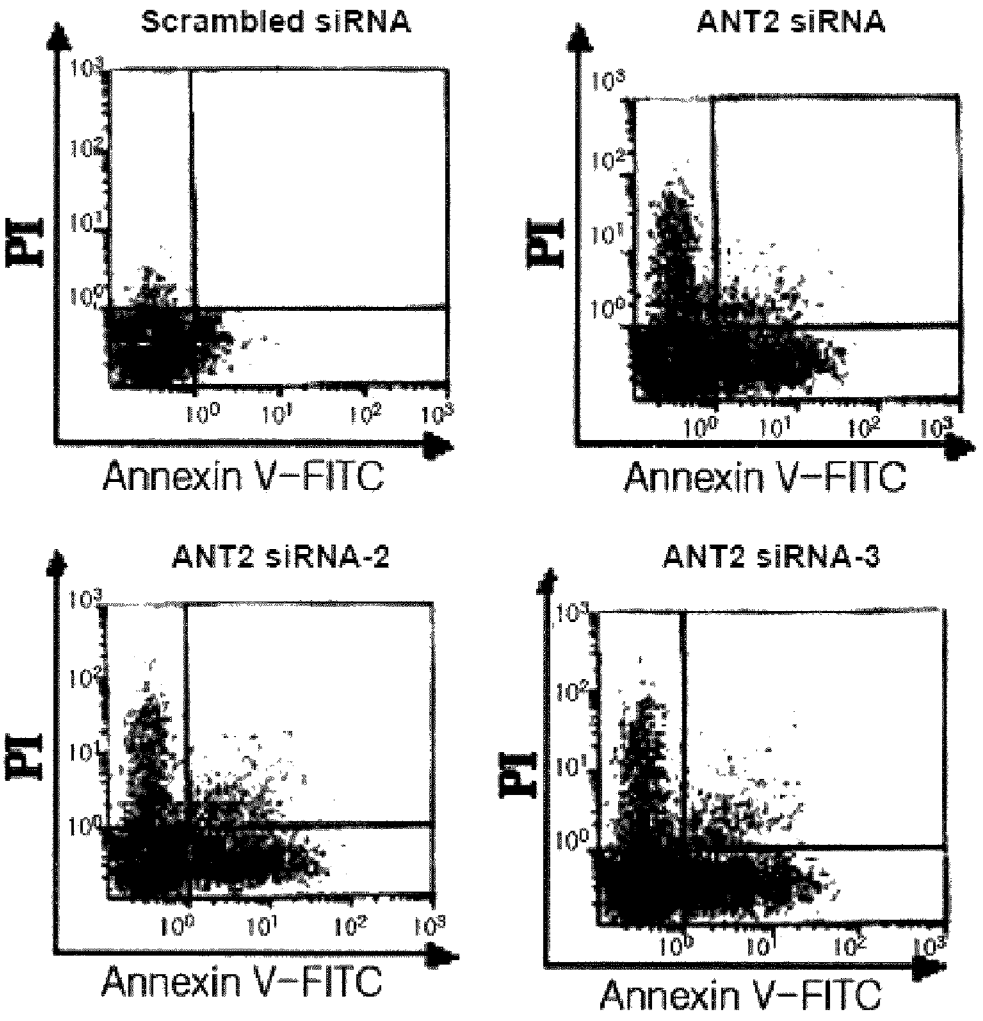
FIG. 8 is a graph showing the result of FACS using double staining with Annexin V and propidium iodide (PI). Particularly, FACS was performed to investigate the anticancer effect of ANT2 siRNA, ANT2 siRNA-2 and ANT2 siRNA-3 expression vectors on breast cancer cells by observing apoptosis after 48 hours from the treatment.

As a result, even though this indirect apoptosis inducing effect was not as high as the direct effect, apoptosis was still induced comparatively high in the cells transfected with ANT2 siRNA, compared with the control cells transfected with scrambled siRNA after 24 hours (control: 0.9% vs. ANT2 siRNA: 8.8%) after the transfection (FIG. 7). The above results indicate that apoptosis is induced indirectly not by ANT siRNA itself but by TNF-ex generated in those cells transfected with ANT2 siRNA and thus the cancer treatment effect might be increased by using ANT2 siRNA.

Example 3

Mechanism of Inducing Apoptosis by ANT2 siRNA

After observing the indirect apoptosis inducing effect of ANT2 siRNA, mechanism of the present inventors tried to analyze the inducing apoptosis. Particularly, the inventors investigated the expressions of TNF-α and one of its receptors TNF-α receptor 1 (TNFR1) in the cancer cell line after ANT2 siRNA treatment. More specifically, ANT2 siRNA and scrambled siRNA (control) were introduced into MDA-MB-231 cells, followed by culture for 24 hours. Then, the cells were treated with 10 μg/ml of BFA (brefeldin A: eBioscience, USA) for 6 hours to interrupt the extracellular secretion of TNF-α. Then, the levels of TNF-α and TNFR1 were measured by RT-PCR or FACS. As a result, RT-PCR and FACS analysis confirmed that the levels of TNF-α and TNF-α receptor 1 (TNFR1) significantly increased by ANT2 siRNA in the cells. To confirm whether indirect apoptosis inducing effect was caused by TNF-α or not, the culture medium of cells transfected with ANT2 siRNA or scrambled siRNA was neutralized by using TNF-α antibody, which proceeded to cell culture.

Figure 9:
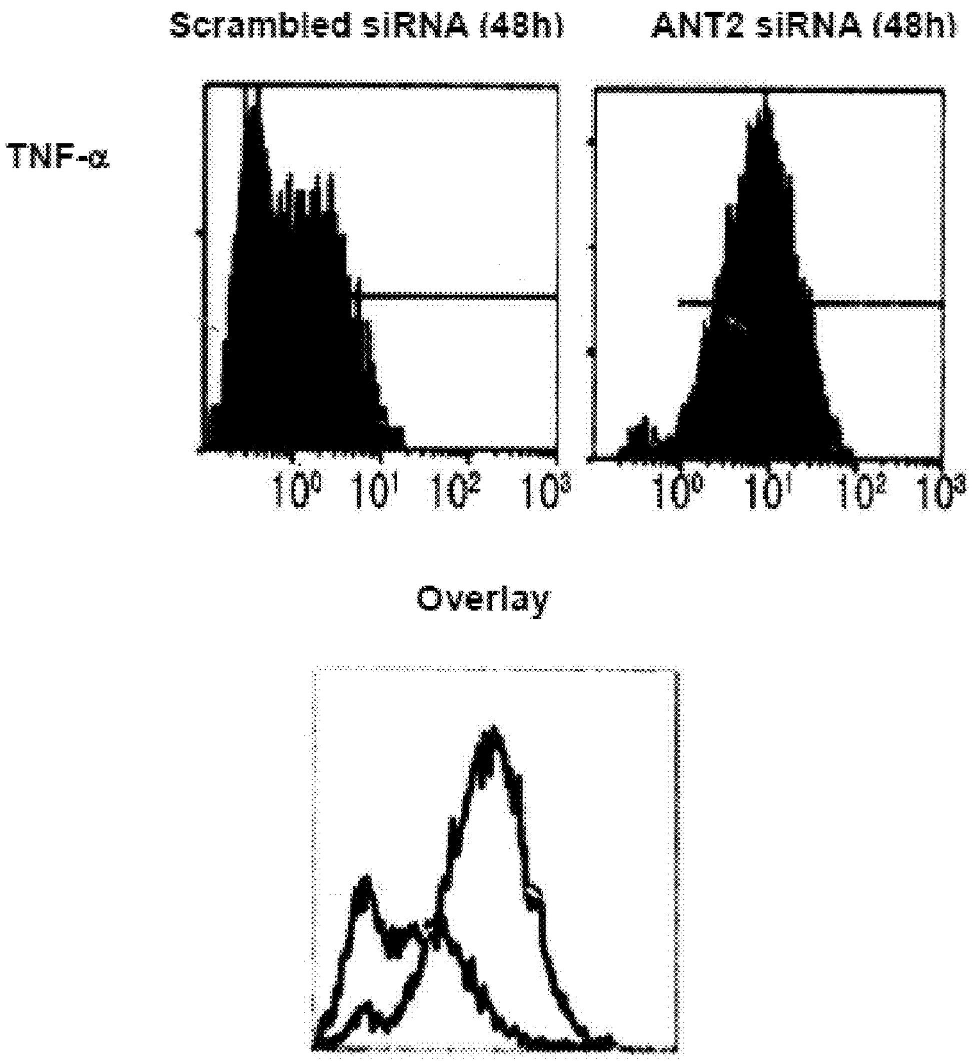
FIG. 9 is a graph showing the relevance between ANT2 siRNA expression vector and TNF-α produced in cancer cells investigated by FACS.
Figure 10:
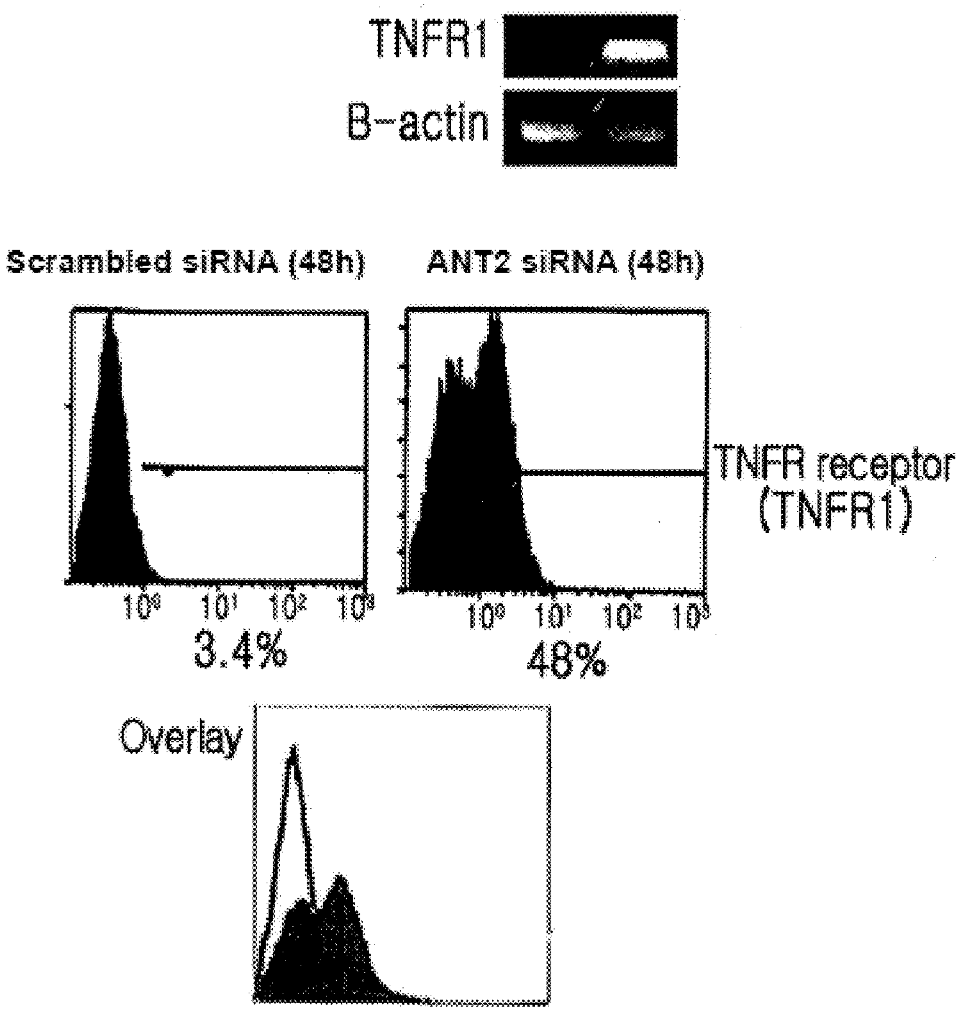
FIG. 10 is a set of a diagram and a graph each showing the relevance between ANT2 siRNA expression vector and the level of TNF-α receptor 1 (TNFR1) mRNA by RT-PCR, and illustrating the correlation between ANT2 siRNA expression vector and TNFR1 by FACS.
Figure 11:
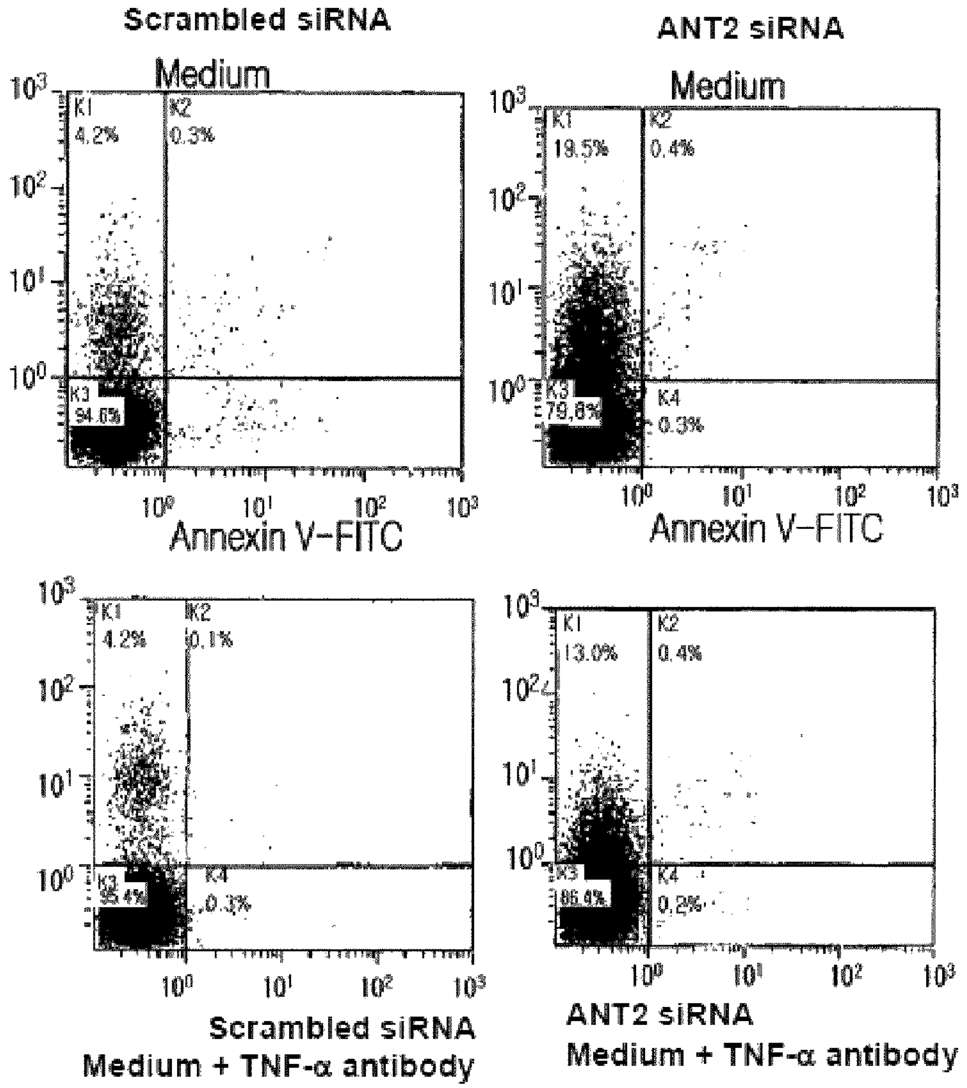
FIG. 11 is a graph showing the result of FACS using double staining with Annexin V and propidium iodide (PI), wherein whether the increase of TNF-α production in cancer cells by ANT2 siRNA expression vector of the invention could induce cancer cell death indirectly, the medium was neutralized by using TNF-α antibody and the effect on apoptosis was measured by FACS.

As a result, the apoptosis inducing effect was reduced, suggesting that TNF-α was involved in indirect apoptosis by ANT2 siRNA. There must be another factors involved in apoptosis since the effect of TNF-α on apoptosis was partial (FIG. 9 and FIG. 11). So, in addition to the direct apoptosis inducing effect of ANT2 siRNA, the increase of the levels of TNF-α and its receptor TNFR1 can enhance the cancer treatment effect. According to the recent reports saying that the direct injection of TNF-α DNA to cancer cells or direct insertion of soluble TNF-α receptor to cancer cells can enhance the cancer treatment effect, the treatment method for cancer using ANT2 siRNA is considered to be very effective.

Example 4

Analysis of In Vivo Anticancer Effect of ANT2 siRNA

In Example 2, it was observed that the treatment of ANT2 siRNA significantly inhibited breast cancer cell proliferation. To investigate whether this result was consistent with that of in vivo experiment, the present inventors introduced ANT2 siRNA and scrambled siRNA into MDA-MB-231 cells ($5\times10^6$/100 μL). The transfected MDA-MB-231 cells were transplanted under the right femoral of balb/c nuce mice (Charles River Japan, Japan), 5 mice per group, and then the tumor size was observed for 33 days to investigate whether the growth of a tumor generated therein 5 could be inhibited by ANT2 siRNA (FIG. 12). The tumor size was calculated by the following Mathematical Formula 1.

$$\text{Tumor Volume (mm}^3\text{)}=\text{Minor Axis}^2\times\text{Major Axis}\times 0.523$$ <Mathematical Formula 1>

As a result, the normal tumor growth was observed in the nude mice transplanted with breast cancer cells transfected with scrambled siRNA, whereas the tumor growth was not observed in the nude mice transplanted with breast cancers transfected with ANT2 siRNA. The above result indicates ANT2 siRNA can reduce tumor cell growth significantly still in vivo. The nude mice were dissected on the 60th day of transplantation to measure the weight of a tumor (FIG. 12).

Example 5

Reducing Effect of ANT2 siRNA on Anticancer Drug Resistance

To investigate how ANT2 siRNA affects the anticancer drug resistance of cancer cells, the present inventors performed Rho123 staining. The anticancer drug resistance is shown when efflux pump on the cell surface pumps an anticancer drug out of cells and thus the amount of the drug remaining in cells becomes so small. Therefore, the 5 effect of ANT2 siRNA on the anticancer drug resistance can be measured by investigating the activity of efflux pumps on cell surface after the administration of ANT2 siRNA.

Particularly, to measure the efflux activity, 100 nM of Rhodamine 123 ($2\times10^5$), followed (Sigma) was by reaction added to MDA-MB-231 cells at 37° C. for 60 minutes. Twenty four hours after the addition, the accumulation of intracellular Rhodamine 123 was increased in the cells transfected with ANT2 siRNA, compared with the cells transfected with scrambled siRNA. The above result indicates that ANT2 siRNA reduces the activity of efflux pumps on cell surface, which is associated with anticancer drug resistance of cancer cells. Besides, it was also observed that the reactivity against such anticancer drug as gemcitabine was also increased to reduce $IC_{50}$ (FIG. 13 and FIG. 14). Therefore, it was confirmed that gene therapy using siRNA can overcome the anticancer drug resistance of cancer cells, minimize the side effects of anticancer drugs by lowering the dosage and thereby increases the treatment effect.

Example 5

Effects of ANT2 shRNA on HER2/neu Expression

The introduction of ANT2 shRNA was found to decrease the expression level of HER2/neu on the surface of the breast cancer cell line SK-BR3 as measured by FACS (flow cytometry and cell sorting).

For introducing ANT2 shRNA into the breast cancer cell line SK-BR3, Lipofectamine™2000 (Invitrogen), a non-viral delivery system, was used. In this regard, the positively charged, hydrophilic components of Lipofectamine™2000 interact with the negative charged shRNA to form a complex. This complex fuses with the cell membranes to deliver the shRNA into the cell.

For FACS analysis, HER2/neu expressed on cell surfaces was bound with a antibody [primary antibody: anti-human HER2/neu antibody (Santa Cruz biotechnology, Heidelberg, Germany)] which was subsequently reacted with a secondary antibody (FITC-conjugated-anti-rabbit-IgG (Santa Cruz biotechnology, Heidelberg, Germany)). Because the secondary antibody was conjugated with a fluorescent material, its detection by FACS allowed the HER2/neu-expressed cells to be sorted from non-expressed cells. SK-BR3 expressed a high expression level of HER2/neu (sc shRNA) whereas the expression of HER2/neu was down-regulated by the introduction of ANT2 shRNA into cells (FIG. 16).

To monitor a change in interaction between HER2/neu and HSP90 with the knockdown of ANT2, proteins were extracted from the human breast cancer cell line SK BR3 transfected with ANT2 shRNA. In detail, first, the proteins were immunoprecipitated with anti-human HER2/neu antibody (Santa Cruz biotechnology, Heidelberg, Germany), followed by Western blotting with an anti-human HSP90 antibody (Santa Cruz biotechnology, Heidelberg, Germany) to determine protein expression levels. The results are given in FIG. 17.

Figure 17:
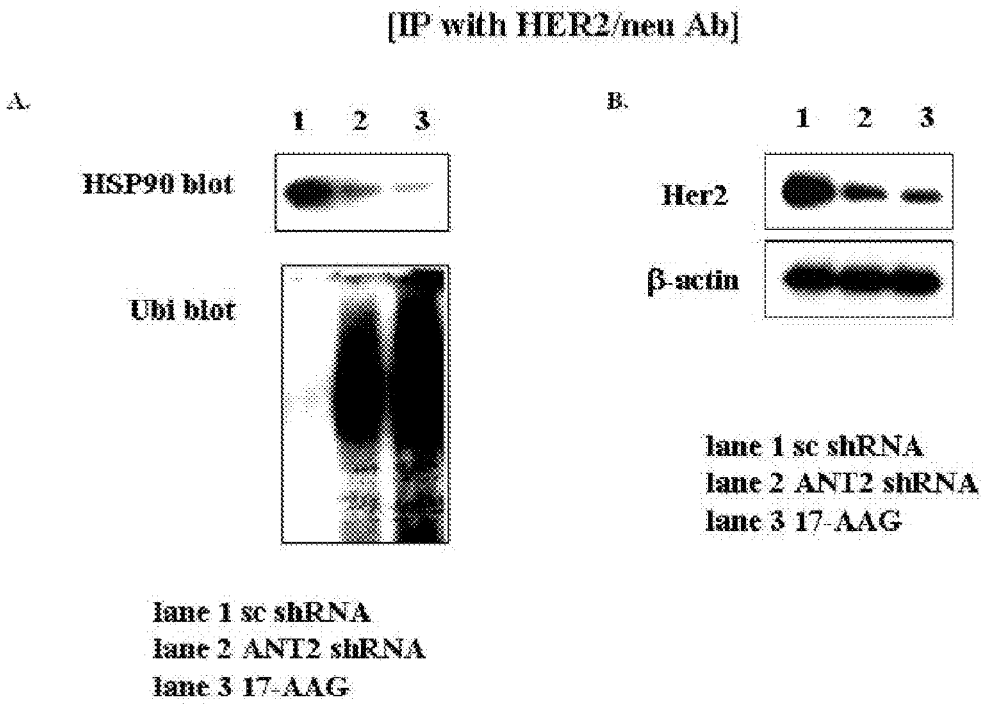

When the expression of ANT2 was down regulated by ANT2 shRNA, as shown in FIG. 17, weak interaction between HER2/neu and HSP90 was detected while an increased level of ubiquitination, a process of marking a protein with ubiquitin before degradation, was detected. That is, the knockdown of ANT2 by shRNA induced a decreased interaction between HER2/neu and HSP90 to increase the ubiquitination of HER2/neu, resulting in a decrease in the expression level of HER2/neu. In this regard, an HSP inhibitor/17-AAG (17-allylamino-17-demethoxygeldanamycin (A.G. Scientific Inc., San Diego, Calif.)) was used as a positive control. Beta-actin, a cytoskeletal protein, was used as a loading control for Western blots because it generally remains the same proportion of total cell protein except under circumstances that experimental conditions are dramatically affecting cytoskeletal rearrangement or cell adhesion. For quantitative analysis of beta-actin, an anti-beta-actin antibody (Cell signaling Tech., Beverly, Mass.) was used.

Example 6

Effect of ANT2 shRNA on Akt Activity

In the breast cancer cell line SK-BR3, highly expressed HER2/neu activates Akt. The activated Akt is known to be involved in the mechanism of survival of breast cancer cells as well as in the migration and invasion of breast cancer cells into other tissues. The activation of Akt can be determined by phosphorylation at tyrosine residues. After transfection of ANT2 shRNA into the human breast cancer cell line SK-BR3, activated Akt (phosphorylated) was quantitatively analyzed with anti-Akt and anti-phospho-Akt antibodies (Cell signaling Tech., Beverly, Mass.). The activity of Akt, which is kept high in the breast cancer cell line, was decreased by the introduction of ANT2 shRNA. 17-AAG, known to inhibit HSP90 and thus the HER2/neu-mediated Akt signaling pathway, was used as a positive control (FIG. 18A).

In addition, the suppression of Akt by ANT2 shRNA was confirmed by another experiment. The activity of phospho-Akt was decreased upon the knockdown of ANT2 by ANT2 shRNA, but was found to be recovered upon the overexpression of ANT2 by introduction of an ANT2-overexpressing vector. LY294002 (Calbiochem, San Diego, Calif.), an inhibitor of PI3K which induces the phosphorylation of Akt, was used as a positive control (FIG. 18B).

In conjunction with the down-regulation of Akt by ANT2 shRNA, an experiment was performed to examine whether ANT2 shRNA suppresses the activity of HSP90, resulting in poor interaction with Akt, on the basis of the report that HSP90 interacts with Akt.

First, HSP90 was immunoprecipitated with the antibody [HSP inhibitor/17-AAG (17-allylamino-17-demethoxygeldanamycin): A.G. Scientific Inc. (San Diego, Calif.)] followed by Western blotting with anti-Akt antibody (Cell signaling Tech., Beverly, Mass.) to determine the expression level. ANT2 shRNA was found to interfere with the interaction between HSP90 and Akt and decrease the level of phospho-Akt (FIG. 18C). The data indicate that the suppression of HSP90 activity by ANT2 shRNA leads to a weak interaction between HSP90 and Akt as well as a reduced activity of Akt.

Example 7

Effect of ANT2 shRNA on VEGF Production

In the present invention, it was found that the introduction of ANT2 shRNA into the human breast cancer cell line SK-BR3 causes a reduction in Akt activity (suppressing the PI3K/Akt signaling pathway), resulting in the down-regulation of VEGF, which is involved in angiogenesis around tumor cells.

In detail, cells transfected with ANT2 shRNA were cultured for 24 hrs, followed by isolation of total RNAs. From the mRNA of them, cDNA was synthesized through reverse transcription with oligo-dT. Using primers specific for VEGF (vascular endothelial growth factor), the expression of VEGF was analyzed.

As shown in FIG. 19A, the knockdown of ANT2 by shRNA in the breast cancer cell line SK-BR3 was observed to reduce the mRNA level of VEGF, which is involved in angiogenesis, as measured by RT-PCR. In addition, intracellular VEGF protein levels were decreased using FACS (flow cytometry and cell sorting). VEGF is produced within cells and released from cells. To prevent this extracellular secretion, the cells were treated with BFA (brefeldin A). When VEGF protein was accumulated, its amounts were compared. In this regard, after the intracellular accumulation of VEGF by treatment with BFA, the cell membranes were perforated to form holes through which the primary anti-VEGF antibody (BD Pharmingen, San Diego, Calif.) was introduced into the cells. Subsequently, a secondary antibody [FITC-conjugated-anti-mouse IgG antibody (BD Pharmingen, San Diego, Calif.)] was allowed to bind to the primary antibody complexed with the VEGF, followed by FACS analysis (FIG. 19B).

In addition, ANT2 shRNA was experimentally reconfirmed to down-regulate the mRNA expression of VEGF. The introduction of an ANT2-overexpressing vector (pcDNA3.0-ANT2 expression vector) increased the expression of ANT2, with the concomitant recovery of VEGF mRNA levels. An inhibitory drug (LY294002) against PI3K that induces the phosphorylation of Akt (FIG. 19C) was used as a positive control, on the basis of the fact that the mRNA expression of VEGF is induced by the activation of the PI3K/Akt signal transduction pathway.

Example 8

Effect of ANT2 shRNA on the Expression and Activity of MMPs

In this example, it was found that the knockdown of ANT2 by shRNA in the human breast cancer cell line SK-BR3 decreases the Akt activity (suppression of PI3K/Akt signal transduction pathway) to degrade ECM (extracellular matrix), thus down-regulating MMPs (Matrix metalloproteinases), which are involved in the migration and invasion of cancer cells.

Among MMPs, MT1-MMP, known to be controlled in expression by VEGF, and MMP2 and MMP9, both known as being controlled in activity by MT1-MMP, were examined for expression and activity.

First, the breast cancer cell line SK-BR3 transfected with ANT2 shRNA was found to decrease in the mRNA level of MT1-MMP, which is responsible for the degradation of ECM (extracellular matrix), as measured by RT-PCR (FIG. 20A), and also in the protein level, as measured by Western blotting (FIG. 20B). Furthermore, ANT2 shRNA was re-confirmed to decrease the mRNA expression of MT1-MMP. In this regard, when a PI3K-overexpressing vector [wild-type PI3K/p110 vector (provided by Dr. Karin Reif)] was introduced to artificially activate the PI3K/Akt signal transduction pathway, MT1-MMP was observed to be recovered in mRNA level, as measured by RT-PCR (FIG. 21A), and in protein level, as measured by Western blotting (FIG. 21B).

In addition, RT-PCR showed that the introduction of ANT2 shRNA into the breast cancer cell line SK-BR3 decreased the level of MMP2 mRNA and MMP9 mRNA, both controlled by MT1-MMP (FIG. 22A). GAPDH mRNA was used as a loading control to show the uniform quantities of the mRNAs used because GAPDH remains constant irrespective of intra- and extracellular conditions. The introduction of ANT2 shRNA into the breast cancer cell line SK-BR3 was found to deactivate MMP2 and MMP9, both controlled by MT1-MMP, as measured by gelatin zymography. In the zymogram, the higher gelatinase activity of MMP2 and MMP9, which accounts for the greater population of the active forms of MMP2 and MMP9, allowed the appearance of more intensive white bands (FIG. 22B).

Example 9

Effect of ANT2 shRNA on the Migration and Invasion of Breast Cancer Cell Line into Other Tissues The introduction of ANT2 shRNA decreased the expression and activity of MMPs (matrix metalloproteinases), which are responsible for the migration and invasion of tumor cells, as demonstrated in Example 4. The following experiment was performed to quantitatively examine the reduction in the migration and invasion capacity of tumor cells.

In detail, to confirm that ANT2 shRNA can decrease the ability of tumor cells to migrate and invade, a matrigel invasion assay and a transwell migration assay were performed. A matrigel invasion assay is to analyze the invasion ability of tumor cells by staining the cells which degrade and proceed through matrigel. Specifically, the human breast cancer cell line SK-BR3 which was transfected with ANT2 shRNA was incubated for 18 hours. After that, 100 μl of 0.1% BSA, α-MEM containing $2\times10^4$ cells therein was put in an upper side of chamber (Becton Dickinson Labware, USA), followed by incubation. 24 hours later, the medium was removed from the upper side of the chamber, and the cells were washed three times with PBS and taken with a cotton swab. The cells which passed through the matrigel and adhered to the outside bottom of the well were fixed for 10 min with 10% formalin and stained for 20 min with 0.1% crystal violet. Stained cells were counted under a microscope. Separately, a transwell migration assay was utilized to examine the migration ability of tumor cells. The lower side of a transwell insert with a 8 μm pore size (Corning) was coated with gelatin (Sigma) before a cell suspension was placed into the transwell insert. At this time, a serum-free medium containing bFGF (Sigma) at a concentration of 10 ng/mL was put in the external vessel. After incubation for a predetermined time (18 hours), the inside of the insert was wiped with a cotton swab to take endothelial cells which did not migrate. The cells which migrated into the lower layer were stained with a Diff-Quick solution and counted under a 200× microscopic sight.

Figure 23:
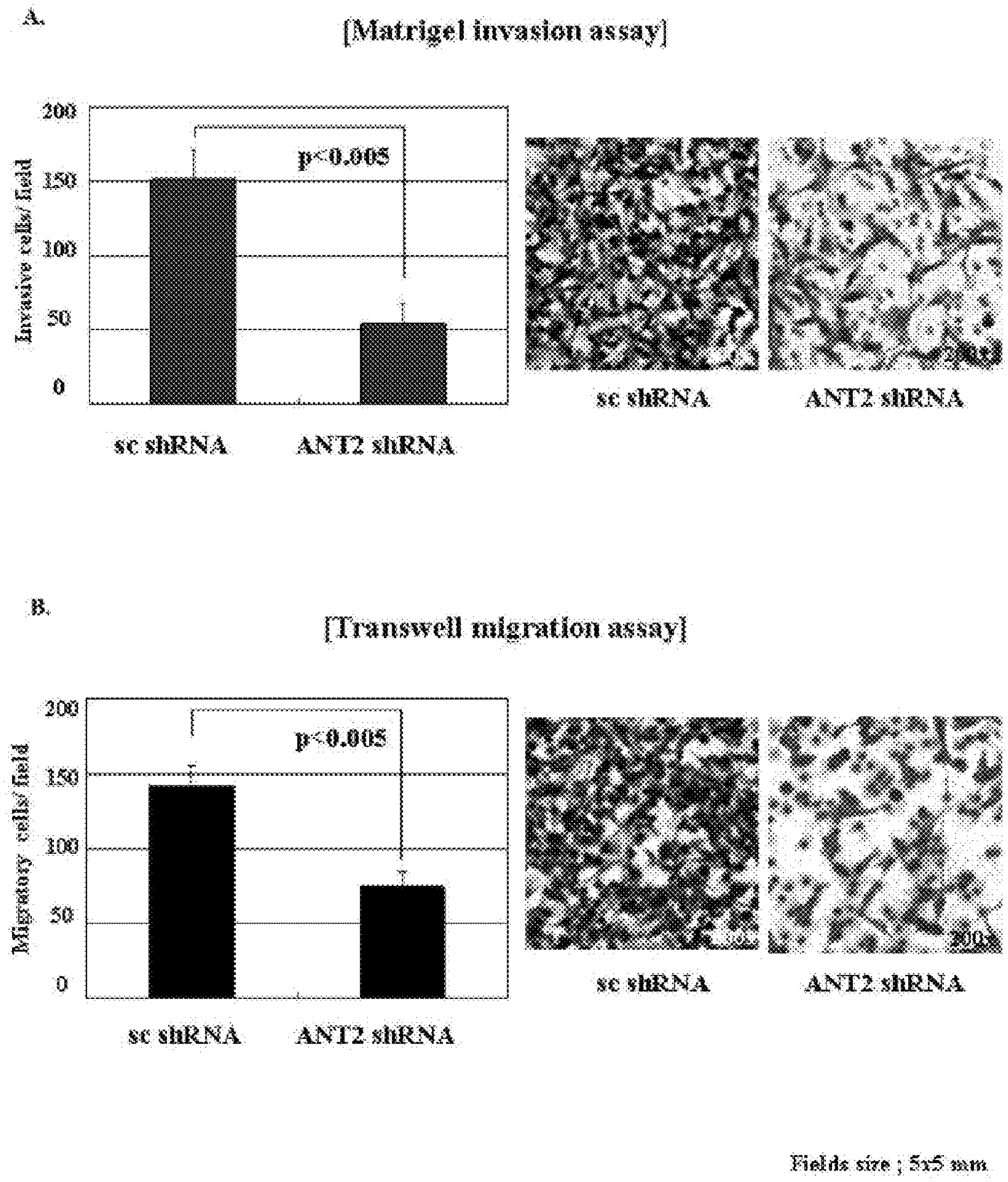

When ANT2 shRNA was introduced, the cells which passed through the matrigel and transwells and thus were stained were decreased in count, indicating that the invasion and migration ability of tumor cells was weakened (FIG. 23).

Example 10

Effect of ANT2 shRNA on Sensitivity to TRAIL

Breast cancer cell lines transfected with ANT2 shRNA were examined for reactivity to TRAIL (cancer cell death).

As breast cancer cell lines in this experiment, MCF7 resistant to TRAIL, and MDA-MB-231 highly sensitive to TRAIL were employed. MCF7 and MDA-MB-231 were treated with TRAIL at various concentrations after which cell death was analyzed with a CCK8 reagent. The CCK8 assay is a cell viability assay. Specifically, 100 μL of a cell suspension was placed onto each well ($1\times10^4$ cells/well). The cells were treated with 10-fold serial dilutions of TRAIL starting from 1 μg/mL to zero, followed by incubation for 12 hrs. After the addition of 10 μL of the CCK8 reagent, the cells were incubated for a proper time (4 hours) in a $CO_2$ incubator and measured for absorbance at 450 nm to analyze cell death.

TRAIL induced MDA-MB-231 cells to undergo apoptisis by TRAIL whereas the TRAIL-mediated apoptosis did not work for MCF7 cells (FIG. 24A). In this method, only viable cells showed a color change with the CCK8 reagent, which was detected at a certain wavelength.

When TRAIL was added at a concentration of as high as 100 ng/mL, MCF7 cells, which are resistant to TRAIL, were not induced to undergo apoptosis. However, the introduction of ANT2 shRNA into MCF7 cells induced apoptosis (~25%). In combination with TRAIL, ANT2 shRNA was found to induce more potential apoptosis (~65%) as measured by the CCK8 reagent (FIG. 24B). Also, the introduction of ANT2 shRNA was observed to decrease the intracellular protein level of ANT2 as measured by Western blotting. As for a negative control, it was PBS for TRAIL, and sc shRNA (scrambled shRNA) for ANT2 shRNA.

After being treated with TRAIL alone, ANT2 shRNA alone, and TRAIL and ANT2 shRNA in combination, MCF7 cells, resistant to TRAIL, were examined for apoptosis, and the results are shown in FIG. 24C. As shown in FIG. 24C, the strongest apoptosis was induced by a combination of ANT2 shRNA and TRAIL.

The same results as MCF7 were detected from the breast cancer cell lines T47D and BT474, both known to be resistant to TRAIL (FIG. 25A). For this, a CCK8 assay was employed to quantify the apoptosis.

The increased sensitivity to TRAIL was reconfirmed to be attributed to the knockdown of ANT2 by shRNA. In this context, when an ANT2-overexpressing vector (pcDNA-ANT2) was used to artificially overexpress ANT2, TRAIL-mediated apoptosis was found to be reduced as measured by a CCK8 assay (FIG. 25B). The empty vector pcDNA was introduced as a negative control for pcDNA-ANT2. When ANT2 shRNA increased sensitivity to TRAIL to induce apoptosis, the concurrent events of intracellular proteins (cleavage of PARP protein, cleavage of caspase-8/9/7, and truncation of Bid proteins) were detected by Western blots.

Because mitochondria play an important role in the regulation of apoptosis, cytochrome C, which is released from mitochondria to cytoplasm, was quantitatively monitored upon the ANT2 shRNA-triggered, TRAIL-mediated apoptosis. The mitochondrial protein COX IV was used as a loading control to guarantee the use of mitochondrial proteins in the same amount. No changes in the pattern of apoptosis-induced proteins were observed when TRAIL was used alone. Greater changes in the protein pattern were observed when the cells were treated with ANT2 shRNA in combination with TRAIL than ANT shRNA alone (FIG. 25C). These changes of intracellular protein patterns confirmed that ANT2 shRNA enhanced TRAIL-mediated apoptosis.

Example 11

Effect of ANT2 shRNA on the Expression of TRAIL Receptor

The breast cancer cell lines MCF7 and MDA-MB-231, which are different in sensitivity to TRAIL from each other, were analyzed for expression levels of the receptors DR4, DR5, DcR1, and DcR2, all binding to TRAIL, by Western blots.

When bound to TRAIL, DR4 and DR5 deliver normal apoptotic signals into the cells whereas DcR1 and DcR2 do not. Accordingly, higher sensitivity to TRAIL can be obtained by higher expression levels of DR4 and DR5 and lower expression levels of DcR1 and DcR2. As shown in FIG. 26A, MCF7 cells, which are low in sensitivity to TRAIL, are observed to have low levels of DR4 and DR5 and high levels of DcR1 and DcR2 while high levels of DR4 and DR5 and low levels of DcR1 and DcR2 were detected in MDA-MB-231 cells, which are high in sensitivity to TRAIL.

Upon the introduction of ANT2 shRNA, expression patterns of TRAIL receptors were examined, and the results are given in FIG. 26B. As shown in FIG. 26B, the introduction of ANT2 shRNA up-regulated DR4 and DR5, and down-regulated DcR1 and DcR2. In T47D and BT474 cell lines, which are known to have TRAIL resistance, the same effects as in MCF7 were observed. That is, the introduction of ANT2 shRNA increased the expression of DR4 and DR5, but decreased the expression of DcR1 and DcR2 (FIG. 26C).

Example 12

Effect of ANT2 shRNA on p53 Activity

An experiment was conducted to reveal the mechanism in which ANT2 shRNA up-regulates DR4 and DR5. On the basis of the report that the tumor suppressor protein p53 induces the expression of DR4 and DR5, the introduction of ANT2 shRNA was examined to determine whether it increases the expression of p53 and the level of phosphorylated p53. p53 and phosphoryated p53 were quantitatively measured [anti-Thr81 phospho-p53 and anti-p53 antibodies (Santa Cruz Biotechnology, Heidelberg, Germany)].

As shown in FIG. 27A, the introduction of ANT2 shRNA up-regulated p53 and increased the activity of p53.

A reporter gene assay showed that the up-regulation of p53 by ANT2 shRNA is attributed to increased affinity for the promoter of p53. This assay is generally designed in such a manner that when a certain protein binds to DNA to induce the expression of a gene of interest, the reporter is concurrently expressed and quantitatively analyzed by absorbance. In detail, cells were co-transfected with ANT2 shRNA and a pGL-p53 binding site-luciferase expression vector, and incubated for a certain period of time. A substrate was reacted with the expressed luciferase to measure the activity of the luciferase using a luminometer (FB12 luminometer; Berthold Detection Systems, Pforzheim, Germany).

As shown in FIG. 27B, the introduction of ANT2 shRNA induced a significant increase in the expression of the reporter gene fused with p53. sc shRNA (scrambled shRNA), which was designed to have no influence on the expression of mRNAs, was used as a negative control for ANT2 shRNA. The data indicate that ANT2 shRNA increases the gene expression inducting ability of p53.

In addition, an experiment was performed to reconfirm that the introduction of ANT2 shRNA induces the expression and activity of p53, thus up-regulating the TRAIL receptors DR4 and DR5. As shown in FIG. 27C, pre-treatment with the p53 inhibitor (pifithrin-alpha: Biovision, Zürich, Switzerland) suppressed the up-regulation of DR4 and DR5 by ANT2 shRNA (Western blots).

Furthermore, treatment with the p53 inhibitor (pifithrin-alpha) suppressed the up-regulation of TRAIL-mediated apoptosis by ANT2 shRNA, which confirmed that the introduction of ANT2 shRNA induced the expression and activity of p53, leading to an increase in sensitivity to TRAIL. The cell death was quantified using a CCK8 assay, with the use of PBS as a negative control for the p53 inhibitor (FIG. 28).

As is apparent from the data, the introduction of ANT2 shRNA into breast cancer cell lines increases the activity of p53, ultimately resulting in the up-regulation of DR4 and DR5 on cell surfaces.

Example 13

In Vivo Assay of ANT2 shRNA for Ability to Suppress Tumor Growth by Increasing Sensitivity to TRAIL An animal test was conducted to examine whether ANT2 shRNA suppresses tumor growth by activating the TRAIL-mediated apoptosis.

The breast cancer cell line MCF7 resistant to TRAIL was transplanted into immunedeficient Balb/c nude mice. When a tumor grew to a volume of 100 $mm^3$, they were treated with ANT2 shRNA and TRAIL. In this regard, TRAIL was intraperitoneally injected (10 mg/kg) while ANT2 shRNA was directly injected into the tumor (100 μg; supplemented 200 μl Lipofectamine™2000). At this time, Lipofectamine™2000 was used to deliver ANT2 shRNA into tumor cells. After three treatments over 45 days, the size of tumor was monitored. A same volume of PBS and sc shRNA was used as respective negative controls for TRAIL and sc shRNA.

As shown in FIG. 29A, TRAIL alone had no significant influences on tumor growth, as in the cell culture tests. ANT2 alone was observed to suppress tumor growth. However, the greatest suppressive effect on tumor growth was obtained when the animal was treated ANT2 shRNA and TRAIL at the same time.

On 45th day, the animal models were subjected to euthanasia and the tumors were excised. The expression patterns of TRAIL receptors in the tumor cells were examined using RT-PCR, and the results are given in FIG. 29B.

As shown in FIG. 29B, the introduction of ANT2 shRNA up-regulated DR4 and DR5, but down-regulated DcR2.

The data imply that the TRAIL-mediated tumor suppression by ANT2 shRNA is attributed to the expression control of TRAIL receptors.

<Construction of ANT2 shRNA Adenovirus>

Adenovirus system was used for the effective tranfection of progenitor cells with ANT2 shRNA (ANT2 shRNA sequence and loop sequence targeting ANT2 are the same as sequences used in the construction of ANT2 shRNA expression vector).

To construct a recombinant adenovirus, the pSilencer-ANT2shRNA DNA was subcloned into the EcoRI/HindIII site of the Pca14 shuttle vector, which is designed to facilitate cloning into an adenovirus vector. A real-clone was detected by PvuI enzyme mapping (DNA was enzymatically digested and electrophoresed to detect a DNA fragment at a suitable size position). Within the BJ5183 competent cell (an *E. coli* strain allowing the homologous recombination between an adenovirus vector and a shuttle vector DNA), a Pca14-mANT2shRNA DNA linearized by PcaI was subjected to homologous recombination with an adenovirus-d1324 vector (E1 deleted: replication-defective vector) DNA linearized by BstBI. The resulting recombinant DNA was transformed into DH5α cells and amplified. After being detected, a real-clone was transfected into a 293a packaging cell (a cell designed to readily introduce DNA thereinto, and to allow the mass production of cloned adenovirus therein due to the presence of the adenoviral replication gene E1) to induce the proliferation of adenovirus within the cell. Thus, the enriched adenovirus-mANT2shRNA was separated to purity using a PEG-CsCl (density gradient layer separation) method before use in experiments.

Example 14

Effect of ANT2 shRNA on the Progenitor Cells of Breast Cancer Cell Line

A breast cancer cell line is composed of progenitor cells and non-progenitor cells. ANT2 protein is highly expressed in both cell populations. In this example, apoptosis according to the introduction of ANT2 shRNA was examined in both cell populations.

The progenitor cells of a tumor are characterized by CD44+/CD24− on their surface. Of the breast cancer cell lines, MDA-MB-231 is composed predominantly of progenitor cells (CD44+/CD24−) (more than 80%), while MCF7 contains a minor proportion (less than 10%) of progenitor cells.

The two cell lines and the progenitor cells (CD44+/CD24−) separated therefrom were analyzed for ANT2 gene expression using RT-PCR. Real-time PCR was also used to confirm the results of RT-PCR. The two cell lines were treated with an CD44 monoclonal antibody [anti-PE-conjugated CD44 monoclonal antibody (BD-PharMingen, San Diego, Calif., USA) and anti-PE microbeads (MiltenyiBiotec. BergischGladbach, Germany), followed by sorting necessary cells with the aid of MACS (Magnetic Activating cell sorter). The sorted cells and the non-sorted cells of progenitor cells were analyzed for ANT2 mRNA level using RT-PCR and real-time PCR.

Figure 30:
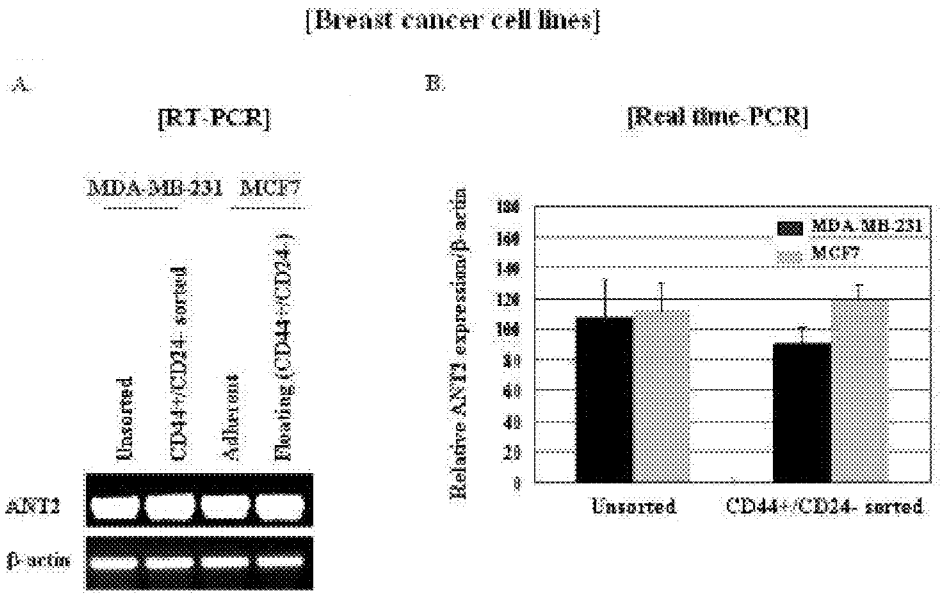

As shown in FIG. 30, both cell lines, whether sorted into the progenitor cells (CD44+/CD24−) or not, were high in ANT2 expression level. These results imply that the down regulation of ANT2 by shRNA can induce apoptosis in both the progenitor cells and the non-progenitor cells, thus enhancing the therapeutic possibility.

In addition, an experiment was conducted to show the ability of ANT2 shRNA to induce the progenitor cells (CD44+/CD24−) of the breast cancer cell to undergo apoptosis. As a cell system for this experiment, mesenchymal cells artificially converted from a normal breast epithelial cell line (MCF10A) by suppressing E-cadherin were employed. The mesenchymal cells are known to show the characteristics of breast cancer stem cells.

Upon the knockdown of E-cadherin by shRNA in the normal breast epithelial cell (MCF10A), as shown in FIG. 31A, the cells which had normally grown in a densely adherent pattern changed to show a loosely adherent growth pattern, which indicates the conversion of the normal epithelial cells into mesenchymal cells. At this time, the cells were found to increase in E-cadherin expression and decrease in ANT2 expression, as measured by RT-PCR (FIG. 31B).

Further, ANT2 shRNA was introduced into only the progenitor cells (CD44+/CD24−) separated from the breast cancer cell lines MDA-MB-231 and MCF7, after which apoptosis was analyzed using FACS with Annexin V-FITC and PI staining. This assay is based on the fact that when cells are dead, intracellular proteins and DNA are released from the cells (CD44+/CD24−) and reacted with Annexin V-FITC and PI, respectively. The results are given in FIG. 32. Even the progenitor cells separated from the two tumor cell lines were observed to be effectively induced to undergo apoptosis by ANT2 shRNA. For this, sc shRNA was used as a negative control.

Figure 33:
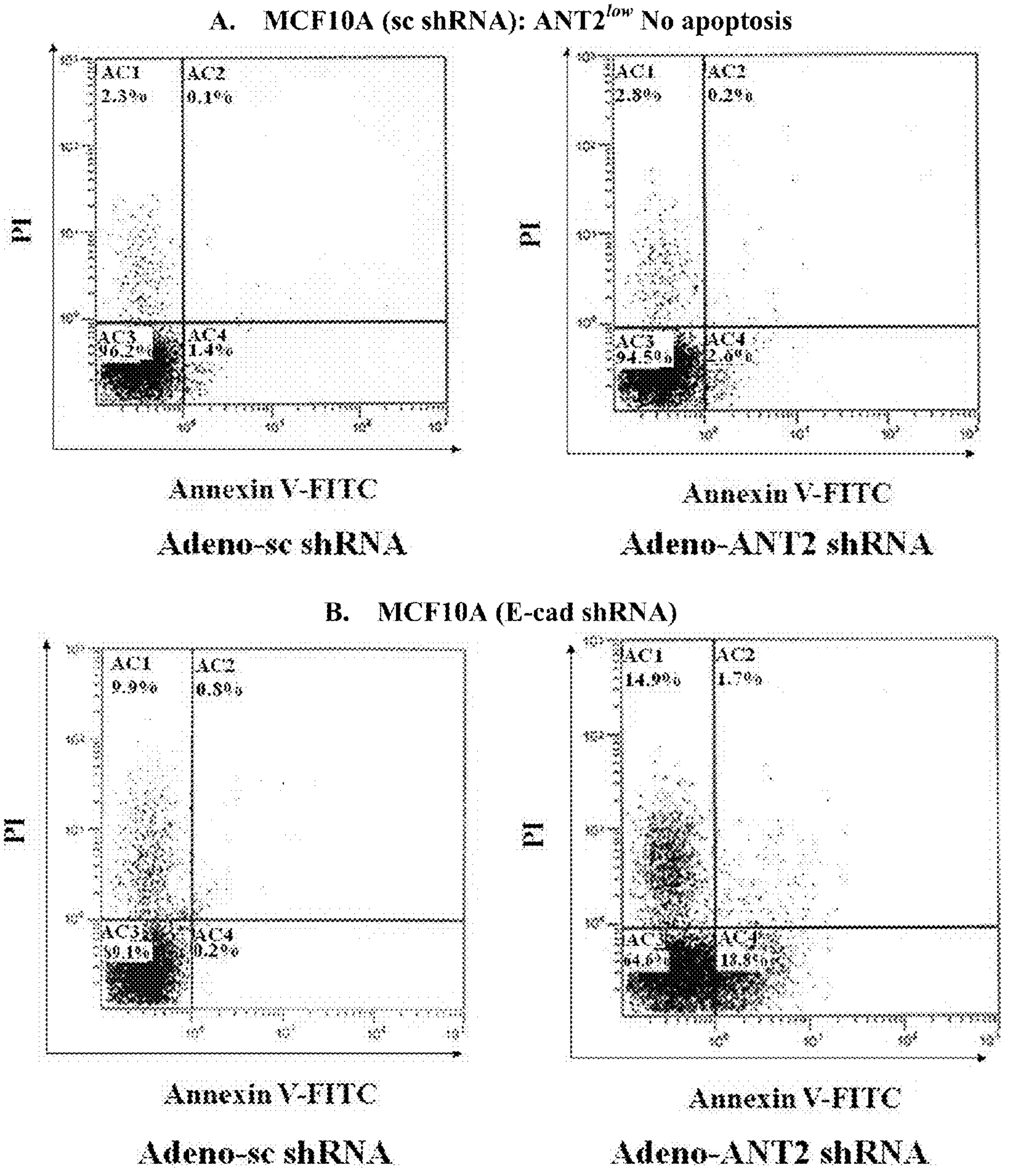

Furthermore, ANT2 shRNA was examined to determine whether it can induce effective apoptosis in the breast cancer stem-like cells obtained by introducing E-cadherin shRNA into the normal breast epithelial cell line (MCF10A). The results are given in FIG. 33. For analysis, the cells were stained with annexin-V-FITC and PI. This is based on the fact that cell membranes at an early stage of programmed cell death are destroyed to release phospholipids such as phosphatydylserine from the cells and Annexin V is associated with the phospholipids, which is used as a proof for the early stage of programmed cell death. As for PI (propium iodide), it binds DNA by intercalating between bases and is a fluorescent molecule that can be used to stain DNA. It is used to determine cell death on the basis of nuclear blebs and condensation upon apoptosis. The normal breast epithelial cell line (MCF10A) was used as a negative control for this experiment. Even when ANT2 shRNA was introduced, little apoptosis was induced in the normal breast epithelial cell line (MCF10A) having low level of ANT2 expression (FIG. 33A). On the other hand, the meshechymally transdifferentiated cells obtained by introducing E-cadherin shRNA into MCF10A were improved in ANT2 expression level and, when ANT2 shRNA was introduced thereinto, the cells (E-cad shRNA transfected-MCF10A) were effectively induced to undergo apoptosis (FIG. 33B).

The results indicate that ANT2 shRNA can effectively kill breast cancer stem cells without influence on normal epithelial cells.

Example 15

Effect of ANT2 shRNA on Tumor Growth Activity of Progenitor Cells

An experiment was performed to examine the effect of ANT2 shRNA on the tumor growth activity of the progenitor cells of breast cancer. In detail, only progenitor cells (CD44+/CD24−), which act as a source of tumor recurrence, were isolated from the breast cancer cell lines MDA-MB-231 and MCF7 (in the same manner as in Example 10) and transfected with ANT2 shRNA, after which they were cultured in non-adherent culture dishes (the attachment of cell to culture was minimized to promote the formation of cell mass) to observe the formation of cell mass.

As shown in FIG. 34A, a large number of cell masses were formed when ANT2 shRNA was not introduced whereas the introduction of ANT2 shRNA allowed the formation of almost no or few cell masses. In addition, as shown in FIG. 34B, the cell masses, although formed, were very small in volume.

These results indicate that ANT2 shRNA inhibits the tumor growth activity of the progenitor cells which play a crucial role in the recurrence of tumor.

Example 16

Effect of ANT2 shRNA on Drug Resistance of Progenitor Cells

The progenitor cells of breast cancer (CD44+/CD24−) exhibit high resistance to drugs (anti-cancer agents). The effect of ANT2 shRNA on the sensitivity of progenitor cells to drugs was examined.

The MDA-MB-231 cell line which has a predominant proportion of progenitor cells (CD44+/CD24−) was treated with 10-fold serial dilutions of doxorubicin, a widely used anti-cancer agent starting from 10 μM to zero, followed by incubation (10 hrs). The apoptosis was quantitatively analyzed using a CCK8 assay and the results are given in FIG. 35. The assay was conducted in the same manner as in Example 6.

As shown in FIG. 35, neither progenitor cells (CD44+/CD24−) nor the non-progenitor cells were sensitive to doxorubicin. In contrast, both cells, when transfected with ANT2 shRNA, were induced to undergo apoptosis in a dose-dependent pattern.

The breast cancer cell line MCF7, which has a minor proportion of progenitor cells (CD44+/CD24−), was treated with various concentrations of doxorubicin, widely used for the treatment of breast cancer, after which apoptosis was quantitatively analyzed using a CCK8 assay. The results are given in FIG. 36. As shown in FIG. 36, the progenitor cells (CD44+/CD24−) were less sensitive to doxorubicin than was a mixed population of the progenitor cells and the non-progenitor cells. On the other hand, the introduction of ANT2 shRNA was found to induce apoptosis in a dose-dependent manner in both cell populations. The results indicate that the introduction of ANT2 shRNA makes the cells more sensitive to doxorubicin, giving a solution to the problem of drug resistance.

Example 17

Effect of ANT2 shRNA on the Expression of the Receptor ABCG2 Responsible for Drug Resistance of Progenitor Cells One of the representative reasons for the high resistance, that is, the low sensitivity of the progenitor cells of breast cancer to drugs is the overexpression of the MDR (multi-drug resistance receptors), which are located in the cell membranes, functioning to transport drugs from cells to the exterior. Representative among the receptors is ABCG2 which is highly expressed particularly in breast cancer cells.

The following experiments were conducted to examine whether the enhancement of drug sensitivity by ANT2 shRNA is attributed to the control of the expression and activity of ABCG2.

The breast cancer cell lines MDA-MB-231 and MCF7, which have high and low proportions of the progenitor cells (CD44+/CD24−), respectively, were used in this experiment. Progenitor cells (CD44+/CD24−) sorted from the breast cancer cells lines, unsorted cells, and the mesenchymally trans-differentiated-breast epithelial cell line (MCF10A) by the knockdown of E-cadherin were analyzed for ABCG2 mRNA expression using RT-PCR. In addition, ABCG protein levels were determined by Western blotting with an anti-ABCG2 antibody (Santa Cruz Biotechnology, Inc., Santa Cruz, Calif., USA).

As shown in FIG. 37, the mRNA expression level of ABCG2 is increased in progenitor cells (CD44+/CD24−) sorted from the two tumor cell lines, non-sorted cells, and the mesenchymally transdifferentiated-breast epithelial cell line (MCF10A) by the knockdown of E-cadherin.

As shown in FIG. 38, the protein expression level of ABCG2 is increased in progenitor cells (CD44+/CD24−) sorted from the two tumor cell lines, non-sorted cells, and the mesenchymally transdifferentiated-breast epithelial cell line (MCF10A) by the knockdown of E-cadherin. In addition, the increased level of ABCG2 was observed to be reduced when ANT2 shRNA was introduced. The results indicate that breast cancer progenitor cells and breast cancer stem cells, both expressing a high level of ABCG2, can be reduced in ABCG2 expression by the introduction of ANT2 shRNA thereinto.

Furthermore, the progenitor cells of breast cancer were examined to determine if there was a practical increase in the activity of ABCG2. In detail, progenitor cells (CD44+/CD24−) sorted from the breast cancer cells lines MDA-MB-231 and MCF7, unsorted cells, and the mesenchymally trans-differentiated-breast epithelial cell line (MCF10A) by the knockdown of E-cadherin were analyzed for ABCG2 activity using Hoechst 33342. The extent of accumulation of Hoechst 33342 gives a quantitative index for the activity of ABCG2. The results are given in FIG. 39.

As shown in FIG. 39, ABCG2 activity is increased in progenitor cells (CD44+/CD24−) sorted from the two tumor cell lines, non-sorted cells, and the mesenchymally transdifferentiated-breast epithelial cell line (MCF10A) by the knockdown of E-cadherin.

On the basis of the results obtained above, the effect of ANT2 shRNA on the activity of ABCG2 was examined. To this end, the cells were treated with Hoechst 33342 (Sigma), followed by fluorescent excited cells sorting to quantitatively analyze the activity of ABCG2. The results are given in FIG. 40. As shown in FIG. 40, the activity of ABCG2 was effectively decreased by ANT2 shRNA.

These results indicate that when the progenitor cells of breast cancer, which show high expression levels and activity of the receptor ABCG2 involved in drug resistance, are transfected with ANT2 shRNA, the expression and activity of ABCG2 are decreased. That is, ANT2 shRNA reduces the activity of ABCG2 in the progenitor cells of breast cancer, giving a solution to the problem of drug resistance.

Example 18

Selective Delivery of ANT2 shRNA to Breast Cancer Progenitor Cells and Apoptotic Effect Thereof An experiment was conducted to examine whether ANT2 shRNA can effectively kill progenitor cells of breast cancer. When patients with breast cancer are treated by using ANT2 shRNA, it is very important to effectively deliver ANT2 shRNA to target cells. In this experiment, nano-complexes [PEI/hyaluronic acid (HA) nano-complexes] were prepared to use as a delivery material targeting CD44 which is highly expressed on the progenitor cells of breast cancer. To examine whether ANT2 shRNA can be effectively delivered to the breast cancer cell lines MDA-MB-231 and T47D, which express CD44 at a high and a low level, respectively, fluorescence-conjugated nanoparticle [PEI/hyaluronic acid (HA) nano-complexes] was complexed with ANT2 shRNA. The resulting nano-complexes were applied to each cell line and then incubated, followed by analyzing intracellular fluorescent intensity to determine the level of the ANT2 shRNA introduced into the cells.

As shown in FIG. 41, the selective delivery of the gene of interest to the cell line MDA-MB-231 expressing CD44 at high levels was highly effective.

The data indicate that with the aid of the delivering nano-complexes[PEI/hyaluronic acid (HA) nano-complexes] targeting CD44 which is highly expressed on the surface of the progenitor cells of breast cancer, ANT2 shRNA can be selectively delivered to the progenitor cells and induce the cells to undergo apoptosis.

It is understood to a person skilled in the art that the above description of the present invention is susceptible to various modifications, changes and adaptations, and the same are intended to be comprehended within the meaning and range of equivalents of the appended claims. Therefore, the embodiments and attached drawings disclosed in the present invention are not intended to limit the technical spirit of the present invention, but are intended to describe the invention. The technical spirit of the present invention is not limited to such embodiments and drawings.

INDUSTRIAL APPLICABILITY

The present invention relates to gene therapy for cancer using small interfering RNA (siRNA) specifically binding to adenine nucleotide translocator 2 (ANT2). The ANT2 siRNA containing expression vector induces directly or indirectly the decrease of ATP production necessary for tumor cell growth and the increase of TNF-α and its receptor productions involved in apoptosis. Therefore, the expression vector can significantly suppress tumor growth in mouse models transplanted with cultured cancer cells exhibiting high level of ANT2. In conclusion, the expression vector containing ANT2 siRNA can be effectively used for gene therapy for cancer independently or together with other cancer treatment methods.

SEQUENCE LISTING

SEQ ID NO: 1 is the polynucleotide sequence of ANT2 gene.

SEQ ID NO: 2 is the target sequence of ANT2 siRNA-1.

SEQ ID NO: 3 is the loop sequence of ANT2 shRNA.

SEQ ID NO: 4 is the polynucleotide sequence of a forward primer for the amplification of ANT1 gene.

SEQ ID NO: 5 is the polynucleotide sequence of a reverse primer for the amplification of ANT1 gene.

SEQ ID NO: 6 is the polynucleotide sequence of a forward primer for the amplification of ANT2 gene.

SEQ ID NO: 7 is the polynucleotide sequence of a reverse primer for the amplification of ANT2 gene.

SEQ ID NO: 8 is the polynucleotide sequence of a forward primer for the amplification of Bcl-xL gene.

SEQ ID NO: 9 is the polynucleotide sequence of a reverse primer for the amplification of Bcl-xL gene.

SEQ ID NO: 10 is the polynucleotide sequence of a forward primer for the amplification of Bax gene.

SEQ ID NO: 11 is the polynucleotide sequence of a reverse primer for the amplification of Bax gene.

SEQ ID NO: 12 is the polynucleotide sequence of a forward primer for the amplification of β-actin gene.

SEQ ID NO: 13 is the polynucleotide sequence of a reverse primer for the amplification of β-actin gene.

SEQ ID NO: 14 is the target sequence of ANT2 siRNA-2.

SEQ ID NO: 15 is the target sequence of ANT2 siRNA-3.

SEQ ID NO: 16 is the sense sequence of ANT2 shRNA.

SEQ ID NO: 17 is the anti-sense sequence of ANT2 shRNA.

SEQ ID NO: 18 is recombinant expression vector polynucleotide sequence.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating a breast cancer comprising:

administering an effective amount of a pharmaceutical composition comprising adenine nucleotide translocator 2 (ANT2) small interfering RNA (siRNA) or adenine nucleotide translocator 2 (ANT2) short hairpin RNA (shRNA) as an active ingredient to a subject in need thereof, wherein the ANT2 siRNA or ANT2 shRNA induces degradation of ANT2 mRNA by interacting an anti-sense sequence represented by SEQ ID NO:17 with a sense sequence represented by SEQ ID NO:16.

2. The method of claim 1, wherein the pharmaceutical composition suppresses the expression of human epidermal growth factor receptor 2 (HER2/neu).

3. The method of claim 1, wherein the pharmaceutical composition enhances an effect of TNF-related apoptosis-inducing ligand (TRAIL) for treating the breast cancer.

4. The method of claim 3, wherein the pharmaceutical composition enhances an expression of death receptor 4 (DR4) and death receptor 5 (DR5) and suppresses an expression of death decoy receptor 1 (DcR1) and death decoy receptor 2 (DcR2).

5. The method of claim 3, wherein the pharmaceutical composition increases the expression and activity of p53 protein.

6. A method of treating stem cells of a breast cancer comprising:

treating the stem cells of breast cancers with a composition comprising adenine nucleotide translocator 2 (ANT2)

small interfering RNA (siRNA) or adenine nucleotide translocator 2 (ANT2) short hairpin RNA (shRNA), wherein the ANT2 siRNA or ANT2 shRNA induces degradation of ANT2 mRNA by interacting an anti-sense sequence represented by SEQ ID NO:17 with a sense sequence represented by SEQ ID NO:16.

7. The method of claim 6, wherein the stem cells of a breast cancer is in a patient and the composition is administered to the patient having a breast cancer.

8. The method of claim 6, wherein the composition inhibits expression and activity of ATP-binding cassette sub-family G member 2 (ABCG2).

9. The method of claim 6, further treating the stem cells with an anti-cancer agent, wherein the composition enhances the effect of the anti-cancer agent by improving the response of the stem cells to the anti-cancer agent and reducing development of tolerance toward the anti-cancer agent.

10. The method of claim 9, wherein the anti-cancer agent is doxorubicin or pharmaceutically acceptable salt thereof.

11. A method of inhibiting metastasis of breast cancer cells comprising:

administering an effective amount of a pharmaceutical composition comprising adenine nucleotide translocator 2 (ANT2) small interfering RNA (siRNA) or adenine nucleotide translocator 2 (ANT2) short hairpin RNA (shRNA) as an active ingredient to a subject in need thereof, wherein the ANT2 siRNA or ANT2 shRNA induces degradation of ANT2 mRNA by interacting an anti-sense sequence represented by SEQ ID NO:17 with a sense sequence represented by SEQ ID NO:16.

* * * * *

```
                          SEQUENCE LISTING

<160> NUMBER OF SEQ ID NOS: 18

<210> SEQ ID NO 1
<211> LENGTH: 1225
<212> TYPE: DNA
<213> ORGANISM: Homo sapiens
<220> FEATURE:
<223> OTHER INFORMATION: cDNA sequence of ANT2(adenine nucleotide
      translocator 2)

<400> SEQUENCE: 1

ccgcagcgcc ggagtcaaac ggttcccggc ccagtcccgt cctgcagcag tctgcctcct      60
```

```
ctttcaacat gacagatgcc gctgtgtcct tcgccaagga cttcctggca ggtggagtgg    120

ccgcagccat ctccaagacg gcggtagcgc ccatcgagcg ggtcaagctg ctgctgcagg    180

tgcagcatgc cagcaagcag atcactgcag ataagcaata caaaggcatt atagactgcg    240

tggtccgtat tcccaaggag cagggagttc tgtccttctg gcgcggtaac ctggccaatg    300

tcatcagata cttccccacc caggctctta acttcgcctt caaagataaa tacaagcaga    360

tcttcctggg tggtgtggac aagagaaccc agttttggcg ctactttgca gggaatctgg    420

catcgggtgg tgccgcaggg gccacatccc tgtgttttgt gtaccctctt gattttgccc    480

gtacccgtct agcagctgat gtgggtaaag ctggagctga aagggaattc cgaggcctcg    540

gtgactgcct ggttaagatc tacaaatctg atgggattaa gggcctgtac caaggcttta    600

acgtgtctgt gcagggtatt atcatctacc gagccgccta cttcggtatc tatgacactg    660

caaagggaat gcttccggat cccaagaaca ctcacatcgt catcagctgg atgatcgcac    720

agactgtcac tgctgttgcc gggttgactt cctatccatt tgacaccgtt cgccgccgca    780

tgatgatgca gtcagggcgc aaaggaactg acatcatgta cacaggcacg cttgactgct    840

ggcggaagat tgctcgtgat gaaggaggca aagctttttt caagggtgca tggtccaatg    900

ttctcagagg catgggtggt gcttttgtgc ttgtcttgta tgatgaaatc aagaagtaca    960

cataagttat ttcctaggat tttcccccct gtgaacaggc atgttgtatt ctataacaca   1020

atcttgagca ttcttgacag actcctggct gtcagtttct cagtggcaac tactttactg   1080

gttgaaaatg ggaagcaata atattcatct gaccagtttt cctctaaagc catttccatg   1140

atgatgatga tgggactcaa ttgtattttt tatttcagtc actcctgata aataacaaat   1200

ttggagaaat aaaaatatct aaaat                                          1225
```

<210> SEQ ID NO 2
<211> LENGTH: 19
<212> TYPE: RNA
<213> ORGANISM: Artificial Sequence
<220> FEATURE:
<223> OTHER INFORMATION: Target sequence of ANT2 siRNA-1

<400> SEQUENCE: 2
gcagaucacu gcagauaag 19

<210> SEQ ID NO 3
<211> LENGTH: 9
<212> TYPE: RNA
<213> ORGANISM: Artificial Sequence
<220> FEATURE:
<223> OTHER INFORMATION: Loop sequence of ANT2 shRNA

<400> SEQUENCE: 3 uucaagaga 9

<210> SEQ ID NO 4
<211> LENGTH: 20
<212> TYPE: DNA
<213> ORGANISM: Artificial Sequence
<220> FEATURE:
<223> OTHER INFORMATION: Forward primer for the ANT1

<400> SEQUENCE: 4
ctgagagcgt cgagctgtca 20

<210> SEQ ID NO 5
<211> LENGTH: 19
<212> TYPE: DNA

-continued

<213> ORGANISM: Artificial Sequence
<220> FEATURE:
<223> OTHER INFORMATION: Reverse primer for the ANT1

<400> SEQUENCE: 5
ctcaatgaag catctcttc 19

<210> SEQ ID NO 6
<211> LENGTH: 19
<212> TYPE: DNA
<213> ORGANISM: Artificial Sequence
<220> FEATURE:
<223> OTHER INFORMATION: Forward primer for the ANT2

<400> SEQUENCE: 6
ccgcagcgcc gtagtcaaa 19

<210> SEQ ID NO 7
<211> LENGTH: 20
<212> TYPE: DNA
<213> ORGANISM: Artificial Sequence
<220> FEATURE:
<223> OTHER INFORMATION: Reverse primer for the ANT2

<400> SEQUENCE: 7
agtctgtcaa gaatgctcaa 20

<210> SEQ ID NO 8
<211> LENGTH: 29
<212> TYPE: DNA
<213> ORGANISM: Artificial Sequence
<220> FEATURE:
<223> OTHER INFORMATION: Forward primer for the Bcl-xL

<400> SEQUENCE: 8
gaattcaaat gtctcagagc aaccgggag 29

<210> SEQ ID NO 9
<211> LENGTH: 30
<212> TYPE: DNA
<213> ORGANISM: Artificial Sequence
<220> FEATURE:
<223> OTHER INFORMATION: Reverse primer for the Bcl-xL

<400> SEQUENCE: 9
gcggccgcat tccgactgaa gagtgagccc 30

<210> SEQ ID NO 10
<211> LENGTH: 16
<212> TYPE: DNA
<213> ORGANISM: Artificial Sequence
<220> FEATURE:
<223> OTHER INFORMATION: Forward primer for the Bax

<400> SEQUENCE: 10
gacgggtccg gggagc 16

<210> SEQ ID NO 11
<211> LENGTH: 20
<212> TYPE: DNA
<213> ORGANISM: Artificial Sequence
<220> FEATURE:
<223> OTHER INFORMATION: Reverse primer for the Bax

<400> SEQUENCE: 11
cagcccatct tccagatggt 20

<210> SEQ ID NO 12
<211> LENGTH: 23
<212> TYPE: DNA
<213> ORGANISM: Artificial Sequence
<220> FEATURE:
<223> OTHER INFORMATION: Forward primer for the beta-actin

<400> SEQUENCE: 12
ggaaatcgtg cgtgacatta agg 23

<210> SEQ ID NO 13
<211> LENGTH: 22
<212> TYPE: DNA
<213> ORGANISM: Artificial Sequence
<220> FEATURE:
<223> OTHER INFORMATION: Reverse primer for the beta-actin

<400> SEQUENCE: 13
ggcttttagg atggcaaggg ac 22

<210> SEQ ID NO 14
<211> LENGTH: 19
<212> TYPE: RNA
<213> ORGANISM: Artificial Sequence
<220> FEATURE:
<223> OTHER INFORMATION: Target sequence of ANT2 siRNA-2

<400> SEQUENCE: 14
cugacaucau guacacagg 19

<210> SEQ ID NO 15
<211> LENGTH: 19
<212> TYPE: RNA
<213> ORGANISM: Artificial Sequence
<220> FEATURE:
<223> OTHER INFORMATION: Target sequence of ANT2 siRNA-3

<400> SEQUENCE: 15
gauugcucgu gaugaagga 19

<210> SEQ ID NO 16
<211> LENGTH: 21
<212> TYPE: RNA
<213> ORGANISM: Artificial Sequence
<220> FEATURE:
<223> OTHER INFORMATION: Sense sequence of ANT2 shRNA

<400> SEQUENCE: 16
gcagaucacu gcagauaagu u 21

<210> SEQ ID NO 17
<211> LENGTH: 21
<212> TYPE: RNA
<213> ORGANISM: Artificial Sequence
<220> FEATURE:
<223> OTHER INFORMATION: Anti-sense sequence of ANT2 shRNA

<400> SEQUENCE: 17
aacuuaucug cagugaucug c 21

<210> SEQ ID NO 18
<211> LENGTH: 4121
<212> TYPE: DNA
<213> ORGANISM: Artificial Sequence
<220> FEATURE:
<223> OTHER INFORMATION: pSilencerTM 3.1-H1 puro plasmids for DNA
vector-based siRNA synthesis

<400> SEQUENCE: 18
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt catatttgca tgtcgctatg 420
tgttctggga aatcaccata aacgtgaaat gtctttggat ttgggaatct tataagttct 480
gtatgagacc actcggatcc actaccgttg ttataggtgt tcaagagaca cctataacaa 540
cggtagtttt ttggaaaagc ttggcgtaat catggtcata gctgtttcct gtgtgaaatt 600
gttatccgct cacaattcca cacaacatac gagccggaag cataaagtgt aaagcctggg 660
gtgcctaatg agtgagctaa ctcacattaa ttgcgttgcg ctcactgccc gctttccagt 720
cgggaaacct gtcgtgccag ctgcattaat gaatcggcca acgcgcgggg agaggcggtt 780
tgcgtattgg gcgctcttcc gcttcctcgc tcactgactc gctgcgctcg gtcgttcggc 840
tgcggcgagc ggtatcagct cactcaaagg cggtaatacg gttatccaca gaatcagggg 900
ataacgcagg aaagaacatg tgagcaaaag gccagcaaaa ggccaggaac cgtaaaaagg 960
ccgcgttgct ggcgtttttc cataggctcc gcccccctga cgagcatcac aaaaatcgac 1020
gctcaagtca gaggtggcga aacccgacag gactataaag ataccaggcg tttccccctg 1080
gaagctccct cgtgcgctct cctgttccga ccctgccgct taccggatac ctgtccgcct 1140
ttctcccttc gggaagcgtg gcgctttctc atagctcacg ctgtaggtat ctcagttcgg 1200
tgtaggtcgt tcgctccaag ctgggctgtg tgcacgaacc ccccgttcag cccgaccgct 1260
gcgccttatc cggtaactat cgtcttgagt ccaacccggt aagacacgac ttatcgccac 1320
tggcagcagc cactggtaac aggattagca gagcgaggta tgtaggcggt gctacagagt 1380
tcttgaagtg gtggcctaac tacggctaca ctagaagaac agtatttggt atctgcgctc 1440
tgctgaagcc agttaccttc ggaaaaagag ttggtagctc ttgatccggc aaacaaacca 1500
ccgctggtag cggtggtttt tttgtttgca agcagcagat tacgcgcaga aaaaaaggat 1560
ctcaagaaga tcctttgatc ttttctacgg ggtctgacgc tcagtggaac gaaaactcac 1620
gttaagggat tttggtcatg agattatcaa aaaggatctt cacctagatc cttttaaatt 1680
aaaaatgaag ttttaaatca atctaaagta tatatgagta aacttggtct gacagttacc 1740
aatgcttaat cagtgaggca cctatctcag cgatctgtct atttcgttca tccatagttg 1800
cctgactccc cgtcgtgtag ataactacga tacgggaggg cttaccatct ggccccagtg 1860
ctgcaatgat accgcgagac ccacgctcac cggctccaga tttatcagca ataaaccagc 1920
cagccggaag ggccgagcgc agaagtggtc ctgcaacttt atccgcctcc atccagtcta 1980
ttaattgttg ccgggaagct agagtaagta gttcgccagt taatagtttg cgcaacgttg 2040
ttgccattgc tacaggcatc gtggtgtcac gctcgtcgtt tggtatggct tcattcagct 2100
ccggttccca acgatcaagg cgagttacat gatcccccat gttgtgcaaa aaagcggtta 2160
gctccttcgg tcctccgatc gttgtcagaa gtaagttggc cgcagtgtta tcactcatgg 2220
ttatggcagc actgcataat tctcttactg tcatgccatc cgtaagatgc ttttctgtga 2280
ctggtgagta ctcaaccaag tcattctgag aatagtgtat gcggcgaccg agttgctctt 2340

-continued

```
gcccggcgtc aatacgggat aataccgcgc cacatagcag aactttaaaa gtgctcatca   2400
ttggaaaacg ttcttcgggg cgaaaactct caaggatctt accgctgttg agatccagtt   2460
cgatgtaacc cactcgtgca cccaactgat cttcagcatc ttttactttc accagcgttt   2520
ctgggtgagc aaaaacagga aggcaaaatg ccgcaaaaaa gggaataagg gcgacacgga   2580
aatgttgaat actcatactc ttcctttttc aatattattg aagcatttat cagggttatt   2640
gtctcatgag cggatacata tttgaatgta tttagaaaaa taaacaaata ggggttccgc   2700
gcacatttcc ccgaaaagtg ccacctattg gtgtggaaag tccccaggct ccccagcagg   2760
cagaagtatg caaagcatgc atctcaatta gtcagcaacc aggtgtggaa agtccccagg   2820
ctccccagca ggcagaagta tgcaaagcat gcatctcaat tagtcagcaa ccatagtccc   2880
gcccctaact ccgcccatcc cgcccctaac tccgcccagt tccgcccatt ctccgcccca   2940
tggctgacta attttttta tttatgcaga ggccgaggcc gcctcggcct ctgagctatt   3000
ccagaagtag tgaggaggct tttttggagg cctaggcttt tgcaaaaagc tagcttgcat   3060
gcctgcaggt cggccgccac gaccggtgcc gccaccatcc cctgacccac gcccctgacc   3120
cctcacaagg agacgacctt ccatgaccga gtacaagccc acggtgcgcc tcgccacccg   3180
cgacgacgtc ccccgggccg tacgcaccct cgccgccgcg ttcgccgact accccgccac   3240
gcgccacacc gtcgacccgg accgccacat cgagcgggtc accgagctgc aagaactctt   3300
cctcacgcgc gtcgggctcg acatcggcaa ggtgtgggtc gcggacgacg gcgccgcggt   3360
ggcggtctgg accacgccgg agagcgtcga agcgggggcg gtgttcgccg agatcggccc   3420
gcgcatggcc gagttgagcg gttcccggct ggccgcgcag caacagatgg aaggcctcct   3480
ggcgccgcac cggcccaagg agcccgcgtg gttcctggcc accgtcggcg tctcgcccga   3540
ccaccagggc aagggtctgg gcagcgccgt cgtgctcccc ggagtggagg cggccgagcg   3600
cgccggggtg cccgccttcc tggagacctc cgcgccccgc aacctcccct tctacgagcg   3660
gctcggcttc accgtcaccg ccgacgtcga ggtgcccgaa ggaccgcgca cctggtgcat   3720
gacccgcaag cccggtgcct gacgcccgcc ccacgacccg cagcgcccga ccgaaaggag   3780
cgcacgaccc catggctccg accgaagcca cccggggcgg ccccgccgac cccgcacccg   3840
cccccgaggc ccaccgactc tagaggatca taatcagcca taccacattt gtagaggttt   3900
tacttgcttt aaaaaacctc ccacacctcc ccctgaacct gaaacataaa atgaatgcaa   3960
ttgttgttgt taacttgttt attgcagctt ataatggtta caaataaagc aatagcatca   4020
caaatttcac aaataaagca tttttttcac tgcaatctaa gaaaccatta ttatcatgac   4080
attaacctat aaaaataggc gtatcacgag gccctttcgt c                       4121
```